(12) United States Patent
Furuyama et al.

(10) Patent No.: US 8,329,711 B2
(45) Date of Patent: Dec. 11, 2012

(54) PYRIDONE-SUBSTITUTED-DIHYDRO-PYRAZOLOPYRIMIDINONE DERIVATIVE

(75) Inventors: Hidetomo Furuyama, Ashigarakami-gun (JP); Mikako Kawamura, Tsukuba (JP); Toshihiro Sakamoto, Moriya (JP); Fuyuki Yamamoto, Tsukuba (JP); Takashi Yoshizumi, Ushiku (JP)

(73) Assignee: MSD K.K., Chiyoda-Ku (JP)

( * ) Notice: Subject to any disclaimer, the term of this patent is extended or adjusted under 35 U.S.C. 154(b) by 154 days.

(21) Appl. No.: 12/738,885

(22) PCT Filed: Oct. 20, 2008

(86) PCT No.: PCT/JP2008/068932
§ 371 (c)(1),
(2), (4) Date: Apr. 20, 2010

(87) PCT Pub. No.: WO2009/054332
PCT Pub. Date: Apr. 30, 2009

(65) Prior Publication Data
US 2010/0221211 A1 Sep. 2, 2010

(30) Foreign Application Priority Data
Oct. 23, 2007 (JP) ................... 2007-275311

(51) Int. Cl.
*A01N 43/90* (2006.01)
*A61K 31/519* (2006.01)
*C07D 487/00* (2006.01)
(52) U.S. Cl. .................... 514/262.1; 544/262
(58) Field of Classification Search .......... None
See application file for complete search history.

(56) References Cited

U.S. PATENT DOCUMENTS

| | | |
|---|---|---|
| 2004/0220177 A1 | 11/2004 | Kath et al. |
| 2005/0054670 A1 | 3/2005 | Tegley et al. |
| 2005/0250836 A1 | 11/2005 | Booth et al. |
| 2007/0254892 A1 | 11/2007 | Sagara et al. |

FOREIGN PATENT DOCUMENTS

| | | |
|---|---|---|
| WO | 03091255 A1 | 11/2003 |
| WO | 2004056786 A2 | 7/2004 |
| WO | 2005021532 A1 | 3/2005 |
| WO | 2006074985 A1 | 7/2006 |
| WO | 2006091737 A1 | 8/2006 |

OTHER PUBLICATIONS

Palmer, BD et al., Biorganic & Medicinal Chemistry Letters, vol. 15, pp. 1931-1935 (2005), "Structure-activity relationships for 2-anilino-6-phenylpyrido[2,3-d]pyrimidin-7(8H)-ones as inhibitors of the cellular checkpoint kinase Wee1".
Wang, Y et al., Cancer Research, vol. 61, pp. 8211-8217 (2001), "Radiosensitization of p53 mutant cells by PD0166285, a Novel G2 checkpoint abrogator".

*Primary Examiner* — Jeffrey Murray
(74) *Attorney, Agent, or Firm* — Joan E. Switzer; David A. Muthard

(57) ABSTRACT

The invention relates to compounds of general formula (I-0):

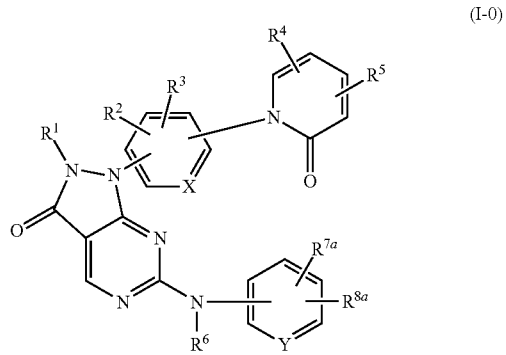

wherein $R^1$, $R^2$, $R^3$, $R^4$, $R^5$, $R^6$, $R^{7a}$, $R^{8a}$, X, and Y are as defined herein.

Compounds of the invention have, based on excellent Wee1 kinase-inhibitory effect, a cell growth-inhibitory effect and an additive/synergistic effect with any other anticancer agent, and are therefore useful in the field of medicine.

13 Claims, No Drawings

PYRIDONE-SUBSTITUTED-DIHYDRO-PYRAZOLOPYRIMIDINONE DERIVATIVE

PRIORITY CLAIM

This application claims priority from Japanese Provisional Application Serial No. JP2007/275311, filed Oct. 23, 2007 and PCT Application Serial No. JP2008/068932, filed on Oct. 20, 2008.

TECHNICAL FIELD

The present invention is useful in the field of medicine. More precisely, the pyridone-substituted dihydropyrazolopyrimidinone derivative of the invention is useful in the field of various cancer treatments, as a kinase inhibitor, especially as a Wee1 kinase inhibitor.

BACKGROUND ART

Cells have a checkpoint mechanism of such that, when the DNA therein is damaged, then the cells temporarily stop the cell cycle and repair the damaged DNA (Cell Proliferation, Vol. 33, pp. 261-274). In about a half of human cancers, a cancer-suppressor gene, p53 is mutated or depleted and the cells thereby have lost the G1 checkpoint function thereof. However, such cancer cells still keep the G2 checkpoint function remaining therein, which is considered to be one factor of lowering the sensitivity of the cells to DNA-active anticancer agents and to radiations.

A Wee1 kinase is a tyrosine kinase that participates in the G2 checkpoint of a cell cycle. Wee1 phosphorylates Cdc2 (Cdk1) tyrosine 15 that participates in the progress to the M stage from the G2 stage in a cell cycle, thereby inactivating Cdc2 and temporarily stopping the cell cycle at the G2 stage (The EMBO Journal, Vol. 12, pp. 75-85). Accordingly, in cancer cells having lost the p53 function therein, it is considered that the G2 checkpoint function by Wee1 is important for repairing the damaged DNA so as to evade the cell death. Heretofore, it has been reported that the Wee1 expression reduction by RNA interference or the Wee1 inhibition by compounds may increase the sensitivity of cancer cells to adriamycin, X ray and gamma ray (Cancer Biology & Therapy, Vol. 3, pp. 305-313; Cancer Research, Vol. 61, pp. 8211-8217). From the above, it is considered that a Wee1 inhibitor may inhibit the G2 checkpoint function of p53-depleted cancer cells, thereby enhancing the sensitivity of the cells to DNA-active anticancer agents and to radiations.

As a low-molecular Wee1 kinase inhibitor, for example, known are compounds described in US Application 2005/0250836 (Patent Reference 1), WO2003/091255 (Patent Reference 2), Cancer Research, Vol. 61, pp. 8211-8217 (Non-Patent Reference 1), or Bioorg & Med. Chem. Lett., Vol. 15, pp. 1931-1935 (Non-Patent Reference 2). However, the compounds described in these references quite differ from the compounds of the invention in point of their structures.

On the other hand, WO2004/056786 (Patent Reference 3), WO2005/021532 (Patent Reference 4) or WO2006/091737 (Patent Reference 5) discloses various compounds having dihydropyrazolopyrimidine portion etc relatively similar to the compounds of the invention in point of their skeletons. However, these references do neither disclose nor suggest the Wee1 kinase-inhibitory effect of those compounds and the compounds of the invention.

Non-Patent Reference 1: Cancer Research, Vol. 61, pp. 8211-8217

Non-Patent Reference 2: Bioorg & Med. Chem. Lett, Vol. 15, pp. 1931-1935

Patent Reference 1: US Application 2005/0250836

Patent Reference 2: WO2003/091255

Patent Reference 3: WO2004/056786

Patent Reference 4: WO2005/021532

Patent Reference 5: WO2006/091737

DISCLOSURE OF THE INVENTION

Problems that the Invention is to Solve

An object of the invention is to provide a novel anticancer agent having a kinase-inhibitory effect, especially a Wee1 kinase-inhibitory effect, or a sensitizer for chemotherapy or radiation therapy of cancers.

Means for Solving the Problems

As a result of assiduous studies, the present inventors have found that compounds of the following general formula (I-0) have an excellent kinase-inhibitory effect, especially an excellent Wee1 kinase-inhibitory effect, and have completed the present invention:

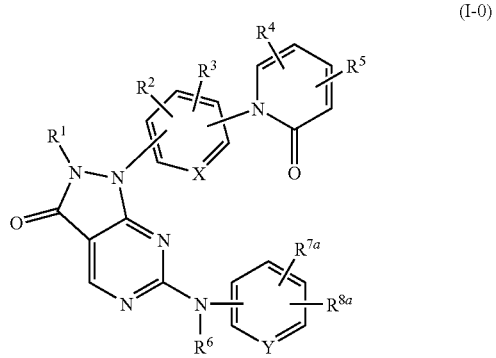

(I-0)

wherein $R^1$ means a C1-C6 alkyl group, a C2-C6 alkenyl group, a C2-C6 alkynyl group or a C3-C6 cycloalkyl group, any of which may be substituted with a halogen atom;

$R^2$, $R^3$, $R^4$ and $R^5$ each independently mean a hydrogen atom, a halogen atom, a C1-C6 alkyl group, a halo-C1-C6 alkyl group, a C1-C6 alkoxy group or a halo-C1-C6 alkoxy group;

$R^6$ means a hydrogen atom or a C1-C6 alkyl group;

$R^{7a}$ means a hydrogen atom, a halogen atom, a C1-C6 alkyl group, a halo-C1-C6 alkyl group, a C1-C6 alkoxy group, a hydroxy-C1-C6 alkyl group or a group of $-Q^2-N(R^{1c})R^{1d}$, or means a nitrogen-containing heterocyclic group optionally substituted with a substituent selected from the group consisting of a halogen atom, a C1-C6 alkyl group, a hydroxy-C1-C6 alkyl group, an oxo group and a group of $-Q^1-N(R^{1a})R^{1b}$;

$R^{8a}$ means a hydrogen atom, a halogen atom, a C1-C6 alkyl group, a halo-C1-C6 alkyl group, a C1-C6 alkoxy group or a hydroxy-C1-C6 alkyl group;

or when $R^{7a}$ and $R^{8a}$ exist on the ring atoms, adjacent to each other, of the group of the following formula (a):

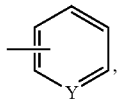

(a)

$R^{7a}$ and $R^{8a}$ may form, as taken together, a C2-C6 alkylene group, in which one or two methylene groups constituting the C2-C6 alkylene group may be each independently replaced by an oxygen atom or a group of —N($R^{1e}$)—, and the C2-C6 alkylene group may be substituted with a substituent selected from the group consisting of a halogen atom, a C1-C6 alkyl group and a halo-C1-C6 alkyl group; or $R^{7a}$ and $R^{8a}$ and the ring atoms to which they bond may be, as taken together, a spiro ring or a bicyclo ring to be formed of a 5-membered to 7-membered aliphatic ring and any other 3-membered to 7-membered aliphatic ring, in which one or two or more methylene groups constituting the spiro ring or the bicyclo ring may be each independently replaced by an oxygen atom, a sulfur atom, a sulfinyl group, a sulfonyl group, a carbonyl group or a group of —N($R^{1f}$)—, and the spiro ring or the bicyclo ring may be each independently substituted with a substituent selected from the group consisting of a halogen atom, a hydroxyl group, a C1-C6 alkyl group, a hydroxy-C1-C6 alkyl group or a group of -$Q^3$-N($R^{1g}$)$R^{1h}$;

$R^{1a}$ and $R^{1b}$ each independently mean a hydrogen atom, a C1-C6 alkyl group or a halo-C1-C6 alkyl group, or, as taken together, they may form a C2-C6 alkylene group, in which the C2-C6 alkylene group may be substituted with a substituent selected from the group consisting of a halogen atom, a C1-C6 alkyl group and a halo-C1-C6 alkyl group;

$R^{1c}$, $R^{1d}$ and $R^{1e}$ each independently mean a hydrogen atom, or mean a C1-C6 alkyl group optionally substituted with a substituent selected from the group consisting of a halogen atom, a hydroxyl group, an oxo group, a C3-C6 cycloalkyl group and a nitrogen-containing heterocyclic group;

$R^{1f}$ means a hydrogen atom, or means a C1-C6 alkyl group, a C3-C6 cycloalkyl group or a C2-C7 alkanoyl group, which may have a substituent selected from the group consisting of a halogen atom, a hydroxyl group, a cyano group, a C1-C6 alkoxy group, a C3-C6 cycloalkyl group and a C2-C7 alkanoyl group, or means a group of -$Q^4$-Cy of -$Q^5$-N($R^{1i}$)$R^{1j}$;

Cy means an aryl group or a heterocyclic group, any of which may be substituted with a halogen atom or a C1-C6 alkyl group;

$R^{1g}$ and $R^{1h}$ each independently mean a hydrogen atom, or mean a C1-C6 alkyl group, a C2-C7 alkanoyl group or a C1-C6 alkylsulfonyl group, which may have a substituent selected from the group consisting of a halogen atom, a hydroxyl group, a cyano group, a C1-C6 alkoxy group, a C3-C6 cycloalkyl group, a C2-C7 alkanoyl group and a C1-C6 alkylsulfonyl group, or mean a group of -$Q^6$-N($R^{1k}$)$R^{1l}$;

$R^{1i}$, $R^{1j}$, $R^{1k}$ and $R^{1l}$ each independently mean a hydrogen atom, or mean a C1-C6 alkyl group, a C2-C7 alkanoyl group or a C1-C6 alkylsulfonyl group, which may have a substituent selected from the group consisting of a halogen atom, a hydroxyl group, a cyano group, a C1-C6 alkoxy group, a C3-C6 cycloalkyl group, a C2-C7 alkanoyl group and a C1-C6 alkylsulfonyl group;

$Q^1$ and $Q^2$ each independently mean a single bond or a C1-C3 alkylene group;

$Q^3$, $Q^4$, $Q^5$ and $Q^6$ each independently means a single bond or a C1-C6 alkylene group, in which one or two or more methylene groups constituting the C1-C6 alkylene group may be each independently replaced by a sulfinyl group, a sulfonyl group or a carbonyl group; and X and Y each independently mean a methine group or a nitrogen atom.

The compounds (I-0) of the invention have a kinase-inhibitory effect, especially a Wee1 kinase-inhibitory effect, and they are useful as remedies for various cancers such as brain cancer, cervicocerebral cancer, esophageal cancer, thyroid cancer, small cell cancer, non-small cell cancer, breast cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' cancer, skin cancer, malignant melanoma, neuroblastoma, osteosarcoma, Ewing's tumor, soft part sarcoma, acute leukemia, chronic lymphatic leukemia, chronic myelocytic leukemia, Hodgkin's lymphoma, or as sensitizers for chemotherapy or radiation therapy of those cancers.

In particular, the compounds (I-0) of the invention are useful as remedies, for example, for breast cancer, lung cancer, pancreatic cancer, colon cancer, ovarian cancer, acute leukemia, chronic lymphatic leukemia, chronic myelocytic leukemia, Hodgkin's lymphoma, or as sensitizers for chemotherapy or radiation therapy of those cancers.

The invention relates to the compounds of formula (I-0), or their pharmaceutically-acceptable salts, as well as to their production methods and their use.

The meanings of the terms used in this description are described below, and the invention is described in more detail hereinunder.

"Halogen atom" means a fluorine atom, a chlorine atom, a bromine atom, an iodine atom.

"C1-C6 alkyl group" means a linear or branched alkyl group having from 1 to 6 carbon atoms, including, for example, a methyl group, an ethyl group, a propyl group, an isopropyl group, a butyl group, an isobutyl group, a sec-butyl group, a tert-butyl group, a pentyl group, an isopentyl group, a hexyl group, an isohexyl group.

"C2-C6 alkenyl group" means a linear or branched alkenyl group having from 2 to 6 carbon atoms, including, for example, a vinyl group, a 1-propenyl group, a 2-propenyl group, an isopropenyl group, a 3-butenyl group, a 2-butenyl group, a 1-butenyl group, a 1-methyl-2-propenyl group, a 1-methyl-1-propenyl group, a 1-ethyl-1-ethenyl group, a 2-methyl-2-propenyl group, a 2-methyl-1-propenyl group, a 3-methyl-2-butenyl group, a 4-pentenyl group.

"C2-C6 alkynyl group" means a linear or branched alkynyl group having from 2 to 6 carbon atoms, including, for example, an ethynyl group, a 1-propynyl group, a 2-propynyl group, a 3-butynyl group, a 2-butynyl group, a 1-butynyl group, a 1-methyl-2-propynyl group, a 1-ethyl-2-propynyl group, a 1-methyl-2-butynyl group, a 4-pentynyl group.

"C3-C6 cycloalkyl group" means a cycloalkyl group having from 3 to 6 carbon atoms, including, for example, a cyclopropyl group, a cyclobutyl group, a cyclopentyl group, a cyclohexyl group.

"Halo-C1-C6 alkyl group" means the above-mentioned C1-C6 alkyl group in which any substitutable position is substituted with one or two or more, preferably from 1 to 3, the same or different, above-mentioned halogen atoms, including, for example, a fluoromethyl group, a difluoromethyl group, a trifluoromethyl group, a 2-fluoroethyl group, a 1,2-difluoroethyl group, a chloromethyl group, a 2-chloroethyl group, a 1,2-dichloroethyl group, a bromomethyl group, an iodomethyl group.

"C1-C6 alkoxy group" means a linear or branched alkoxy group having from 1 to 6 carbon atoms, including, for example, a methoxy group, an ethoxy group, a propoxy group, an isopropoxy group, a butoxy group, a sec-butoxy group, an isobutoxy group, a tert-butoxy group, a pentyloxy group, an isopentyloxy group, a hexyloxy group, an isohexyloxy group.

"C2-C7 alkanoyl group" means an alkanoyl group having the above-mentioned C1-C6 alkyl group, or that is, an alkanoyl group having from 2 to 7 carbon atoms, including, for example, an acetyl group, a propionyl group, a butyryl group, an isobutyryl group, a valeryl group, an isovaleryl group, a pivaloyl group.

"Aryl group" includes, for example, a phenyl group, a naphthyl group.

"Heterocyclic group" means a 3-membered to 7-membered monocyclic heterocyclic group having one or two or more, preferably from 1 to 3, the same or different hetero atoms selected from the group consisting of an oxygen atom, a nitrogen atom and a sulfur atom; or a condensed cyclic heterocyclic group formed through condensation of that monocyclic heterocyclic group and a 3-membered to 7-membered carbocyclic group, or through condensation of the same or different such monocyclic heterocyclic groups; and it includes the above-mentioned heteroaryl group. Its concrete examples are those mentioned hereinabove for the heteroaryl group, and in addition, a pyrrolidinyl group, a dihydro-1,2,4-triazolyl group, a dihydro-1,2,4-oxadiazolyl group, a dihydro-1,3,4-oxadiazolyl group, a dihydro-1,2,4-thiadiazolyl group, a dihydro-1,2,3,5-oxathiadiazolyl group, a piperidyl group, a piperazinyl group, a morpholinyl group, a thiomorpholinyl group.

"C1-C6 alkylsulfonyl group" means a linear or branched alkylsulfonyl group having from 1 to 6 carbon atoms, including, for example, a methylsulfonyl group, an ethylsulfonyl group, a propylsulfonyl group, an isopropylsulfonyl group, a butylsulfonyl group, a sec-butylsulfonyl group, an isobutylsulfonyl group, a tert-butylsulfonyl group, a pentylsulfonyl group, an isopentylsulfonyl group, a hexylsulfonyl group, an isohexylsulfonyl group.

"Halo-C1-C6 alkoxy group" means the above-mentioned C1-C6 alkoxy group in which any substitutable position is substituted with one or two or more, preferably from 1 to 3, the same or different, above-mentioned halogen atoms, including, for example, a fluoromethoxy group, a chloromethoxy group, a difluoromethoxy group, a dichloromethoxy group, a trifluoromethoxy group, a 2-fluoroethoxy group, a 2-chloroethoxy group, a 2,2-difluoroethoxy group, a 1,2,2-trifluoroethoxy group, a 2,2,2-trifluoroethoxy group, a 3-fluoropropoxy group, a 3,3-difluoropropoxy group.

"Hydroxy-C1-C6 alkyl group" means the above-mentioned C1-C6 alkyl group in which any substitutable position is substituted with one or two or more, preferably one or two hydroxyl groups, including, for example, a hydroxymethyl group, a 2-hydroxyethyl group, a 1-hydroxy-1-methylethyl group, a 1,2-dihydroxyethyl group, a 3-hydroxypropyl group.

"3-Membered to 7-membered, or 5-membered to 7-membered aliphatic ring" means a structure comprising from 3 to 7, or from 5 to 7 atoms bonding to each other in a ring, and it may be a monocyclic saturated structure by itself, or may be an unsaturated bond-containing ring except an aromatic ring. For example, it includes cyclopropane, cyclopropene, cyclobutane, cyclobutene, cyclopentane, cyclopentene, cyclohexane, cyclohexene, cycloheptane, cycloheptene. The methylene group constituting the aliphatic ring may be "replaced by" or "substituted with" a predetermined atom or group, as described hereinunder.

"Nitrogen-containing heterocyclic group" means a monocyclic or bicyclic heterocyclic group containing at least one nitrogen atom, in which each ring comprises from 3 to 7 ring atoms and contains, in addition to the nitrogen atom, one or two or more, the same or different hetero atoms, but preferably one hetero atom selected from the group consisting of an oxygen atom, a nitrogen atom and a sulfur atom; and the heterocyclic group may be aromatic or aliphatic. The bicyclic heterocyclic group may have a spiro structure of which the two rings share one and the same ring atom, or may have a bicyclo structure of which the rings share two or more ring atoms. Examples of the nitrogen-containing heterocyclic group include, for example, a pyrrolyl group, an imidazolyl group, a pyrazolyl group, a thiazolyl group, an isothiazolyl group, an oxazolyl group, an isoxazolyl group, a triazolyl group, a tetrazolyl group, an oxadiazolyl group, a 1,2,3-thiadiazolyl group, a 1,2,4-thiadiazolyl group, a 1,3,4-thiadiazolyl group, a pyridyl group, a pyrazinyl group, a pyrimidinyl group, a pyridazinyl group, a 1,2,4-triazinyl group, a 1,3,5-triazinyl group, an indolyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a naphthyridinyl group, a quinoxalinyl group, a quinazolinyl group, a cinnolinyl group, a pteridinyl group, a pyrido[3,2-b]pyridyl group, an azetidinyl group, a pyrrolidinyl group, a dihydro-1,2,4-triazolyl group, a dihydro-1,2,4-oxadiazolyl group, a dihydro-1,3,4-oxadiazolyl group, a dihydro-1,2,4-thiadiazolyl group, a dihydro-1,2,3,5-oxathiadiazolyl group, a piperidinyl group, a piperazinyl group, a dihydropyridyl group, a morpholinyl group, a thiomorpholinyl group, a 2,6-diazaspiro[3.5]nonyl group, a 2,7-diazaspiro[3.5]nonyl group, a 2,7-diazaspiro[4.5]decyl group, or a 2,7-diazabicyclo[3.3.0]octyl group, a 3,6-diazabicyclo[3.3.0]octyl group.

"C2-C6 alkylene group" means an alkylene group having from 2 to 6 carbon atoms, including, for example, an ethylene group, a trimethylene group, a tetramethylene group, a pentamethylene group, a hexamethylene group.

"C1-C3 alkylene group" means an alkylene group having from 1 to 3 carbon atoms, including, for example, a methylene group, an ethylene group, a trimethylene group.

"Pharmaceutically-acceptable salts" of the compounds of the invention mean ordinary, pharmaceutically-acceptable salts. For example, when the compounds have a hydroxyl group, then they may form base-addition salts at the hydroxyl group; or when the compounds have an amino group or a basic nitrogen-containing heterocyclic group or any other heterocyclic group, they may form acid-addition salts at the amino group or the basic nitrogen-containing heterocyclic group or the other heterocyclic group.

The base-addition salts include, for example, alkali metal salts such as sodium salts, potassium salts; alkaline earth metal salts such as calcium salts, magnesium salts; ammonium salts; and organic amine salts such as trimethylamine salts, triethylamine salts, dicyclohexylamine salts, ethanolamine salts, diethanolamine salts, triethanolamine salts, procaine salts, N,N'-dibenzylethylenediamine salts.

The acid-addition salts include, for example, inorganic acid salts such as hydrochlorides, sulfates, nitrates, phosphates, perchlorates; organic acid salts such as maleates, fumarates, tartrates, citrates, ascorbates, trifluoroacetates;

and sulfonates such as methanesulfonates, isethionates, benzenesulfonates, p-toluenesulfonates.

For illustrating the compounds of the invention more concretely, preferred examples of the symbols used in this description are described below in more detail.

One embodiment of the invention includes a compound of the following general formula (I), or its pharmaceutically-acceptable salt:

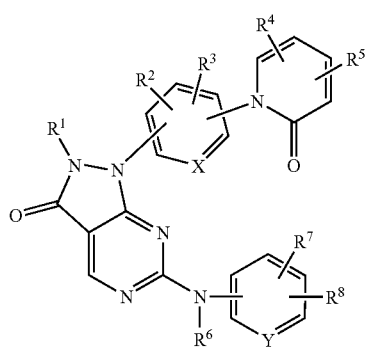

(I)

wherein R⁷ means a hydrogen atom, a halogen atom, a C1-C6 alkyl group, a halo-C1-C6 alkyl group, a C1-C6 alkoxy group, a hydroxy-C1-C6 alkyl group or a group of -Q²-N(R¹ᶜ)R¹ᵈ, or means a nitrogen-containing heterocyclic group optionally substituted with a substituent selected from the group consisting of a halogen atom, a C1-C6 alkyl group, a hydroxy-C1-C6 alkyl group, an oxo group and a group of -Q¹-N(R¹ᵃ)R¹ᵇ;

R⁸ means a hydrogen atom, a halogen atom, a C1-C6 alkyl group, a halo-C1-C6 alkyl group, a C1-C6 alkoxy group or a hydroxy-C1-C6 alkyl group;

or when R⁷ and R⁸ exist on the ring atoms, adjacent to each other, of the group of the following formula (a):

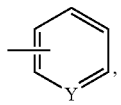

(a)

R⁷ and R⁸ may form, as taken together, a C2-C6 alkylene group, in which one or two methylene groups constituting the C2-C6 alkylene group may be each independently replaced by an oxygen atom or a group of —N(R¹ᵉ)—, and the C2-C6 alkylene group may be substituted with a substituent selected from the group consisting of a halogen atom, a C1-C6 alkyl group and a halo-C1-C6 alkyl group; and the definitions of R¹, R², R³, R⁴, R⁵, R⁶, R¹ᵃ, R¹ᵇ, R¹ᶜ, R¹ᵈ, R¹ᵉ, Q¹, Q², X and Y are the same as the definitions of those groups in the above-mentioned general formula (I-0).

The symbols used in the general formula (I) are described below.

R¹ means a C1-C6 alkyl group, a C2-C6 alkenyl group, a C2-C6 alkynyl group or a C3-C6 cycloalkyl group, any of which may be substituted with a halogen atom.

"A C1-C6 alkyl group, a C2-C6 alkenyl group, a C2-C6 alkynyl group or a C3-C6 cycloalkyl group, any of which may be substituted with a halogen atom" means the above-mentioned, unsubstituted C1-C6 alkyl group, C2-C6 alkenyl group, C2-C6 alkynyl group or C3-C6 cycloalkyl group, or means the above-mentioned C1-C6 alkyl group, C2-C6 alkenyl group, C2-C6 alkynyl group or C3-C6 cycloalkyl group in which any substitutable position is substituted with one or two or more, preferably from 1 to 3, the same or different, above-mentioned halogen atoms.

R¹ is preferably a C2-C6 alkenyl group such as a 2-propenyl group.

R², R³, R⁴ and R⁵ each independently mean a hydrogen atom, a halogen atom, a C1-C6 alkyl group, a halo-C1-C6 alkyl group, a C1-C6 alkoxy group or a halo-C1-C6 alkoxy group.

The group of the following formula (b):

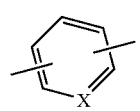

(b)

bonds to the group of the following adjacent formula (c) or (d) via any bondable ring atom thereof:

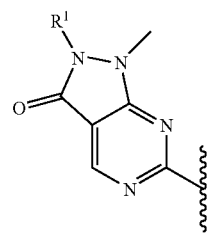

(c)

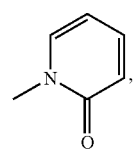

(d)

and R² and R³ each independently exist, as bonding to any bondable ring atom of the group of the formula (b).

Preferred embodiments of R² and R³ include a case where R² and R³ are both hydrogen atom; or a case where any one of R² and R³ is a hydrogen atom and the other is a halogen atom such as a fluorine atom.

X means a methine group or a nitrogen atom, and is preferably a nitrogen atom.

R⁴ and R⁵ each independently exist, as bonding to any bondable ring atom of the group of the following formula (d):

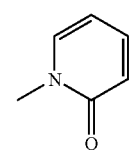

(d)

Preferred embodiments of R⁴ and R⁵ include a case where R⁴ and R⁵ are both hydrogen atoms; or a case where any one of R⁴ and R⁵ is a hydrogen atom and the other is a halogen atom such as a fluorine atom, a C1-C6 alkyl group such as a methyl group, a halo-C1-C6 alkyl group such as a trifluoromethyl group, or a C1-C6 alkoxy group such as a methoxy group. More preferred is a case where R⁴ and R⁵ are both hydrogen atoms, or a case where any one of $R^4$ and $R^5$ is a hydrogen atom and the other is a halogen atom such as a fluorine atom.

$R^6$ means a hydrogen atom or a C1-C6 alkyl group, and is preferably a hydrogen atom.

$R^7$ means a hydrogen atom, a halogen atom, a C1-C6 alkyl group, a halo-C1-C6 alkyl group, a C1-C6 alkoxy group, a hydroxy-C1-C6 alkyl group or a group of $-Q^2-N(R^{1c})R^{1d}$, or means a nitrogen-containing heterocyclic group optionally substituted with a substituent selected from the group consisting of a halogen atom, a C1-C6 alkyl group, a hydroxy-C1-C6 alkyl group, an oxo group and a group of $-Q^1-N(R^{1a})R^{1b}$.

In the group of $-Q^2-N(R^{1c})R^{1d}$, $Q^2$ means a single bond or a C1-C3 alkylene group; $R^{1c}$ and $R^{1d}$ each independently mean a hydrogen atom, or mean a C1-C6 alkyl group optionally substituted with a substituent selected from the group consisting of a halogen atom, a hydroxyl group, an oxo group, a C3-C6 cycloalkyl group and a nitrogen-containing heterocyclic group.

"A C1-C6 alkyl group optionally substituted with a substituent selected from the group consisting of a halogen atom, a hydroxyl group, an oxo group, a C3-C6 cycloalkyl group and a nitrogen-containing heterocyclic group" for $R^{1c}$ or $R^{1d}$ means the above-mentioned, unsubstituted C1-C6 alkyl group, or means the above-mentioned C1-C6 alkyl group having a substituent at any substitutable position thereof, in which the substituent may be one or two or more, preferably one or two, the same or different substituents selected from the group consisting of a halogen atom, a hydroxyl group, an oxo group, a C3-C6 cycloalkyl group and a nitrogen-containing heterocyclic group.

The halogen atom for the substituent is, for example, preferably a fluorine atom or a chlorine atom.

The C3-C6 cycloalkyl group for the substituent is, for example, preferably a cyclopropyl group.

The nitrogen-containing heterocyclic group for the substituent is, for example, preferably a pyridyl group.

The substituent is, for example, preferably a hydroxyl group, an oxo group, a C3-C6 cycloalkyl group, or a nitrogen-containing heterocyclic group.

"C1-C6 alkyl group" itself of the above-mentioned, optionally-substituted C1-C6 alkyl group for $R^{1c}$ or $R^{1d}$ is preferably a methyl group, an ethyl group, a propyl group, an isopropyl group, a 2-methylpropyl group or a tert-butyl group, more preferably a methyl group, an ethyl group or a tert-butyl group.

Preferred embodiments of the above-mentioned, optionally-substituted C1-C6 alkyl group for $R^{1c}$ or $R^{1d}$ include a methyl group, an ethyl group, a tert-butyl group, a 2-hydroxyethyl group, a cyclopropylcarbonyl group, a 2-pyridylmethyl group.

Preferably, $R^{1c}$ and $R^{1d}$ are each independently a hydrogen atom, or are a C1-C6 alkyl group optionally substituted with a substituent selected from the group consisting of a hydroxyl group, an oxo group, a C3-C6 cycloalkyl group and a pyridyl group.

Accordingly, preferred embodiments of the group of $-Q^2-N(R^{1c})R^{1d}$ include, for example, a tert-butylaminomethyl group, a methyl(2-pyridylmethyl)amino group, a diethylaminomethyl group, a 3-(dimethylamino)propyl group, a 3-[2-hydroxyethyl(methyl)amino]propyl group, a cyclopropylcarbonylamino group.

"Nitrogen-containing heterocyclic group optionally substituted with a substituent selected from the group consisting of a halogen atom, a C1-C6 alkyl group, a hydroxy-C1-C6 alkyl group, an oxo group and a group of $-Q^1-N(R^{1a})R^{1b}$" means the above-mentioned, unsubstituted nitrogen-containing heterocyclic group, or means the above-mentioned nitrogen-containing heterocyclic group having a substituent at any substitutable position thereof, in which the substituent may be one or two or more, preferably one or two, the same or different substituents selected from the group consisting of a halogen atom, a C1-C6 alkyl group, a hydroxy-C1-C6 alkyl group, an oxo group and a group of $-Q^1-N(R^{1a})R^{1b}$.

The halogen atom for the substituent is, for example, preferably a fluorine atom or a chlorine atom.

The C1-C6 alkyl group for the substituent is, for example, preferably a methyl group or an ethyl group.

The hydroxy-C1-C6 alkyl group for the substituent is, for example, preferably a hydroxymethyl group.

In the group of $-Q^1-N(R^{1a})R^{1b}$ for the substituent, $Q^1$ means a single bond or a C1-C3 alkylene group; and $R^{1a}$ and $R^{1b}$ each independently mean a hydrogen atom, a C1-C6 alkyl group or a halo-C1-C6 alkyl group, or, as taken together, they may form a C2-C6 alkylene group, in which the C2-C6 alkylene group may be substituted with a substituent selected from the group consisting of a halogen atom, a C1-C6 alkyl group and a halo-C1-C6 alkyl group.

The C1-C6 alkyl group for $R^{1a}$ or $R^{1b}$ is, for example, preferably a methyl group, an ethyl group or a tert-butyl group.

The C2-C6 alkylene group formed by $R^{1a}$ and $R^{1b}$ taken together is, for example, preferably a tetramethylene group; and the tetramethylene group, as taken together with the adjacent nitrogen atom, forms a 1-pyrrolidinyl group.

Preferably, $R^{1a}$ and $R^{1b}$ each are independently a hydrogen atom or a C1-C6 alkyl group, or as taken together, they form a C2-C6 alkylene group.

Accordingly, the group of $-Q^1-N(R^{1a})R^{1b}$ is, for example, preferably a dimethylamino group, a tert-butylamino group or a 1-pyrrolidinylmethyl group.

"Substituent" of the nitrogen-containing heterocyclic group optionally substituted with the above-mentioned substituent for $R^7$ is, for example, preferably a halogen atom such as a fluorine atom; a C1-C6 alkyl group such as a methyl group; a hydroxy-C1-C6 alkyl group such as a hydroxymethyl group; an oxo group; or a group of $-Q^1-N(R^{1a})R^{1b}$ such as a dimethylamino group, a tert-butylamino group or a 1-pyrrolidinylmethyl group.

"Nitrogen-containing heterocyclic group" itself of the nitrogen-containing heterocyclic group optionally substituted with the above-mentioned substituent for $R^7$ is, for example, preferably an azetidinyl group, a pyrrolidinyl group, a piperidinyl group, a piperazinyl group, a dihydropyridyl group, a 2,7-diazaspiro[3.5]nonyl group, a 2,7-diazabicyclo[3.3.0]octyl group, or a 3,6-diazabicyclo[3.3.0]octyl group; more concretely, preferably an azetidin-1-yl group, a pyrrolidin-1-yl group, a 4-piperidinyl group, a 1-piperazinyl group, a 1,2-dihydropyridin-1-yl group, a 2,7-diazaspiro[3.5]non-7-yl group, a 2,7-diazabicyclo[3.3.0]oct-2-yl group, or a 3,6-diazabicyclo[3.3.0]oct-3-yl group; even more preferably a pyrrolidin-1-yl group, or a 4-piperidinyl group.

Accordingly, the nitrogen-containing heterocyclic group optionally substituted with the above-mentioned substituent for $R^7$ is, for example, preferably, a 3,3-difluoroazetidin-1-yl group, a 3-dimethylaminoazetidin-1-yl group, a 2-(1-pyrrolidinylmethyl)pyrrolidin-1-yl group, a 2-(hydroxymethyl)pyrrolidin-1-yl group, a 2-oxopyrrolidin-1-yl group, a 3-(tert-butylamino)pyrrolidin-1-yl group, a 3-dimethylaminopyrrolidin-1-yl group, a 1-methyl-4-piperidinyl group, a 2-oxo-1,2-dihydropyridin-1-yl group, a 4-methyl-1-piperazinyl group, a 2-methyl-2,7-diazaspiro[3.5]non-7-yl group, a 7-methyl-2,7-diazabicyclo[3.3.0]oct- 2-yl group, a 6-methyl-3,6-diazabicyclo[3.3.0]oct-3-yl group; more preferably a 3-dimethylaminopyrrolidin-1-yl group, or a 1-methyl-4-piperidinyl group.

Preferably, $R^7$ is a group of $-Q^2-N(R^{1c})R^{1d}$, or is a nitrogen-containing heterocyclic group optionally substituted with a substituent selected from the group consisting of a halogen atom, a C1-C6 alkyl group, a hydroxy-C1-C6 alkyl group, an oxo group and a group of $-Q^1-N(R^{1a})R^{1b}$.

$R^8$ means a hydrogen atom, a halogen atom, a C1-C6 alkyl group, a halo-C1-C6 alkyl group, a C1-C6 alkoxy group or a hydroxy-C1-C6 alkyl group.

$R^8$ is preferably a hydrogen atom; a C1-C6 alkyl group such as a methyl group; a C1-C6 alkoxy group such as a methoxy group; or a hydroxy-C1-C6 alkyl group such as a hydroxymethyl group.

The group of the following formula (a):

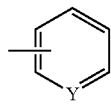
(a)

bonds to the group of the following adjacent formula (c') via any bondable ring atom thereof:

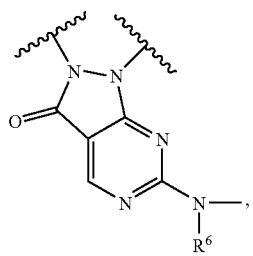
(c')

and $R^7$ and $R^8$ exist, as bonding to any bondable ring atom of the group of the formula (a). When $R^7$ and $R^8$ exist on the ring atoms, adjacent to each other, of the group of the formula (a), then $R^7$ and $R^8$ may form, as taken together, a C2-C6 alkylene group, in which one or two methylene groups constituting the C2-C6 alkylene group may be each independently replaced by an oxygen atom or a group of $-N(R^{1e})-$, and the C2-C6 alkylene group may be substituted with a substituent selected from the group consisting of a halogen atom, a C1-C6 alkyl group and a halo-C1-C6 alkyl group.

In one aspect of the invention, the group of the formula (a-1):

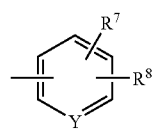
(a-1)

is a group of a formula (a-2):

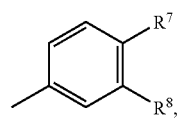
(a-2)

in which $R^7$ and $R^8$, as taken together, form a C2-C6 alkylene group, and one or two methylene groups constituting the C2-C6 alkylene group are each independently replaced by a group of $-N(R^{1e})-$, and $R^{1e}$ is a C1-C6 alkyl group.

In another aspect of the invention, the C2-C6 alkylene group to be formed by $R^7$ and $R^8$ taken together means, for example, a tetramethylene group, and the tetramethylene group form, for example, as taken together with the group of the above-mentioned formula (a), a group of the following formula (a-10):

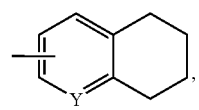
(a-10)

and, an example where the methylene group constituting the tetramethylene group is replaced by an oxygen atom or a group of $-N(R^{1e})-$ includes groups of the following formula (a-11):

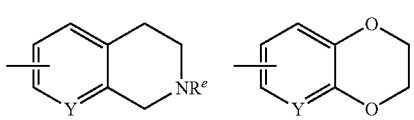
(a-11)

The C2-C6 alkylene group moiety such as the tetramethylene group as above may be substituted with the above-mentioned substituent, and the substituent is preferably a halogen atom such as a fluorine atom, or a C1-C6 alkyl group such as a methyl group.

Y means a methine group or a nitrogen atom, and is preferably a methine group.

Concretely, the group of the formula (a-1):

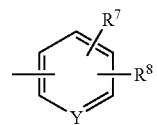
(a-1)

is, for example, preferably a 3-hydroxymethyl-4-methoxyphenyl group, a 4-(tert-butylaminomethyl)phenyl group, a 4-[methyl(2-pyridylmethyl)amino]phenyl group, a 4-(diethylaminomethyl)phenyl group, a 4-[3-(dimethylamino) propyl]phenyl group, a 4-[3-[2-hydroxyethyl(methyl)amino] propyl]phenyl group, a 4-(cyclopropylcarbonylamino) phenyl group, a 4-(3,3-difluoroazetidin-1-yl)phenyl group, a 4-(3-dimethylaminoazetidin-1-yl)phenyl group, a 4-[2-(1-pyrrolidinylmethyl)pyrrolidin-1-yl]phenyl group, a 4-[2-(hydroxymethyl)pyrrolidin-1-yl]phenyl group, a 4-(2-oxopyrrolidin-1-yl)phenyl group, a 4-[3-(tert-butylamino)pyrrolidin-1-yl]phenyl group, a 4-(3-dimethylaminopyrrolidin-1-yl) phenyl group, a 3-(1-methyl-4-piperidinyl)phenyl group, a 4-(1-methyl-4-piperidinyl)phenyl group, a 4-(2-oxo-1,2-dihydropyridin-1-yl)phenyl group, a 4-(4-methyl-1-piperazinyl)phenyl group, a 3-methyl-4-(4-methyl-1-piperazinyl) phenyl group, a 3-hydroxymethyl-4-(4-methyl-1-piperazinyl)phenyl group, a 4-(2-methyl-2,7-diazaspiro[3.5] non-7-yl)phenyl group, a 4-(7-methyl-2,7-diazabicyclo [3.3.0]oct-2-yl)phenyl group, a 4-(6-methyl-3,6-diazabicyclo[3.3.0]oct-3-yl)phenyl group, a 2-methyl-1,2,3, 4-tetrahydroisoquinolin-6-yl group, a 2-methyl-1,2,3,4- tetrahydroisoquinolin-7-yl group, a 2,4,4-trimethyl-1,2,3,4-tetrahydroisoquinolin-7-yl group, a 2,2,3,3-tetrafluoro-2,3-dihydro-1,4-benzodioxin-6-yl group; more preferably a 4-(3-dimethylaminopyrrolidin-1-yl)phenyl group, or a 4-(4-methyl-1-piperazinyl)phenyl group.

One aspect of the invention is a compound of general formula (I-1):

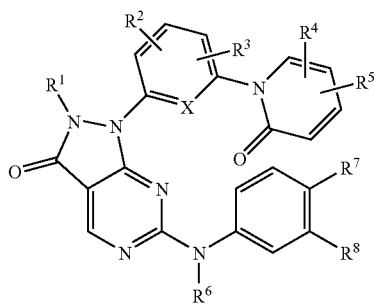

(I-1)

wherein $R^1$, $R^2$, $R^3$, $R^4$, $R^5$, $R^6$, $R^7$, $R^8$ and X have the same meanings as above.

Preferred examples of $R^1$, $R^2$, $R^3$, $R^4$, $R^5$, $R^6$, $R^7$, $R^8$ and X in the compounds of the general formula (I-1) are the same as the preferred examples of $R^1$, $R^2$, $R^3$, $R^4$, $R^5$, $R^6$, $R^7$, $R^8$ and X in the above-mentioned compounds of the general formula (I).

Another aspect of the invention is a compound of general formula (I-2):

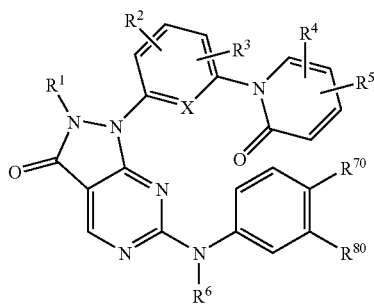

(I-2)

wherein $R^{10}$ means a C2-C6 alkenyl group; $R^{70}$ means a group of $-Q^2-N(R^{10c})R^{10d}$, or means a nitrogen-containing heterocyclic group selected from the group consisting of a an azetidin-1-yl group, a pyrrolidin-1-yl group, a 4-piperidinyl group, a 1-piperazinyl group, a 1,2-dihydropyridin-1-yl group, a 2,7-diazaspiro[3.5]non-7-yl group, a 2,7-diazabicyclo[3.3.0]oct-2-yl group and a 3,6-diazabicyclo[3.3.0]oct-3-yl group, any of which may be substituted with a substituent selected from the group consisting of a halogen atom, a C1-C6 alkyl group, a hydroxy-C1-C6 alkyl group, an oxo group and a group of $-Q^1-N(R^{10a})R^{10b}$; $R^{80}$ means a hydrogen atom, a C1-C6 alkyl group, a C1-C6 alkoxy group or a hydroxy-C1-C6 alkyl group; or $R^{70}$ and $R^{80}$ may form, as taken together, a C2-C6 alkylene group, and one or two methylene groups constituting the C2-C6 alkylene group are each independently replaced by a group of $-N(R^{10e})-$; $R^{10a}$ and $R^{10b}$ each independently mean a hydrogen atom or a C1-C6 alkyl group, or, as taken together, they form a C2-C6 alkylene group; $R^{10c}$ and $R^{10d}$ each independently mean a C1-C6 alkyl group optionally substituted with a substituent selected from the group consisting of a hydroxyl group, an oxo group, a C3-C6 cycloalkyl group and a pyridyl group; $R^{10e}$ means a C1-C6 alkyl group; and $Q^1$, $Q^2$, $R^2$, $R^3$, $R^4$, $R^5$, $R^6$ and X have the same meanings as above.

Preferred examples of $R^2$, $R^3$, $R^4$, $R^5$, $R^6$ and X in the compounds of the general formula (I-2) are the same as the preferred examples of $R^2$, $R^3$, $R^4$, $R^5$, $R^6$ and X in the above-mentioned compounds of the general formula (I); and preferred examples of $R^{10}$, $R^{70}$ and $R^{80}$ in the compounds of the general formula (I-2) are the same as the preferred examples of $R^1$, $R^7$ and $R^8$, respectively, in the above-mentioned compounds of the general formula (I).

In another embodiment of the invention, $R^{7a}$ and $R^{8a}$ in the general formula (I-0) exist on the ring atoms, adjacent to each other, of the group of the following formula (a):

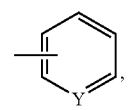

(a)

and $R^{7a}$ and $R^{8a}$ and the ring atoms to which they bond form, as taken together, a spiro ring or a bicyclo ring to be formed of a 5-membered to 7-membered aliphatic ring and any other 3-membered to 7-membered aliphatic ring, in which one or two or more methylene groups constituting the spiro ring or the bicyclo ring may be each independently replaced by an oxygen atom, a sulfur atom, a sulfinyl group, a sulfonyl group, a carbonyl group or a group of $-N(R^{1f})-$, and the spiro ring or the bicyclo ring may be each independently substituted with a substituent selected from the group consisting of a halogen atom, a hydroxyl group, a C1-C6 alkyl group, a hydroxy-C1-C6 alkyl group or a group of $-Q^3-N(R^{1g})R^{1h}$.

"Spiro ring composed of a 5-membered to 7-membered aliphatic ring and any other 3-membered to 7-membered aliphatic ring, which is formed by $R^{7a}$ and $R^{8a}$ and the ring atoms to which they bond" means a spiro ring formed by the aliphatic ring moiety of a 5-membered to 7-membered aliphatic ring ortho-condensed with the ring of the formula (a) and, as taken together with it, a any other 3-membered to 7-membered aliphatic ring that shares one ring atom of the aliphatic ring moiety of the aliphatic ring, and, for example, this constitutes, as taken together with the ring of the formula (a), a tricyclic group of the following formula (a-12):

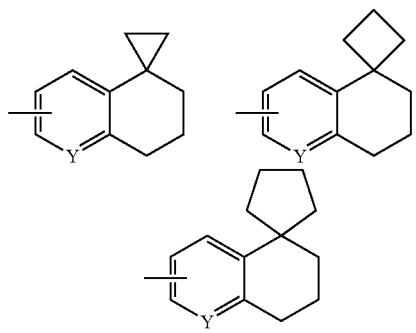

(a-12)

"Bicyclo ring composed of a 5-membered to 7-membered aliphatic ring and any other 3-membered to 7-membered aliphatic ring, which is formed by $R^{7a}$ and $R^{8a}$ and the ring atoms to which they bond" means a bicyclo ring formed by the aliphatic ring moiety of a 5-membered to 7-membered aliphatic ring ortho-condensed with the ring of the formula (a) and, as taken together with it, any other 3-membered to 7-membered aliphatic ring that shares at least two ring atoms of the aliphatic ring moiety of the aliphatic ring, and, for example, this constitutes, as taken together with the ring of the formula (a), a tricyclic group of the following formula (a-13):

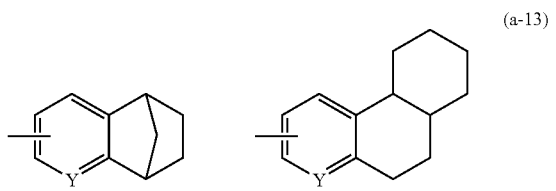
(a-13)

One or two or more methylene groups constituting the spiro ring or the bicyclo ring may be each independently replaced by an oxygen atom, a sulfur atom, a sulfinyl group, a sulfonyl group, a carbonyl group or a group of —N(R$^{1f}$)—. "One or two or more methylene groups constituting the spiro ring or the bicyclo ring may be each independently replaced by an oxygen atom, a sulfur atom, a sulfinyl group, a sulfonyl group, a carbonyl group or a group of —N(R$^{1f}$)—" as referred to herein means that one or two or more methylene groups themselves that constitute the spiro ring or the bicyclo ring are replaced or are not replaced by one or two or more, preferably from 1 to 3 groups or atoms that are the same or different and are selected from the group consisting of an oxygen atom, a sulfur atom, a sulfinyl group, a sulfonyl group, a carbonyl group and a group of —N(R$^{1f}$)—; and as a result of such replacement, the group of a formula (a-0):

(a-0)

includes a group selected from those of a formula (a-14):

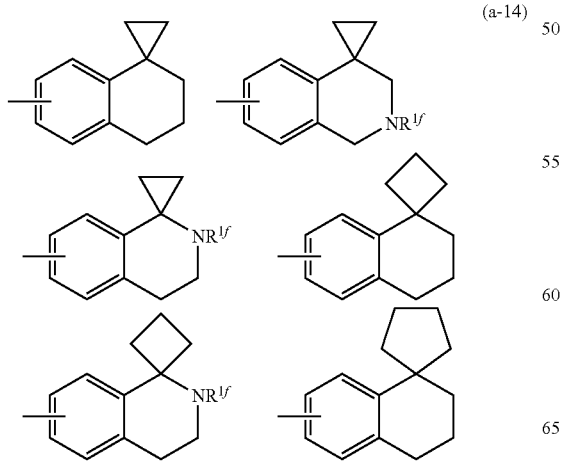
(a-14)

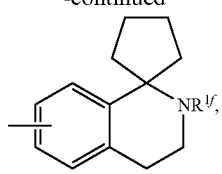

or a group selected from those of a formula (a-15):

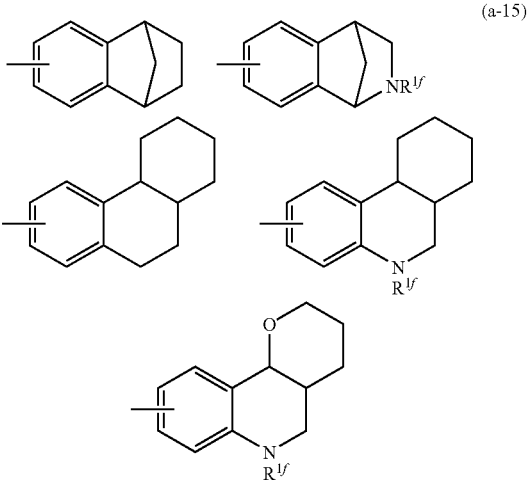
(a-15)

Of the groups of the formula (a-14), preferred embodiments includes groups selected from those of a formula (a-16):

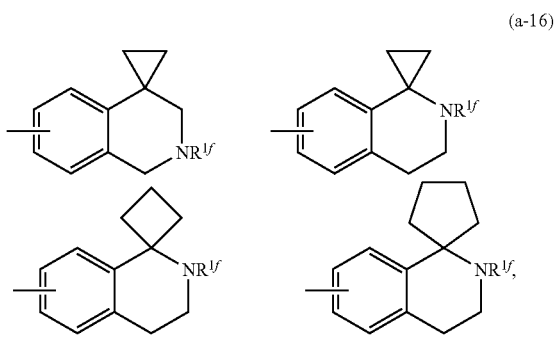
(a-16)

and more preferred embodiments are those of a formula (a-17):

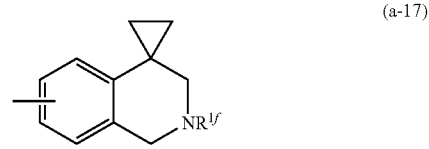
(a-17)

R$^{1f}$ each independently means a hydrogen atom, or means a C1-C6 alkyl group, a C3-C6 cycloalkyl group or a C2-C7 alkanoyl group, which may have a substituent selected from the group consisting of a halogen atom, a hydroxyl group, a cyano group, a C1-C6 alkoxy group, a C3-C6 cycloalkyl group and a C2-C6 alkanoyl group, or means a group of -Q⁴-Cy of -Q⁵-N(R¹ⁱ)R¹ʲ.

"A C1-C6 alkyl group, a C3-C6 cycloalkyl group or a C2-C7 alkanoyl group, which may have a substituent selected from the group consisting of a halogen atom, a hydroxyl group, a cyano group, a C1-C6 alkoxy group, a C3-C6 cycloalkyl group and a C2-C6 alkanoyl group" means the above-mentioned, unsubstituted C1-C6 alkyl group, C3-C6 cycloalkyl group or C2-C7 alkanoyl group, or means the above-mentioned C1-C6 alkyl group, C3-C6 cycloalkyl group or C2-C7 alkanoyl group having a substituent at any substitutable position thereof, in which the substituent may be one or two or more, preferably one or two, the same or different substituents selected from the group consisting of a halogen atom, a hydroxyl group, a cyano group, a C1-C6 alkoxy group, a C3-C6 cycloalkyl group and a C2-C7 alkanoyl group.

The substituent is preferably a halogen atom such as a chlorine atom, a bromine atom; a hydroxyl group; a C1-C6 alkoxy group such as a methoxy group, ethoxy group; a C3-C6 cycloalkyl group such as a cyclopropyl group; or a C2-C7 alkanoyl group such as an acetyl group; more preferably a halogen atom such as a fluorine atom; a hydroxyl group; or a C1-C6 alkoxy group such as a methoxy group.

"C1-C6 alkyl group" itself of the above-mentioned, optionally-substituted C1-C6 alkyl group for R¹ᶠ is preferably a methyl group, an ethyl group, a propyl group, an isopropyl group or a 2-methylpropyl group, more preferably a methyl group or an ethyl group.

Preferred embodiments of the above-mentioned, optionally-substituted C1-C6 alkyl group for R¹ᶠ include a methyl group, an ethyl group, an isopropyl group, a 2,2-difluoroethyl group, a 2-hydroxyethyl group, a 2-hydroxypropyl group, a 2-hydroxy-2-methylpropyl group, a 2-methoxyethyl group; and more preferred are a methyl group, an ethyl group, a 2-hydroxyethyl group.

The above-mentioned, optionally-substituted C3-C6 cycloalkyl group for R¹ᶠ is preferably a cyclopropyl group.

The above-mentioned, optionally-substituted C2-C7 alkanoyl group for R¹ᶠ is preferably an acetyl group.

In the group of -Q⁴-Cy, Cy means an aryl group or a heterocyclic group, any of which may be substituted with a halogen atom or a C1-C6 alkyl group; Q⁴ means a single bond or a C1-C6 alkylene group, in which one or two or more methylene groups constituting the C1-C6 alkylene group may be each independently replaced by a sulfinyl group, a sulfonyl group or a carbonyl group.

"An aryl group or a heterocyclic group, any of which may be substituted with a halogen atom or a C1-C6 alkyl group" means the above-mentioned, unsubstituted aryl group or heterocyclic group, or the above-mentioned aryl group or heterocyclic group having a substituent at any substitutable position thereof, in which the substituent may be one or two or more, preferably one or two, the same or different substituents selected from a halogen atom and a C1-C6 alkyl group.

The substituent is preferably a halogen atom such as a chlorine atom or a fluorine atom; or a C1-C6 alkyl group such as a methyl group or an ethyl group.

The aryl group for Cy is preferably a phenyl group; and the heterocyclic group is preferably a pyridyl group, a tetrahydrofuryl group or a pyrrolidinyl group, more preferably a pyridyl group.

The C1-C6 alkylene group for Q⁴ is preferably a methylene group or an ethylene group.

Preferred embodiments of the group of -Q⁴-Cy include an aralkyl group, preferably a benzyl group, a 2-pyridyl group, a tetrahydrofuran-3-ylmethyl group, a 1-methyl-2-pyrrolidinylmethyl group, or a 2-(1-pyrrolidinyl)ethyl group, more preferably a 2-pyridyl group.

In the group of -Q⁵-N(R¹ⁱ)R¹ʲ, R¹ⁱ and R¹ʲ each independently mean a hydrogen atom, or mean a C1-C6 alkyl group, a C2-C7 alkanoyl group or a C1-C6 alkylsulfonyl group, which may have a substituent selected from the group consisting of a halogen atom, a hydroxyl group, a cyano group, a C1-C6 alkoxy group, a C3-C6 cycloalkyl group, a C2-C7 alkanoyl group and a C1-C6 alkylsulfonyl group; Q⁵ means a single bond or a C1-C6 alkylene group, in which one or two or more methylene groups constituting the C1-C6 alkylene group may be each independently replaced by a sulfinyl group, a sulfonyl group or a carbonyl group.

"A C1-C6 alkyl group, a C2-C7 alkanoyl group or a C1-C6 alkylsulfonyl group, which may have a substituent selected from the group consisting of a halogen atom, a hydroxyl group, a cyano group, a C1-C6 alkoxy group, a C3-C6 cycloalkyl group, a C2-C7 alkanoyl group and a C1-C6 alkylsulfonyl group" means the above-mentioned, unsubstituted C1-C6 alkyl group, C2-C7 alkanoyl group or C1-C6 alkylsulfonyl group, or means the above-mentioned C1-C6 alkyl group, C2-C7 alkanoyl group or C1-C6 alkylsulfonyl group having a substituent at any substitutable position thereof, in which the substituent may be one or two or more, preferably one or two, the same or different substituents selected from the group consisting of a halogen atom, a hydroxyl group, a cyano group, a C1-C6 alkoxy group, a C3-C6 cycloalkyl group, a C2-C7 alkanoyl group and a C1-C6 alkylsulfonyl group.

The substituent is preferably a halogen atom such as a chlorine atom or a fluorine atom; a hydroxyl group; a C1-C6 alkoxy group such as a methoxy group or an ethoxy group; a C3-C6 cycloalkyl group such as a cyclopropyl group; a C2-C7 alkanoyl group such as an acetyl group; or a C1-C6 alkylsulfonyl group such as a methylsulfonyl group; more preferably a halogen atom such as a fluorine atom, or a hydroxyl group.

"C1-C6 alkyl group" itself of the above-mentioned, optionally-substituted C1-C6 alkyl group for R¹ⁱ or R¹ʲ is preferably a methyl group, an ethyl group, a propyl group, more preferably a methyl group or an ethyl group.

The above-mentioned, optionally-substituted C2-C7 alkanoyl group for R¹ⁱ or R¹ʲ is preferably an acetyl group.

The above-mentioned, optionally-substituted C1-C6 alkylsulfonyl group for R¹ⁱ or R¹ʲ is preferably a methylsulfonyl group.

The C1-C6 alkylene group for Q⁵ is preferably a methylene group or an ethylene group.

Preferred embodiments of the group of -Q⁵-N(R¹ⁱ)R¹ʲ include a 2-(dimethylamino)ethyl group, a dimethylaminocarbonylmethyl group, a dimethylaminomethylcarbonyl group, a 2-[methyl(methylsulfonyl)amino]ethyl group, and a 2-[acetyl(methyl)amino]ethyl group; and more preferred are a 2-(dimethylamino)ethyl group, a dimethylaminocarbonylmethyl group and a dimethylaminomethylcarbonyl group.

Preferred embodiments of R¹ᶠ include a hydrogen atom, above-mentioned, optionally-substituted C1-C6 alkyl group or C2-C7 alkanoyl group, and a group of -Q⁵-N(R¹ⁱ)R¹ʲ; more preferred are the above-mentioned, optionally-substituted C1-C6 alkyl group and C2-C7 alkanoyl group; and even more preferred is the above-mentioned, optionally-substituted C1-C6 alkyl group.

One or two or more methylene groups constituting the aliphatic ring of the "spiro ring or bicyclo ring" formed by R⁷ᵃ and R⁸ᵃ and the ring atoms to which they bond, as taken together, may be each independently substituted with a halogen atom, a hydroxyl group, a C1-C6 alkyl group, a hydroxy-C1-C6 alkyl group or group of -$Q^3$-N($R^{1g}$)$R^{1h}$.

The halogen atom for the substituent is preferably a chlorine atom or a fluorine atom.

The C1-C6 alkyl group for the substituent is preferably a methyl group or an ethyl group.

The hydroxy-C1-C6 alkyl group for the substituent is preferably a hydroxymethyl group or a 2-hydroxyethyl group.

In the group of -$Q^3$-N($R^{1g}$)$R^{1h}$, $R^{1g}$ and $R^{1h}$ each independently mean a hydrogen atom, or mean a C1-C6 alkyl group, a C2-C7 alkanoyl group or a C1-C6 alkylsulfonyl group, which may have a substituent selected from the group consisting of a halogen atom, a hydroxyl group, a cyano group, a C1-C6 alkoxy group, a C3-C6 cycloalkyl group, a C2-C7 alkanoyl group and a C1-C6 alkylsulfonyl group, or mean a group of -$Q^6$-N($R^{1k}$)$R^{1l}$; $Q^3$ means a single bond or a C1-C6 alkylene group, in which one or two or more methylene groups constituting the C1-C6 alkylene group may be each independently replaced by a sulfinyl group, a sulfonyl group or a carbonyl group.

"A C1-C6 alkyl group, a C2-C7 alkanoyl group or a C1-C6 alkylsulfonyl group, which may have a substituent selected from the group consisting of a halogen atom, a hydroxyl group, a cyano group, a C1-C6 alkoxy group, a C3-C6 cycloalkyl group, a C2-C7 alkanoyl group and a C1-C6 alkylsulfonyl group" means the above-mentioned, unsubstituted C1-C6 alkyl group, C2-C7 alkanoyl group or C1-C6 alkylsulfonyl group, or means the above-mentioned C1-C6 alkyl group, C2-C7 alkanoyl group or C1-C6 alkylsulfonyl group having a substituent at any substitutable position thereof, in which the substituent may be one or two or more, preferably one or two, the same or different substituents selected from the group consisting of a halogen atom, a hydroxyl group, a cyano group, a C1-C6 alkoxy group, a C3-C6 cycloalkyl group, a C2-C7 alkanoyl group and a C1-C6 alkylsulfonyl group.

The substituent is preferably a halogen atom such as a chlorine atom or a fluorine atom; a hydroxyl group; a C1-C6 alkoxy group such as a methoxy group or an ethoxy group; a C3-C6 cycloalkyl group such as a cyclopropyl group; a C2-C7 alkanoyl group such as an acetyl group; or a C1-C6 alkylsulfonyl group such as a methylsulfonyl group; more preferably a hydroxyl group.

"C1-C6 alkyl group" itself of the above-mentioned optionally-substituted C1-C6 alkyl group for $R^{1g}$ or $R^{1h}$ is preferably a methyl group, an ethyl group, a propyl group, more preferably a methyl group or an ethyl group.

Preferred embodiments of the above-mentioned optionally-substituted C1-C6 alkyl group for $R^{1g}$ or $R^{1h}$ include a methyl group, an ethyl group, an isopropyl group, a 2,2-difluoroethyl group, a 2-hydroxyethyl group, a 2-hydroxypropyl group, a 2-hydroxy-2-methylpropyl group and a 2-methoxyethyl group; and more preferred are a methyl group and a 2-hydroxyethyl group.

The above-mentioned optionally-substituted C2-C7 alkanoyl group for $R^{1g}$ or $R^{1h}$ is preferably an acetyl group.

The above-mentioned optionally-substituted C1-C6 alkylsulfonyl group for $R^{1g}$ or $R^{1h}$ is preferably a methylsulfonyl group.

In the group of -$Q^6$-N($R^{1k}$)$R^{1l}$, $R^{1k}$ and $R^{1l}$ each independently mean a hydrogen atom, or mean a C1-C6 alkyl group, a C2-C7 alkanoyl group or a C1-C6 alkylsulfonyl group, which may have a substituent selected from the group consisting of a halogen atom, a hydroxyl group, a cyano group, a C1-C6 alkoxy group, a C3-C6 cycloalkyl group, a C2-C7 alkanoyl group and a C1-C6 alkylsulfonyl group; $Q^6$ means a single bond or a C1-C6 alkylene group, in which one or two or more methylene groups constituting the C1-C6 alkylene group may be each independently replaced by a sulfinyl group, a sulfonyl group or a carbonyl group.

"A C1-C6 alkyl group, a C2-C7 alkanoyl group or a C1-C6 alkylsulfonyl group, which may have a substituent selected from the group consisting of a halogen atom, a hydroxyl group, a cyano group, a C1-C6 alkoxy group, a C3-C6 cycloalkyl group, a C2-C7 alkanoyl group and a C1-C6 alkylsulfonyl group" for $R^{1k}$ or $R^{1l}$ has the same meanings as the above-mentioned "C1-C6 alkyl group, C2-C7 alkanoyl group or C1-C6 alkylsulfonyl group, which may have a substituent selected from the group consisting of a halogen atom, a hydroxyl group, a cyano group, a C1-C6 alkoxy group, a C3-C6 cycloalkyl group, a C2-C7 alkanoyl group and a C1-C6 alkylsulfonyl group" for $R^{1g}$ or $R^{1h}$ mentioned in the above.

$R^{1k}$ or $R^{1l}$ is preferably a hydrogen atom, or above-mentioned optionally-substituted C1-C6 alkyl group such as a methyl group or a 2,2-difluoroethyl group.

$Q^6$ is preferably a methylene group or an ethylene group.

The group of -$Q^6$-N($R^{1k}$)$R^{1l}$ is preferably a dimethylaminomethylcarbonyl group.

$Q^3$ is preferably a single bond, or a C1-C6 alkylene group such as a methylene group.

Preferred embodiments of the group of -$Q^3$-N($R^{1g}$)$R^{1h}$ include a dimethylamino group, a 2-hydroxyethyl(methyl)amino group, a dimethylaminomethyl group, a 2-(dimethylamino)ethyl group, and a (dimethylaminomethylcarbonyl)amino group. More preferred are a dimethylamino group, a 2-hydroxyethyl(methyl)amino group, or a dimethylaminomethyl group; and even more preferred are a dimethylamino group, and a dimethylaminomethyl group.

The substituent that may be on one or two or more methylene groups constituting the aliphatic ring of the "spiro ring or bicyclo ring" to be formed by $R^{7a}$ and $R^{8a}$, as taken together with the ring atoms to which they bond, is preferably a C1-C6 alkyl group or a group of -$Q^3$-N($R^{1g}$)$R^{1h}$.

Of the group of the formula (a-0):

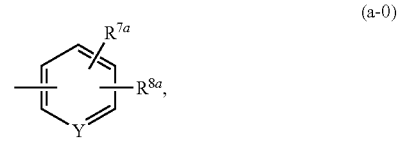

(a-0)

preferred examples of the tricyclic group include, for example, a 2'-methyl-2',3'-dihydro-1'H-spiro[cyclopropan-1,4'-isoquinolin]-7'-yl group, a 3',4'-dihydro-2'H-spiro[cyclopropan-1,1'-isoquinolin]-6'-yl group, a 2'-methyl-3',4'-dihydro-2'H-spiro[cyclopropane-1,1'-isoquinolin]-6'-yl group, a 3',4'-dihydro-2'H-spiro[cyclobutane-1,1'-isoquinolin]-6'-yl group, a 2'-methyl-3',4'-dihydro-2'H-spiro[cyclobutane-1,1'-isoquinolin]-6'-yl group, a 2'-(2-hydroxyethyl)-3',4'-dihydro-2'H-spiro[cyclobutane-1,1'-isoquinolin]-6'-yl group, a 3',4'-dihydro-2'H-spiro[cyclopentane-1,1'-isoquinolin]-6'-yl group, a 2'-methyl-3',4'-dihydro-2'H-spiro[cyclopentane-1,1'-isoquinolin]-6'-yl group; and more preferred is a 2'-methyl-2',3'-dihydro-1'H-spiro[cyclopropane-1,4'-isoquinolin]-7'-yl group.

Preferred examples of $R^1$, $R^2$, $R^3$, $R^4$, $R^5$, $R^6$, $R^{7a}$, $R^{8a}$ and X in the compounds of the general formula (I-0) includes those similar to the preferred examples of $R^1$, $R^2$, $R^3$, $R^4$; $R^5$, $R^6$, $R^7$, $R^8$ and X in the compounds of the general formula (i).

Further, in the compounds of the general formula (I-0), when $R^{7a}$ and $R^{8a}$ form, as taken together with the group of the formula (a) as so mentioned in the above, a tricyclic group, then $R^1$ is preferably a C1-6 alkyl group such as a methyl group, an ethyl group or an isopropyl group, or a C2-C6 alkynyl group such as a 2-propynyl group.

The term "any substitutable position" means a position having a substitutable hydrogen atom on the carbon, nitrogen, oxygen and/or sulfur atoms thereof, in which the substitution at the hydrogen atom is chemically acceptable and gives a stable compound.

The term "any bondable ring atom" means an atom that constitutes a ring, and the bonding of the ring atom to any other atom or atomic group is chemically acceptable and gives a stable compound. In the invention, examples of the other atom or atomic group include, for example, hydrogen atoms and other groups defined by $R^2$, $R^3$, $R^4$, $R^5$, $R^7$ or $R^8$, or the groups of the formulae (c), (c') or (d).

In the compounds of the invention, for example, the "replacing" of the methylene group constituting the C2-C6 alkylene group, for example, by an oxygen atom or a group of —$N(R^{1a})$— is acceptable only when the "replacing" is chemically acceptable and gives a stable compound.

Depending on the type of the substituent therein and on the salt form thereof, the compound of the invention may include stereoisomers and tautomers such as optical isomers, diastereomers and geometric isomers; and the compound of the invention encompasses all such stereoisomers, tautomers and their mixtures.

The invention includes various crystals, amorphous substances, salts, hydrates and solvates of the compounds of the invention.

Further, prodrugs of the compounds of the invention are within the scope of the invention. In general, such prodrugs are functional derivatives of the compounds of the invention that can be readily converted into compounds that are needed by living bodies. Accordingly, in the method of treatment of various diseases in the invention, the term "administration" includes not only the administration of a specific compound but also the administration of a compound which, after administered to patients, can be converted into the specific compound in the living bodies. Conventional methods for selection and production of suitable prodrug derivatives are described, for example, in "Design of Prodrugs", ed. H. Bundgaard, Elsevier, 1985, which is referred to herein and is entirely incorporated herein as a part of the present description. Metabolites of these compounds include active compounds that are produced by putting the compounds of the invention in a biological environment, and are within the scope of the invention.

Examples of the compounds of the general formula (I-0) and their pharmaceutically-acceptable salts are, for example, the following compounds and their pharmaceutically-acceptable salts:

(1) 6'-(2-allyl-6-{[4-(4-methylpiperazin-1-yl)phenyl]amino}-3-oxo-2,3-dihydro-1H-pyrazolo[3,4-d]pyrimidin-1-yl)-2H-1,2'-bipyridin-2-one;

(2) 6'-[2-allyl-6-({4-[(3R)-3-(dimethylamino)pyrrolidin-1-yl]phenyl}amino)-3-oxo-2,3-dihydro-1H-pyrazolo[3,4-d]pyrimidin-1-yl]-2H-1,2'-bipyridin-2-one;

(3) 6'-[2-allyl-6-({4-[(3S)-3-(dimethylamino)pyrrolidin-1-yl]phenyl}amino)-3-oxo-2,3-dihydro-1H-pyrazolo[3,4-d]pyrimidin-1-yl]-2H-1,2'-bipyridin-2-one;

(4) 2-allyl-1-[3-fluoro-5-(2-oxopyridin-1(2H)-yl)phenyl]-6-{[4-(4-methylpiperazin-1-yl)phenyl]amino}-1,2-dihydro-3H-pyrazolo[3,4-d]pyrimidin-3-one, (5) 6'-(2-allyl-6-{[4-(4-methylpiperazin-1-yl)phenyl]amino}-3-oxo-2,3-dihydro-1H-pyrazolo[3,4-d]pyrimidin-1-yl)-5-fluoro-2H-1,2'-bipyridin-2-one, (6) 6'-[2-allyl-6-({4-[(tert-butylamino)methyl]phenyl}amino)-3-oxo-2,3-dihydro-1H-pyrazolo[3,4-d]pyrimidin-1-yl]-2H-1,2'-bipyridin-2-one, (7) 2-allyl-6-{[4-(4-methylpiperazin-1-yl)phenyl]amino}-1-[3-(2-oxopyridin-1(2H)-yl)phenyl]-1,2-dihydro-3H-pyrazolo[3,4-d]pyrimidin-3-one, (8) 2-allyl-6-{[4-(1-methylpiperidin-4-yl)phenyl]amino}-1-[3-(2-oxopyridin-1(2H)-yl)phenyl]-1,2-dihydro-3H-pyrazolo[3,4-d]pyrimidin-3-one, (9) 6'-(2-allyl-6-{[4-(1-methylpiperidin-4-yl)phenyl]amino}-3-oxo-2,3-dihydro-1H-pyrazolo[3,4-d]pyrimidin-1-yl)-2H-1,2'-bipyridin-2-one,

(10) 6'-(2-allyl-6-{[3-(hydroxymethyl)-4-(4-methylpiperazin-1-yl)phenyl]amino}-3-oxo-2,3-dihydro-1H-pyrazolo[3,4-d]pyrimidin-1-yl)-2H-1,2'-bipyridin-2-one,

(11) 6'-(2-allyl-6-{[3-methyl-4-(4-methylpiperazin-1-yl)phenyl]amino}-3-oxo-2,3-dihydro-1H-pyrazolo[3,4-d]pyrimidin-1-yl)-2H-1,2'-bipyridin-2-one,

(12) 6'-(2-allyl-6-{[4-(4-methylpiperazin-1-yl)phenyl]amino}-3-oxo-2,3-dihydro-1H-pyrazolo[3,4-d]pyrimidin-1-yl)-3-methyl-2H-1,2'-bipyridin-2-one,

(13) 6'-(2-allyl-6-{[4-(4-methylpiperazin-1-yl)phenyl]amino}-3-oxo-2,3-dihydro-1H-pyrazolo[3,4-d]pyrimidin-1-yl)-4-methyl-2H-1,2'-bipyridin-2-one,

(14) 6'-(2-allyl-6-{[4-(4-methylpiperazin-1-yl)phenyl]amino}-3-oxo-2,3-dihydro-1H-pyrazolo[3,4-d]pyrimidin-1-yl)-5-methyl-2H-1,2'-bipyridin-2-one,

(15) 6'-(2-allyl-6-{[4-(4-methylpiperazin-1-yl)phenyl]amino}-3-oxo-2,3-dihydro-1H-pyrazolo[3,4-d]pyrimidin-1-yl)-3-methoxy-2H-1,2'-bipyridin-2-one,

(16) 6'-(2-allyl-6-{[4-(4-methylpiperazin-1-yl)phenyl]amino}-3-oxo-2,3-dihydro-1H-pyrazolo[3,4-d]pyrimidin-1-yl)-5-(trifluoromethyl)-2H-1,2'-bipyridin-2-one,

(17) 6'-(2-allyl-6-{[4-(3,3-difluoroazetidin-1-yl)phenyl]amino}-3-oxo-2,3-dihydro-pyrazolo[3,4-d]pyrimidin-1-yl)-2H-1,2'-bipyridin-2-one,

(18) N-(3-{[2-allyl-3-oxo-1-(2-oxo-2H-1,2'-bipyridin-6'-yl)-2,3-dihydro-1H-pyrazolo[3,4-d]pyrimidin-6-yl]amino}phenyl)cyclopropanecarboxamide,

(19) 6'-[2-allyl-6-({4-[3-(dimethylamino)propyl]phenyl}amino)-3-oxo-2,3-dihydro-1H-pyrazolo[3,4-d]pyrimidin-1-yl]-2H-1,2'-bipyridin-2-one,

(20) 6'-[2-allyl-6-({4-[3-(dimethylamino)azetidin-1-yl]phenyl}amino)-3-oxo-2,3-dihydro-1H-pyrazolo[3,4-d]pyrimidin-1-yl]-2H-1,2'-bipyridin-2-one,

(21) 6'-[2-allyl-6-({4-[(diethylamino)methyl]phenyl}amino)-3-oxo-2,3-dihydro-1H-pyrazolo[3,4-d]pyrimidin-1-yl]-2H-1,2'-bipyridin-2-one,

(22) 6'-(2-allyl-3-oxo-6-{[4-(2-oxopyrrolidin-1-yl)phenyl]amino}-2,3-dihydro-1H-pyrazolo[3,4-d]pyrimidin-1-yl)-2H-1,2'-bipyridin-2-one,

(23) 6'-(2-allyl-3-oxo-6-{[4-(2-oxopyridin-1(2H)-yl)phenyl]amino}-2,3-dihydro-1H-pyrazolo[3,4-d]pyrimidin-1-yl)-2H-1,2'-bipyridin-2-one,

(24) 6'-[2-allyl-6-({4-[(2S)-2-(hydroxymethyl)pyrrolidin-1-yl]phenyl}amino)-3-oxo-2,3-dihydro-1H-pyrazolo[3,4-d]pyrimidin-1-yl]-2H-1,2'-bipyridin-2-one,

(25) 6-[2-allyl-6-({4-[(2R)-2-(hydroxymethyl)pyrrolidin-1-yl]phenyl}amino)-3-oxo-2,3-dihydro-1H-pyrazolo[3,4-d]pyrimidin-1-yl]-2H-1,2'-bipyridin-2-one,

(26) 6'-{2-allyl-3-oxo-6-[(2,2,3,3-tetrafluoro-2,3-dihydro-1,4-benzodioxin-6-yl)amino]-2,3-dihydro-1H-pyrazolo[3,4-d]pyrimidin-1-yl}-2H-1,2'-bipyridin-2-one,

(27) 6'-(2-allyl-6-{[3-(1-methylpiperizin-4-yl)phenyl]amino}-3-oxo-2,3-dihydro-1H-pyrazolo[3,4-d]pyrimidin-1-yl)-2H-1,2'-bipyridin-2-one,

(28) 6'-[2-allyl-3-oxo-6-({4-[(2S)-2-(pyrrolidin-1-ylmethyl) pyrrolidin-1-yl]phenyl}amino)-2,3-dihydro-1H-pyrazolo [3,4-d]pyrimidin-1-yl]-2H-1,2'-bipyridin-2-one,

(29) 6'-(2-allyl-6-{[3-(hydroxymethyl)-4-methoxyphenyl] amino}-3-oxo-2,3-dihydro-1H-pyrazolo[3,4-d]pyrimidin-1-yl)-2H-1,2'-bipyridin-2-one,

(30) 6'-{2-allyl-6-[(2-methyl-1,2,3,4-tetrahydroisoquinolin-7-yl)amino]-3-oxo-2,3-dihydro-1H-pyrazolo[3,4-d]pyrimidin-1-yl}-2H-1,2'-bipyridin-2-one,

(31) 6'-[2-allyl-6-({4-[methyl(pyridin-2-ylmethyl)amino] phenyl}amino)-3-oxo-2,3-dihydro-1H-pyrazolo[3,4-d] pyrimidin-1-yl]-2H-1,2'-bipyridin-2-one,

(32) 6'-(2-allyl-6-{[4-(2-methyl-2,7-diazaspiro[3.5]non-7-yl)phenyl]amino}-3-oxo-2,3-dihydro-1H-pyrazolo[3,4-d] pyrimidin-1-yl)-2H-1,2'-bipyridin-2-one,

(33) 6'-(2-allyl-6-{[4-(5-methylhexahydropyrrolo[3,4-b] pyrrol-1(2H)-yl)phenyl]amino}-3-oxo-2,3-dihydro-1H-pyrazolo[3,4-d]pyrimidin-1-yl)-2H-1,2'-bipyridin-2-one,

(34) 6'-(2-allyl-6-{[4-(1-methylhexahydropyrrolo[3,4-b] pyrrol-5(1H)-yl)phenyl]amino}-3-oxo-2,3-dihydro-1H-pyrazolo[3,4-d]pyrimidin-1-yl)-2H-1,2'-bipyridin-2-one,

(35) 6'-[2-allyl-6-({4-[3-(tert-butylamino)pyrrolidin-1-yl] phenyl}amino)-3-oxo-2,3-dihydro-1H-pyrazolo[3,4-d] pyrimidin-1-yl]-2H-1,2'-bipyridin-2-one,

(36) 6'-{2-isopropyl-6-[(2-methyl-1,2,3,4-tetrahydroisoquinolin-7-yl)amino]-3-oxo-2,3-dihydro-1H-pyrazolo[3, 4-d]pyrimidin-1-yl}-2H-1,2'-bipyridin-2-one,

(37) 6'-{2-methyl-6-[(2-methyl-1,2,3,4-tetrahydroisoquinolin-6-yl)amino]-3-oxo-2,3-dihydro-1H-pyrazolo[3,4-d] pyrimidin-1-yl}-2H-1,2'-bipyridin-2-one,

(38) 6'-{2-methyl-6-[(2'-methyl-2',3'-dihydro-1'H-spiro[cyclopropane-1,4'-isoquinolin]-7'-yl)amino]-3-oxo-2,3-dihydro-1H-pyrazolo[3,4-d]pyrimidin-1-yl}-2H-1,2'-bipyridin-2-one,

(39) 6'-{2-isopropyl-6-[(2'-methyl-2',3'-dihydro-1'H-spiro [cyclopropane-1,4'-isoquinolin]-7'-yl)amino]-3-oxo-2,3-dihydro-1H-pyrazolo[3,4-d]pyrimidin-1-yl}-2H-1,2'-bipyridin-2-one,

(40) 6'-{2-isopropyl-3-oxo-6-[(2,4,4-trimethyl-1,2,3,4-tetrahydroisoquinolin-7-yl)amino]-2,3-dihydro-1H-pyrazolo[3,4-d]pyrimidin-1-yl}-2H-1,2'-bipyridin-2-one,

(41) 6'-{2-ethyl-6-[(2'-methyl-2',3'-dihydro-1'H-spiro[cyclopropane-1,4'-isoquinolin-7'-yl)amino]-3-oxo-2,3-dihydro-1H-pyrazolo[3,4-d]pyrimidin-1-yl}-2H-1,2'-bipyridin-2-one, or

(42) 6'-{6-[(2-methyl-1,2,3,4-tetrahydroisoquinolin-7-yl) amino]-3-oxo-2-(2-propynyl)-2,3-dihydro-1H-pyrazolo [3,4-d]pyrimidin-1-yl}-2H-1,2'-bipyridin-2-one.

Of the above-mentioned compounds, more preferred are the following compounds or their pharmaceutically-acceptable salts:

(1) 6'-(2-allyl-6-{[4-(4-methylpiperazin-1-yl)phenyl] amino}-3-oxo-2,3-dihydro-1H-pyrazolo[3,4-d]pyrimidin-1-yl)-2H-1,2'-bipyridin-2-one;

(2) 6'-[2-allyl-6-({4-[(3R)-3-(dimethylamino)pyrrolidin-1-yl]phenyl}amino)-3-oxo-2,3-dihydro-1H-pyrazolo[3,4-d] pyrimidin-1-yl]-2H-1,2'-bipyridin-2-one;

(3) 6'-[2-allyl-6-({4-[(3S)-3-(dimethylamino)pyrrolidin-1-yl]phenyl}amino)-3-oxo-2,3-dihydro-1H-pyrazolo[3,4-d] pyrimidin-1-yl]-2H-1,2'-bipyridin-2-one;

(4) 2-allyl-1-[3-fluoro-5-(2-oxopyridin-1(2H)-yl)phenyl]-6-{[4-(4-methylpiperazin-1-yl)phenyl]amino}-1,2-dihydro-3H-pyrazolo[3,4d]pyrimidin-3-one, (5) 6'-(2-allyl-6-{[4-(4-methylpiperazin-1-yl)phenyl] amino}-3-oxo-2,3-dihydro-1H-pyrazolo[3,4-d]pyrimidin-1-yl)-5-fluoro-2H-1,2'-bipyridin-2-one,

(38) 6'-{2-methyl-6-[(2'-methyl-2',3'-dihydro-1'H-spiro[cyclopropane-1,4'-isoquinolin]-7'-yl)amino]-3-oxo-2,3-dihydro-1H-pyrazolo[3,4-d]pyrimidin-1-yl}-2H-1,2'-bipyridin-2-one,

(39) 6'-{2-isopropyl-6-[(2'-methyl-2',3'-dihydro-1'H-spiro [cyclopropane-1,4'-isoquinolin]-7'-yl)amino]-3-oxo-2,3-dihydro-1H-pyrazolo[3,4-d]pyrimidin-1-yl}-2H-1,2'-bipyridin-2-one, or

(42) 6'-{6-[(2-methyl-1,2,3,4-tetrahydroisoquinolin-7-yl) amino]-3-oxo-2-(2-propynyl)-2,3-dihydro-1H-pyrazolo [3,4-d]pyrimidin-1-yl}-2H-1,2'-bipyridin-2-one.

Methods for producing the compounds of the invention are described below.

Production Method 1

A compound of general formula (II):

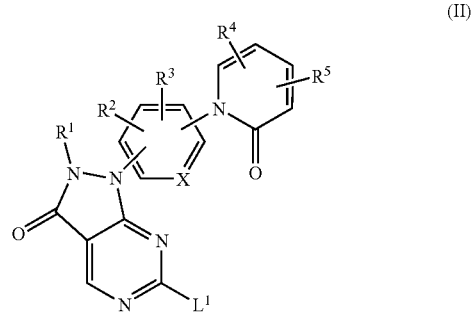

wherein $L^1$ means a leaving group; and $R^1$, $R^2$, $R^3$, $R^4$, $R^5$ and X have the same meanings as above, is reacted with a compound of general formula (III):

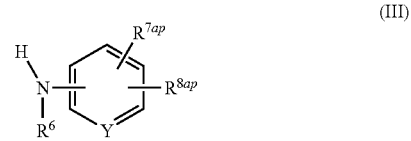

wherein, $R^{7ap}$ means a hydrogen atom, a halogen atom, a C1-C6 alkyl group, a halo-C1-C6 alkyl group, a C1-C6 alkoxy group, an optionally-protected hydroxy-C1-C6 alkyl group or a group of $-Q^2-N(R^{1cp})R^{1dp}$, or means a nitrogen-containing heterocyclic group optionally substituted with a substituent selected from the group consisting of a halogen atom, a C1-C6 alkyl group, an optionally-protected hydroxy-C1-C6 alkyl group, an optionally-protected oxo group and a group of $-Q^1-N(R^{1ap})R^{1bp}$ (wherein the nitrogen-containing heterocyclic group may be protected with an imino-protective group);

$R^{8ap}$ means a hydrogen atom, a halogen atom, a C1-C6 alkyl group, a halo-C1-C6 alkyl group, a C1-C6 alkoxy group or an optionally-protected hydroxy-C1-C6 alkyl group;

or when $R^{7ap}$ and $R^{8ap}$ exist on the ring atoms, adjacent to each other, of the group of the following formula (a):

$R^{7ap}$ and $R^{8ap}$ may form, as taken together, a C2-C6 alkylene group, in which one or two methylene groups constituting the C2-C6 alkylene group may be each independently replaced by an oxygen atom or a group of —N(R$^{1ep}$)—, and the C2-C6 alkylene group may be substituted with a substituent selected from the group consisting of a halogen atom, a C1-C6 alkyl group and a halo-C1-C6 alkyl group; or R$^{7ap}$ and R$^{8ap}$ and the ring atoms to which they bond may be, as taken together, a spiro ring or a bicyclo ring to be formed of a 5-membered to 7-membered aliphatic ring and any other 3-membered to 7-membered aliphatic ring, in which one or two or more methylene groups constituting the spiro ring or the bicyclo ring may be each independently replaced by an oxygen atom, a sulfur atom, a sulfinyl group, a sulfonyl group, a carbonyl group or a group of —N(R$^{1fp}$)—, and the spiro ring or the bicyclo ring may be each independently substituted with a substituent selected from the group consisting of a halogen atom, a hydroxyl group, a C1-C6 alkyl group, a hydroxy-C1-C6 alkyl group or a group of -Q$^3$-N(R$^{1gp}$)R$^{1hp}$;

R$^{1ap}$ and R$^{1bp}$ each independently mean an amino or imino-protective group, a hydrogen atom, a C1-C6 alkyl group or a halo-C1-C6 alkyl group, or, as taken together, they may form a C2-C6 alkylene group, in which the C2-C6 alkylene group may be substituted with a substituent selected from the group consisting of a halogen atom, a C1-C6 alkyl group and a halo-C1-C6 alkyl group;

R$^{1cp}$ and R$^{1dp}$ each independently mean an amino or imino-protective group, or a hydrogen atom, or mean a C1-C6 alkyl group optionally substituted with a substituent selected from the group consisting of a halogen atom, an optionally-protected hydroxyl group, an optionally-protected oxo group, a C3-C6 cycloalkyl group and a nitrogen-containing heterocyclic group (in which the nitrogen-containing heterocyclic group may be protected with an imino-protective group);

R$^{1ep}$ means an imino-protective group, or a hydrogen atom, or means a C1-C6 alkyl group optionally substituted with a substituent selected from the group consisting of a halogen atom, an optionally-protected hydroxyl group, an optionally-protected oxo group, a C3-C6 cycloalkyl group and a nitrogen-containing heterocyclic group (in which the nitrogen-containing heterocyclic group may be protected with an imino-protective group);

R$^{1fp}$ means a hydrogen atom, or means a C1-C6 alkyl group, a C3-C6 cycloalkyl group or a C2-C7 alkanoyl group optionally substituted with a substituent selected from the group consisting of a halogen atom, an optionally-protected hydroxyl group, a cyano group, a C1-C6 alkoxy group, a C3-C6 cycloalkyl group and a C2-C7 alkanoyl group, or means a group of -Q$^4$-Cy of -Q$^5$-N(R$^{1ip}$)R$^{1jp}$;

R$^{1gp}$ and R$^{1hp}$ each independently mean an amino or imino-protective group, or a hydrogen atom, or mean a C1-C6 alkyl group, a C2-C7 alkanoyl group or a C1-C6 alkylsulfonyl group, which may have a substituent selected from the group consisting of a halogen atom, an optionally-protected hydroxyl group, a cyano group, a C1-C6 alkoxy group, a C3-C6 cycloalkyl group, a C2-C7 alkanoyl group and a C1-C6 alkylsulfonyl group, or mean a group of -Q$^6$-N(R$^{1kp}$)R$^{1lp}$;

R$^{1ip}$, R$^{1jp}$, R$^{1kp}$ and R$^{1lp}$ each independently mean an amino or imino-protective group, or a hydrogen atom, or mean a C1-C6 alkyl group, a C2-C7 alkanoyl group or a C1-C6 alkylsulfonyl group, which may have a substituent selected from the group consisting of a halogen atom, an optionally-protected hydroxyl group, a cyano group, a C1-C6 alkoxy group, a C3-C6 cycloalkyl group, a C2-C7 alkanoyl group and a C1-C6 alkylsulfonyl group;

Q$^1$, Q$^2$, Q$^3$, Q$^4$, Q$^5$, Q$^6$, Cy, R$^6$ and Y have the same meanings as above, thereby giving a compound of general formula (IV):

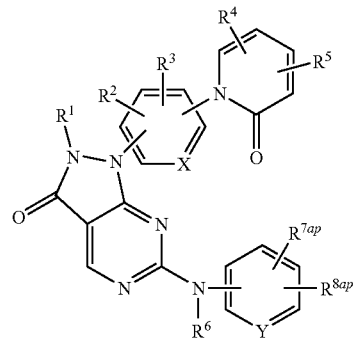

wherein R$^1$, R$^2$, R$^3$, R$^4$, R$^5$, R$^6$, R$^{7ap}$, R$^{8ap}$, x and Y have the same meanings as above, and when the compound (IV) has a protective group of the amino, imino, hydroxyl or oxo group, then the protective group is removed, thereby producing a compound of general formula (I-0):

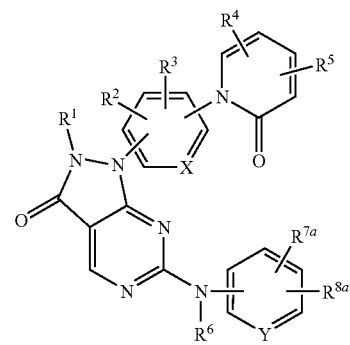

wherein R$^1$, R$^2$, R$^3$, R$^4$, R$^5$, R$^6$, R$^{7a}$, R$^{8a}$, X and Y have the same meanings as above.

The leaving group for L$^1$ includes, for example, a halogen atom such as a chlorine atom, a bromine atom or an iodine atom; an organic sulfonyl group such as a methylsulfonyl group, an ethylsulfonyl group, a phenylsulfonyl group; and an organic sulfonyloxy group such as a methylsulfinyl group, a methylsulfonyloxy group, a trifluoromethylsulfonyloxy group, a p-tolylsulfonyloxy group; and of those, preferred are a chlorine atom, a methylsulfinyl group, a methylsulfonyl group.

The above production method is a general production method for the compounds of the general formula (I-0).

In the above reaction, when the reactants have an amino group, an imino group, a hydroxyl group, an oxo group or the like not participating in the reaction, then the amino group, the imino group, the hydroxyl group and the oxo group may be suitably protected with a protective group for the amino, imino, hydroxyl or oxo group prior to the reaction, and the protective group may be removed after the reaction.

Not specifically defined, "amino or imino-protective group" may be any one having its function. For example, it includes an aralkyl group such as a benzyl group, a p-methoxybenzyl group, a 3,4-dimethoxybenzyl group, an o-nitrobenzyl group, a p-nitrobenzyl group, a benzhydryl group, a trityl group; a lower alkanoyl group such as a formyl group, an acetyl group, a propionyl group, a butyryl group, a pivaloyl group; a benzoyl group; an arylalkanoyl group such as a phenylacetyl group, a phenoxyacetyl group; a lower alkoxycarbonyl group such as a methoxycarbonyl group, an ethoxycarbonyl group, a propyloxycarbonyl group, a tert-butoxycarbonyl group; an aralkyloxycarbonyl group such as a benzyloxycarbonyl group, a p-nitrobenzyloxycarbonyl group, a phenethyloxycarbonyl group; a lower alkylsilyl group such as a trimethylsilyl group, a tert-butyldimethylsilyl group; a tetrahydropyranyl group; a trimethylsilylethoxymethyl group; a lower alkylsulfonyl group such as a methylsulfonyl group, an ethylsulfonyl group; an arylsulfonyl group such as benzenesulfonyl group, a toluenesulfonyl group; and is especially preferably an acetyl group, a benzoyl group, a tert-butoxycarbonyl group, a trimethylsilylethoxymethyl group, a methylsulfonyl group.

Not specifically defined, "hydroxyl-protective group" may be any one having its function. For example, it includes a lower alkyl group such as a methyl group, an ethyl group, a propyl group, an isopropyl group, a tert-butyl group; a lower alkylsilyl group such as a trimethylsilyl group, a tert-butyldimethylsilyl group; a lower alkoxymethyl group such as a methoxymethyl group, a 2-methoxyethoxymethyl group; a tetrahydropyranyl group; a trimethylsilylethoxymethyl group; an aralkyl group such as a benzyl group, a p-methoxybenzyl group, a 2,3-dimethoxybenzyl group, an o-nitrobenzyl group, a p-nitrobenzyl group, a trityl group; an acyl group such as a formyl group, an acetyl group; and is especially preferably a methyl group, a methoxymethyl group, a tetrahydropyranyl group, a trityl group, a trimethylsilylethoxymethyl group, a tert-butyldimethylsilyl group, an acetyl group.

Not specifically defined, "oxo-protective group" may be any one having its function. For example, it includes acetals and ketals such as ethylene ketal, trimethylene ketal, dimethyl ketal.

For the reaction of the compound of the general formula (II) and the compound of the general formula (III), in general, an equimolar or excessive molar amount, preferably from an equimolar amount to 1.5 mols of the compound (III) is used relative to one mol of the compound (II).

The reaction is attained generally in an inert solvent. The inert solvent is, for example, preferably toluene, benzene, methylene chloride, chloroform, tetrahydrofuran, dioxane, dimethylformamide, N-methylpyrrolidone, dimethyl sulfoxide, or their mixed solvent.

Preferably, the reaction is attained in the presence of a base. The base includes, for example, organic bases such as triethylamine, diisopropylethylamine, pyridine, 4-dimethylaminopyridine; and inorganic bases such as sodium hydrogencarbonate, sodium carbonate, potassium carbonate, cesium carbonate, sodium hydroxide, potassium hydroxide.

The amount of the base to be used may be generally from an equimolar amount to an excessive molar amount, preferably from 1 to 3 mols relative to one mol of the compound of the general formula (II).

The reaction temperature may be generally from 0° C. to 200° C., preferably from 20° C. to 150° C.

The reaction time may be generally from 5 minutes to 7 days, preferably from 30 minutes to 24 hours.

After the reaction, the system may be processed in an ordinary manner to obtain a crude product of the compound of the general formula (IV). Thus obtained, the compound of the general formula (IV) is purified in an ordinary manner, or not purified, optionally it is processed for removing the protective group of the amino group, the imino group, the hydroxyl group or the oxo group, if any, in the compound (IV), thereby producing the compound of the general formula (I-0).

In case where the compound of the general formula (IV) does not have a protective group for the amino group, the imino group, the hydroxyl group or the oxo group, the compound of the general formula (IV) substantially means the compound of the general formula (I-0).

The method of removing the protective group varies, depending on the type of the protective group and on the stability of the intended compound (I-0), and may be attained according to methods described in references [see Protective Groups in Organic Synthesis, 3rd. Ed., by T. W. Greene, John Wiley & Sons (1999)] or according to methods similar thereto. For example, herein employable are a method of solvolysis with an acid or a base, which comprises processing the protected compound with from 0.01 mols to a large excessive amount of an acid, preferably trifluoroacetic acid, formic acid or hydrochloric acid, or with from an equimolar amount to a large excessive amount of a base, preferably potassium hydroxide or calcium hydroxide; and a method of chemical reduction with a metal hydride complex, or catalytic reduction with a palladium-carbon catalyst or a Raney nickel catalyst.

The compound of the general formula (I-0) may be readily isolated and purified in any ordinary separation method. Examples of the method are, for example, solvent extraction, recrystallization, column chromatography, preparative thin-layer chromatography.

The compounds may be converted into their pharmaceutically-acceptable salts or esters in an ordinary manner; and on the contrary, their salts or esters may also be converted into free compounds in an ordinary manner.

"Salts" of the compound of the general formula (III) mean ordinary salts used in the field of organic chemistry. For example, when the compound has an acidic heterocyclic group such as a tetrazolyl group, then its salts are base-addition salts at the acidic heterocyclic group; or when the compound has an amino group or a basic heterocyclic group, then its salts are acid-addition salts at the amino group or the basic heterocyclic group.

The base-addition salts include, for example, alkali metal salts such as sodium salts, potassium salts; alkaline earth metal salts such as calcium salts, magnesium salts; ammonium salts; organic amine salts such as trimethylamine salts, triethylamine salts, dicyclohexylamine salts, ethanolamine salts, diethanolamine salts, triethanolamine salts, procaine salts, N,N'-dibenzylethylenediamine salts.

The acid-addition salts include, for example, inorganic acid salts such as hydrochlorides, sulfates, nitrates, phosphates, perchlorates; organic acid salts such as maleates, fumarates, tartrates, citrates, ascorbates, trifluoroacetates; sulfonates such as methanesulfonates, isethionates, benzenesulfonates, p-toluenesulfonates.

The compounds of the general formulae (II) and (III) may be commercially available, or may be produced according to methods described in references [see WO2007/067506, WO2004/104007, Journal of Medicinal Chemistry, Vol. 48, pp. 2371-2387], or according to methods similar to them, or according to the methods described below, or according to the methods described in Examples and Production Examples, optionally as suitably combined.

Production Method A

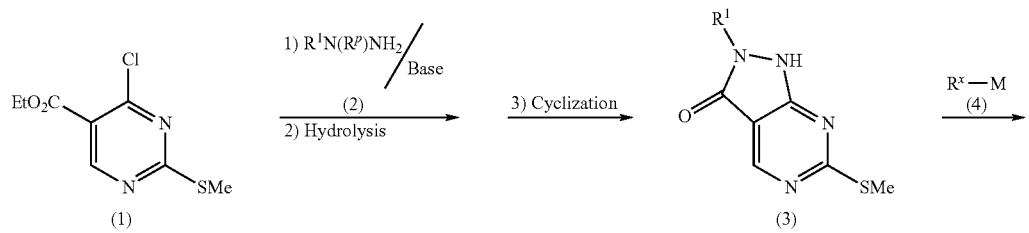

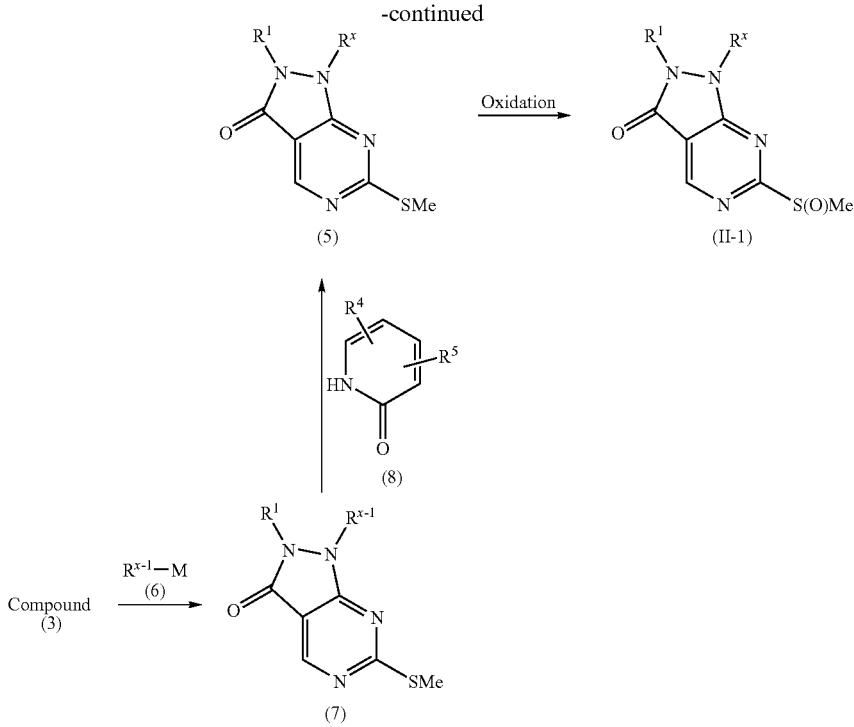

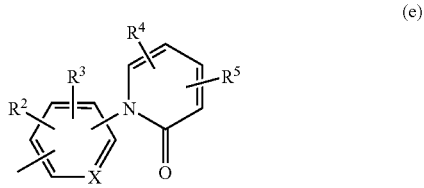

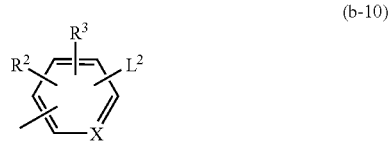

wherein Et means an ethyl group; M means an ordinary organic metal atom; Me means a methyl group;
$R^p$ means a hydrogen atom, or an imino-protective group; Rx means a group of the following formula (e):

(e)

wherein $R^2$, $R^3$, $R^4$; $R^5$ and X have the same meanings as above; $R^{x-1}$ means a group of the following formula (b-10):

(b-10)

wherein $L^2$ means a leaving group; $R^2$, $R^3$ and X have the same meanings as above; $R^1$ has the same meaning as above.

The imino-protective group for $R^p$ is, for example, preferably a benzyl group, a paramethoxybenzyl group, a tert-butoxycarbonyl group, or a benzyloxycarbonyl group.

The production method C is a production method for compounds of the general formula (II) where the leaving group $L^1$ is a methylsulfinyl group, or that is, compounds of the general formula (II-1).

According to this production method, the compound of the general formula (II-1) can be produced by reacting a compound of a formula (1) and a hydrazine compound of a formula (2) in the presence of a base followed, then hydrolyzing and cyclizing the resulting compound to give a compound of a formula (3), and via a step (i) of reacting the compound (3) with an organic metal compound of a formula (4) in the presence of a catalyst to thereby introduce the above-mentioned group $R^x$ thereinto to give a compound (5), or a step (ii) of reacting the compound (3) with an organic metal compound of a formula (6) in the presence of a catalyst to thereby introduce the above group $R^{x-1}$ thereinto to give a compound (7), and then reacting the compound (7) with a compound of a formula (8) to give a compound (5), and finally oxidizing the methylthio group of the compound (5) into a methylsulfinyl group, thereby producing the intended compound.

In the step of reacting the compound of the formula (1) with a hydrazine derivative of the formula (2) in the presence of a base, in general, from 0.5 mols to an excessive molar amount, preferably from an equimolar amount to 1.5 mols of the hydrazine derivative (2) is reacted with one mol of the compound (1).

The reaction is attained generally in the presence of an organic base such as triethylamine, diisopropylethylamine, pyridine, 4-dimethylaminopyridine, or an inorganic base such as sodium hydroxide, potassium hydroxide, sodium carbonate, potassium carbonate, sodium hydrogencarbonate, in an inert solvent such as methylene chloride, chloroform, tetrahydrofuran, ethyl ether, benzene, toluene, dimethylformamide or their mixed solvent.

Preferably, the amount of the base to be used is generally from an equimolar amount to an excessive molar amount relative to 1 mol of the compound (1). In case where the base is a liquid, it may serve both as a solvent and as a base.

The reaction temperature may be generally from −78° C. to 200° C., preferably from 20° C. to 100° C.

The reaction time may be generally from 5 minutes to 7 days, preferably from 8 hours to 24 hours.

To the step of hydrolyzing the compound produced through the above reaction, applicable is carboxylate hydrolysis per-se well known in the field of organic chemistry. In general, the hydrolysis may be attained in a solvent such as methanol, ethanol, tetrahydrofuran, dioxane, water or their mixed solvent, for example, using an acid such as hydrochloric acid or sulfuric acid, or a base such as sodium hydroxide, potassium hydroxide or calcium hydroxide.

The reaction temperature is, in general, preferably from room temperature to the boiling point of the solvent used in the reaction, and the reaction time is, in general, preferably from 1 hour to 48 hours.

After the hydrolysis, the step of producing the compound (3) through cyclization of the resulting compound may be attained as follows: After the hydrolysis, the reaction liquid is acidified and then directly subjected to cyclization as it is, or when the cyclization could not go on, the hydrolyzed compound is heated under reflux in the presence of an acetic anhydride, or the hydrolyzed compound is reacted with thionyl chloride.

In the case of cyclization with acetic anhydride, the amount of acetic anhydride to be used is preferably an excessive molar amount, and the reaction time is, in general, preferably from 1 hour to 48 hours.

In case of reaction with thionyl chloride, the amount of thionyl chloride to be used is preferably an excessive molar amount, and the reaction time is, in general, preferably from 1 hour to 48 hours.

In the step of reacting the compound (3) with an organic metal compound of the formula (4) in the presence of a catalyst to thereby introduce a group of $R^x$ thereinto to give the compound (5), in general, the compound (4) is used in an amount of from 0.5 mols to 5 mols, preferably from 0.7 mols to 3 mols relative to 1 mol of the metal salt catalyst or the metal salt reagent or the compound (3).

For the metal salt catalyst or the metal salt reagent in the reaction, for example, a transition metal generally used in cross-coupling reaction may be used, such as copper, nickel or palladium, for which, for example, preferred are copper (II)acetate, copper trifluoromethanesulfonate, copper iodide.

The general organic metal atom represented by M means an organic metal atom generally used in cross-coupling reaction, including, for example, lithium, boron, silicon, magnesium, aluminium, zinc, tin, more preferably boron, zinc, tin. Concretely, the metal compounds for use herein are boric acid and borates with boron; zinc chloride, zinc bromide or zinc iodide with zinc; and tri-lower alkyltins with tin.

The reaction may be attained generally in an inert solvent. The inert solvent is, for example, preferably water, benzene, toluene, xylene, methylene chloride, chloroform, dimethoxyethane, tetrahydrofuran, dioxane, dimethylformamide, or their mixed solvent.

The reaction temperature may be generally from room temperature to the boiling point of the solvent used in the reaction, preferably from 20° C. to 200° C.

The reaction time may be generally from 30 minutes to 7 days, preferably from 24 hours to 3 days.

Preferably, the reaction is attained in the presence of a base. The base includes, for example, inorganic bases such as potassium phosphate, sodium hydrogencarbonate, sodium carbonate, potassium carbonate, cesium carbonate; organic bases such as triethylamine, diisopropylamine, pyridine.

The amount of the base to be used may be generally from 0.5 to 5 mols, preferably from an equimolar amount to 3 mols, relative to 1 mol of the compound (3).

In the above step, a halide compound having the group of $R^x$ may also be used in place of the organic metal compound of the formula (4). In case where the halide compound is used, the catalyst is preferably a copper(I) iodide/diamine complex.

The step of reacting the compound (3) with an organic metal compound of the formula (6) in the presence of a catalyst to thereby introduce the group of $R^{x-1}$ thereinto to produce the compound (7) may be attained in the same manner as that for the step of reacting the compound (3) with the organic metal compound of the formula (4) in the presence of a catalyst to thereby introduce the group of $R^x$ thereinto to give the compound (5). In this step, a halide compound having the group of $R^{x-1}$ may also be used in place of the organic metal compound of the formula (6), like in the case of using a halide compound having the group of $R^x$ in place of the organic metal compound of the formula (4). In this case, the catalyst is preferably a copper(I) iodide/diamine complex.

The leaving group represented by $L^2$ in $R^{x-1}$ of the formula (b-10) may refer to the examples of the leaving group $L^1$ in the production method 1, and, for example, it is preferably a halogen atom such as a bromine atom.

The step of reacting the compound (7) with a compound of the formula (8) to give a compound (5) may be attained in the same manner as that for the step of reacting the compound (3) with a halide compound having a group of $R^{x-1}$. In this case, the catalyst is preferably a copper(I) iodide/diamine complex, like in the above.

To the step of oxidizing the methylthio group of the compound (5) to thereby produce a compound (II-1), applicable is a method of oxidizing a methylthio group into a methylsulfinyl group or a methylsulfonyl group per-se well known in the field of organic chemistry. In general, for example, from 0.5 mols to an excessive molar amount, preferably from an equimolar amount to 1.5 mols of an oxidizing agent such as metachloroperbenzoic acid or Oxone may be used relative to 1 mol of the compound (5), in an inert solvent such as benzene, toluene, methylene chloride, chloroform, tetrahydrofuran, acetonitrile or dimethylformamide.

The reaction temperature is, in general, preferably from 0° C. to the boiling point of the solvent used in the reaction, and the reaction time is, in general, preferably from 30 minutes to 8 hours.

The compounds of the general formulae (1), (2), (4), (6) and (8) may be commercially available, or may be produced according to known methods or according to the methods described in Examples or according to methods similar to them, optionally as suitably combined.

Pharmacological Test Examples of the compounds of the invention are shown below.

Pharmacological Test 1 (Wee1 Kinase-Inhibitory Effect)

(1) Purification of Wee1 Kinase:

A cDNA of Wee1 kinase with glutathion-S-transferase (GST) fused at the amino terminal thereof was inserted into a baculovirus expression vector to construct a recombinant baculovirus, with which cells of an insect cell line Sf9 were infected for high expression therein. The infected cells were collected and solubilized, and then the GST-tagged Wee1 kinase protein was adsorbed by a glutathion column, and eluted from the column with glutathion, and the active fraction was desalted in a desalting column to give a purified enzyme.

(2) Determination of Wee1 Kinase Activity:

In determination of the Wee1 kinase activity, a synthetic peptide, Poly(Lys,Tyr) Hydrobromide (Lys:Tyr (4:1)) bought from Sigma was used as the substrate.

The amount of the reaction liquid was 21.1 µL; and the composition of the reaction buffer was 50 mM Tris-HCl buffer (pH 7.4)/10 mM magnesium chloride/1 mM dithiothreitol. The purified Wee1 kinase, 2.5 μg of the substrate peptide, 10 μM of non-labeled adenosine triphosphate (ATP) and 1 μCi of [γ-$^{33}$P]-labeled ATP (2500 Ci/mmol or more) were added to it, and reacted at 30° C. for 30 minutes. Next, 10 μL of 350 mM phosphate buffer was added to the reaction system to stop the reaction. The substrate peptide was adsorbed by a P81 paper filter 96-well plate, then washed a few times with 130 mM phosphate buffer, and its radioactivity was counted with a liquid scintillation counter. The [γ-$^{33}$P]-labeled ATP was bought from Amersham Bioscience.

To add a test compound to the reaction system, the compound was diluted with dimethyl sulfoxide (DMSO) to prepare a series of dilutions. 1.1 μL of each dilution was added to the reaction system. As a control, 1.1 μL of DMSO was added to the reaction system.

As in Table 1, the compounds of the invention exhibit an excellent Wee1-inhibitory activity.

TABLE 1

| Compound | Wee1-Inhibitory Effect (IC50, nM) |
|---|---|
| Example 1 | 16 |
| Example 2 | 18 |
| Example 3 | 16 |
| Example 4 | 7.2 |
| Example 5 | 18 |
| Example 8 | 24 |
| Example 9 | 11 |
| Example 11 | 10 |
| Example 17 | 6.9 |
| Example 27 | 6.9 |
| Example 29 | 6.5 |
| Example 30 | 17.9 |
| Example 38 | 12.6 |
| Example 39 | 20.6 |
| Example 42 | 4.4 |

Next, the Cdc2-tyrosine 15-phosphorylation-inhibitory effect in cells of the compounds of the general formula (I-0) of the invention is described below.

Pharmacological Test 2 (Method of Determining Drug Potency with Cells (Cdc2 (Cdk1) Tyrosine 15-Phosphorylation-Inhibitory Effect))

a) Reagents:
Fetal bovine serum (FBS) was gotten from Morgate; media RPMI1640 and DMEM were from Invitrogen; camptothecin was from Sigma; gemcitabine was from Nippon Eli Lilly; nocodazole and protease inhibitor cocktail were from Sigma; rabbit anti-Cdc2 antibody and mouse anti-Cdc2 antibody were from Santa Cruz Biotechnology; rabbit anti-tyrosine 15-phosphorylated Cdc2 antibody and horseradish peroxidase-labeled anti-mouse IgG antibody were from Cell Signaling Technology; sure blue reserve TMB peroxidase substrate was from Kirkegaard and Perry Laboratories.

b) Cells:
Human non-small cell lung cancer cells (NCI-H1299) and human colon cancer cells (WiDr) were gotten from American Type Culture Collection (ATCC).

c) Method of Effect Determination:
In the method of using NCI-H1299 cells, the cells were suspended in a medium of 10% FBS-added RPMI1640, and the cell suspension was applied to a 96-well Nunclondelta-processed plastic plate (bought from Nunc), in an amount of 2000 cells/100 μL/well, in which the cells were incubated overnight in 5% $CO_2$-95% air at 37° C. Camptothecin was dissolved in dimethyl sulfoxide (DMSO), and diluted with a medium of 10% FBS-added RPMI1640, and then this was applied to the plate on which the cells had been previously sowed, in an amount of 50 μL/well in such a manner that the final concentration of camptothecin could be 200 nM. Then, the cells were incubated for 16 hours at 37° C. in 5% $CO_2$-95% air. A test compound was stepwise diluted with DMSO, then diluted with 4000 nM nocodazole-containing, 10% FBS-added RPMI1640, and applied to the plate on which the camptothecin-treated cells had been sowed, in an amount of 50 μL/well. The cells were incubated for 8 hours at 37° C. in 5% $CO_2$-95% air, then the culture was removed, and a cytolytic buffer was added to the plate in an amount of 100 μL/well, shaken at 4° C. for 2 hours, then frozen at −80° C., and thawed to give a cell solution. Cdc2 and tyrosine 15-phosphorylated Cdc2 in the cell solution were determined through enzyme-linked immunosorbent assay (ELISA), and the ratio of tyrosine 15-phosphorylated Cdc2 to Cdc2 was calculated to obtain the 50% phosphorylation-inhibitory concentration of the test compound to the cells ($EC_{50}$, nM). The cytolytic buffer used herein is an aqueous solution containing 20 mM Hepes (pH 7.5), 150 mM sodium chloride, 1 mM disodium ethylenediaminetetraacetate, 0.1% polyoxyethylene (10) octylphenyl ether, 1% protease inhibitor cocktail, 1 mM dithiothreitol, 2 mM sodium orthovanadate, 10 mM sodium fluoride and 10 mM glycerol diphosphate. Cdc2 was determined through ELISA as follows: A rabbit anti-Cdc2 antibody solution, which had been diluted 200-fold with 50 mM carbonate-bicarbonate buffer (pH 9.6), was applied to a 96-well maxisorpimmuno plate (bought from Nunc), in an amount of 50 μL/well, and statically kept overnight at 4° C. so as to fix the antibody on the plate. Next, this was washed three times with phosphate-buffered physiological saline (PBS), and 5% bovine serum albumin-containing PBS (5% BSA/PBS) was added thereto in an amount of 300 μL/well, and statically kept at room temperature for 2 hours, and then again washed three times with PBS. A mouse anti-Cdc2 antibody solution that had been diluted 100-fold with 0.05% polyoxyethylene sorbitan monolaurate and 1% BSA-containing Tris-HCl-buffered physiological saline (1% BSA/TBS-T) was added to it in an amount of 50 μL/well, and the cell solution was added thereto in an amount of 5 μL/well and statically kept overnight at 4° C. Next, this was washed three times with 0.05% polyoxyethylene sorbitan monolaurate and 0.1% BSA-containing Tris-HCl-buffered physiological saline (0.1% BSA/TBS-T), and then a horseradish peroxidase-labeled anti-mouse IgG antibody solution that had been diluted 2000-fold with 1% BSA/TBS-T was added thereto in an amount of 70 μL/well, and statically kept at room temperature for 3 hours. Finally, this was washed five times with 0.1% BSA/TBS-T, then a substrate of sure blue reserve TMB peroxidase was added to it in an amount of 100 μL/well, and left for coloration in a dark place at room temperature for 15 minutes. Then, 1 M hydrochloric acid was added to it in an amount of 100 μL/well to stop the reaction, and this was analyzed through colorimetry. Tyrosine 15-phosphorylated Cdc2 was determined through ELISA as follows: A rabbit anti-tyrosine 15-phosphorylated Cdc2 antibody solution, which had been diluted 100-fold with 50 mM carbonate-bicarbonate buffer (pH 9.6), was applied to a 96-well maxisorpimmuno plate in an amount of 50 μL/well, and statically kept overnight at 4° C. so as to fix the antibody on the plate. Next, this was washed three times with PBS, and 5% BSA/PBS was added thereto in an amount of 300 μL/well, and statically kept at room temperature for 2 hours, and then again washed three times with PBS. A mouse anti-Cdc2 antibody solution that had been diluted 100-fold with 1% BSA/TBS-T was added to it in an amount of 50 μL/well, and the cell solution was added thereto in an amount of 5 μL/well and statically kept overnight at 4° C. Next, this was washed three times with 0.1% BSA/TBS-T, and then a horseradish peroxidase-labeled anti-mouse IgG antibody solution that had been diluted 2000-fold with 1% BSA/TBS-T was added thereto in an amount of 70 μL/well, and statically kept at room temperature for 3 hours. Finally, this was washed five times with 0.1% BSA/TBS-T, then a substrate of sure blue reserve TMB peroxidase was added to it in an amount of 100 μL/well, and left for coloration in a dark place at room temperature for 5 minutes. Then, 1 M hydrochloric acid was added to it in an amount of 100 μL/well to stop the reaction, and this was analyzed through colorimetry.

In the method of using WiDr cells, the cells were suspended in a medium of 10% FBS-added DMEM, and the cell suspension was applied to a 96-well Nunclondelta-processed plastic plate in an amount of 2000 cells/100 μL/well, in which the cells were incubated overnight in 5% $CO_2$-95% air at 37° C. Gemcitabine was dissolved in PBS, and diluted with a medium of 10% FBS-added DMEM, and then this was applied to the plate on which the cells had been previously sowed, in an amount of 50 μL/well in such a manner that the final concentration of gemcitabine could be 100 nM. Then, the cells were incubated for 24 hours at 37° C. in 5% $CO_2$-95% air. A test compound was stepwise diluted with DMSO, then diluted with 1200 nM nocodazole-containing, 10% FBS-added DMEM, and applied to the plate on which the treated-treated cells had been sowed, in an amount of 50 μL/well. The cells were incubated for 8 hours at 37° C. in 5% $CO_2$-95% air, then the culture was removed, and a cytolytic buffer was added to the plate in an amount of 100 μL/well, shaken at 4° C. for 2 hours, then frozen at −80° C., and thawed to give a cell solution. Cdc2 and tyrosine 15-phosphorylated Cdc2 in the cell solution were determined through ELISA, and the ratio of tyrosine 15-phosphorylated Cdc2 to Cdc2 was calculated to obtain the 50% phosphorylation-inhibitory concentration of the test compound to the cells ($EC_{50}$, nM). Cdc2 was determined through ELISA as follows: A rabbit anti-Cdc2 antibody solution, which had been diluted 200-fold with 50 mM carbonate-bicarbonate buffer (pH 9.6), was applied to a 96-well maxisorp plastic plate in an amount of 50 μL/well, and statically kept overnight at 4° C. so as to fix the antibody on the plate. Next, this was washed three times with PBS, and 5% BSA/PBS was added thereto in an amount of 300 μL/well, and statically kept at room temperature for 2 hours, and then again washed three times with PBS. A mouse anti-Cdc2 antibody solution that had been diluted 100-fold with 1% BSA/TBS-T was added to it in an amount of 50 μL/well, and the cell solution was added thereto in an amount of 10 μL/well and statically kept overnight at 4° C. Next, this was washed three times with 0.1% BSA/TBS-T, and then a horseradish peroxidase-labeled anti-mouse IgG antibody solution that had been diluted 2000-fold with 1% BSA/TBS-T was added thereto in an amount of 70 μL/well, and statically kept at room temperature for 3 hours. Finally, this was washed five times with 0.1% BSA/TBS-T, then a substrate of sure blue reserve TMB peroxidase was added to it in an amount of 100 μL/well, and left for coloration in a dark place at room temperature for 15 minutes. Then, 1 M hydrochloric acid was added to it in an amount of 100 μL/well to stop the reaction, and this was analyzed through colorimetry. Tyrosine 15-phosphorylated Cdc2 was determined through ELISA as follows: A rabbit anti-tyrosine 15-phosphorylated Cdc2 antibody solution, which had been diluted 100-fold with 50 mM carbonate-bicarbonate buffer (pH 9.6), was applied to a 96-well maxisorp plastic plate in an amount of 50 μL/well, and statically kept overnight at 4° C. so as to fix the antibody on the plate. Next, this was washed three times with PBS, and 5% BSA/PBS was added thereto in an amount of 300 μL/well, and statically kept at room temperature for 2 hours, and then again washed three times with PBS. A mouse anti-Cdc2 antibody solution that had been diluted 100-fold with 1% BSA/TBS-T was added to it in an amount of 50 μL/well, and the cell solution was added thereto in an amount of 10 μL/well and statically kept overnight at 4° C. Next, this was washed three times with 0.1% BSA/TBS-T, and then a horseradish peroxidase-labeled anti-mouse IgG antibody solution that had been diluted 2000-fold with 1% BSA/TBS-T was added thereto in an amount of 70 μL/well, and statically kept at room temperature for 3 hours. Finally, this was washed five times with 0.1% BSA/TBS-T, then a substrate of sure blue reserve TMB peroxidase was added to it in an amount of 100 μL/well, and left for coloration in a dark place at room temperature for 10 minutes. Then, 1 M hydrochloric acid was added to it in an amount of 100 μL/well to stop the reaction, and this was analyzed through colorimetry.

As in Table 2 and Table 3, the compounds of the invention exhibit an excellent Cdc2-tyrosine 15 phosphorylation-inhibitory effect to human-derived cancer cells (NCI-H1299 and WiDr).

TABLE 2

| Compound | Cdc2-Y15 Phosphorylation-Inhibitory Effect (H1299, +camptothecin) (EC50, nM) |
|---|---|
| Example 1 | 190 |
| Example 5 | 260 |
| Example 30 | 180 |

TABLE 3

| Compound | Cdc2-Y15 Phosphorylation-Inhibitory Effect (WiDr, +gemcitabine) (EC50, nM) |
|---|---|
| Example 2 | 110 |
| Example 4 | 86 |
| Example 8 | 170 |
| Example 11 | 92 |

The checkpoint-escape effect in cells of the compounds of the general formula (I-0) of the invention is described below.
Pharmacological Test 3 (Method of Determining Drug Potency with Cells (Checkpoint-Escape Effect))
a) Reagents:

Fetal bovine serum (FBS) is gotten from Morgate; a medium of DMEM is from Invitrogen; gemcitabine is from Nippon Eli Lilly; nocodazole and 4',6-diamidino-2-phenylindole are from Sigma; rabbit anti-phosphorylated histone H3 antibody is from Upstate; and fluorescence-labeled (Alexa Fluor 488) anti-rabbit IgG antibody is from Molecular Probe.
b) Cells:

Human colon cancer cells (WiDr) are gotten from American Type Culture Collection (ATCC).
c) Method of Effect Determination:

The cells are suspended in a medium of 10% FBS-added DMEM, and the cell suspension is applied to a poly-D-lysine-coated 96-well plastic plate (bought from Becton Dickinson) in an amount of 2000 cells/100 μL/well, in which the cells are incubated overnight in 5% $CO_2$-95% air at 37° C. Gemcitabine is dissolved in phosphate-buffered saline (PBS), and diluted with a medium of 10% FBS-added DMEM, and then this is applied to the plate on which the cells have been previously sowed, in an amount of 50 μL/well in such a manner that the final concentration of gemcitabine could be 100 nM. Then, the cells are incubated for 24 hours at 37° C. in 5% $CO_2$-95% air. A test compound is stepwise diluted with dimethyl sulfoxide, then diluted with 1200 nM nocodazole-containing, 10% FBS-added DMEM, and applied to the plate on which the gemcitabine-treated cells have been sowed, in an amount of 50 μL/well. The cells are incubated for 8 hours at 37° C. in 5% $CO_2$-95% air, then the culture is removed, and methanol that have been cooled to −20° C. is added to it in an amount of 100 μL/well. Then, the plate is kept overnight at −20° C. so as to fix the cells thereon. Next, the methanol-fixed cells are washed with PBS, and 1% bovine serum albumin-containing PBS (1% BSA/BPS) is added to it in an amount of 50 μL/well, and statically kept at room temperature for 30 minutes, and then rabbit anti-phosphorylated histone H3 antibody that has been diluted 250-fold with 1% BSA/PBS is added thereto in an amount of 50 μL/well, and statically kept at room temperature for 90 minutes. Next, this is washed with PBS, and a solution containing 4',6-diamidino-2-phenylindole that has been diluted with 1% BSA/PBS to have a concentration 10 μg/mL and a fluorescence-labeled (Alexa Fluor 488) anti-rabbit IgG antibody that has been diluted 250-fold is added to it in an amount 50 μL/well, and reacted in a dark place at room temperature for 60 minutes. Finally, this is washed with PBS, and its fluorescence intensity is determined to calculate the ratio of the phosphorylated histone H3-positive cells (cells that have been in a cell division cycle through removal of checkpoint). From this, obtained is the 50% checkpoint escape concentration to the cells of the test compound ($EC_{50}$, nM).

The above confirms the excellent checkpoint escape effect to human-derived cancer cells (WiDr) of the compound of the invention.

Pharmacological Test 4 (Tumor Growth Inhibitory Effect)

Human colon cancer cells (WiDr, gotten from ATCC) are implanted under the skin of the back of an F344/N Jcl-rnu nude rat. 12 days after the implantation, 5 mg/kg of gemcitabine (Gemzar, from Eli Lily) is intravenously administered to it; and after 24 hours, a test compound suspended in a solvent (0.5% methyl cellulose) is orally administered thereto. This is repeated once a week for 3 weeks. The tumor volume (0.5×major diameter×minor $diameter^2$) is measured on days 0, 3, 6, 10, 13, 17, 20, 24 and 27 (the first gemcitabine administration is on day 0). The relative tumor volume is calculated, based on the tumor volume on day 0, as 1. The tumor growth rate (% T/C) is obtained according to the formulae mentioned below.

In case where the tumor volume change from day 0 in the test compound administration group is more than 0 (>0):

% T/C=(tumor volume change in the test compound group on days 3, 6, 10, 13, 17, 20, 24 and 27/ tumor volume change in the control group on days 3, 6, 10, 13, 17, 20, 24 and 27)×100.

In case where the tumor volume change from day 0 in the test compound administration group is less than 0 (<0):

% T/C=(tumor volume change in the test compound group on days 3, 6, 10, 13, 17, 20, 24 and 27/ tumor volume change in the test compound group on day 0)×100.

The above confirms that the compounds of the invention, as combined with any other anticancer agent, enhance the anticancer effect of the other anticancer agent.

Pharmacological Test 5 (Method of Determining Drug Potency with Cells (Radiation (X Ray)-Sensitizing Effect))

a) Reagents:

Fetal bovine serum (FBS) is gotten from Morgate; RPMI1640 medium and 0.25% trypsin EDTA are from Invitrogen; cycle test plus DNA regent kit is from Becton Dickinson); and nylon net filter is from Millipore.

b) Cells:

Human non-small cell lung cancer cells (NCI-H1299) are gotten from ATCC.

c) Method of Effect Determination:

NCI-H1299 cells are suspended in a medium of 10% FBS-added RPMI1640, and the cell suspension is applied to a 6-well Nunclondelta-processed plastic plate (bought from Nunc), in an amount of 100000 cells/2 mL/well, in which the cells are incubated overnight in 5% $CO_2$-95% air at 37° C. Using Softex's M-150WE, the cells are irradiated with 5000 R X-ray, and then incubated in 5% $CO_2$-95% air at 37° C. for 16 hours. A test compound is stepwise diluted with DMSO, and applied to the plate on which the X-ray-treated cells have been sowed, in an amount of 2 μL/well. The cells are incubated for 8 hours at 37° C. in 5% $CO_2$-95% air, then the culture is sampled. The cells having remained on the plate are mixed with 0.25% trypsin added thereto in an amount of 600 μL/well, and then statically kept at room temperature to be a cell suspension. The cell suspension and the previously-sampled culture are mixed, then centrifuged, and the supernatant is removed thereby finishing the sampling operation. The sample is suspended in 1 mL of a buffer of the cycle test plus DNA regent kit, and frozen and stored at −80° C. The stored sample is thawed on a test day, then centrifuged to remove the supernatant, and this is suspended in 250 μL of the solution A of the cycle test plus kit, then statically left at room temperature for 10 minutes, and then 150 μL of the solution B is added thereto, and further statistically kept at room temperature for 10 minutes. Next, 150 μL of the solution C is added to it, statically kept at 4° C. for 10 minutes, and then filtered through the nylon net filter, thereby finishing the DNA coloration. Using Becton Dickinson's FACS Calibur, the DNA amount of the cell is quantified according to a FACS method, and the ratio of the cells with DNA fragmentation is determined.

As in the above, the excellent DNA fragmentation-inducing effect of the compounds of the invention to the human-derived cancer cells (NCI-H1299) can be determined, and the X-ray-sensitizing effect of the compounds of the invention can be thereby determined.

The compounds of the general formula (I-0) can be administered orally or parenterally, and after formulated into preparations suitable to such administration modes, the compounds can be used as pharmaceutical compositions and anticancer agents.

The term "cancer" as referred to in this description includes various sarcoma and carcinoma and includes solid cancer and hematopoietic cancer. The solid cancer as referred to herein includes, for example, brain tumor, cervicocerebral cancer, esophageal cancer, thyroid cancer, small cell cancer, non-small cell cancer, breast cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' tumor, skin cancer, malignant melanoma, neuroblastoma, osteosarcoma, Ewing's tumor, soft part sarcoma. On the other hand, the hematopoietic cancer includes, for example, acute leukemia, chronic lymphatic leukemia, chronic myelocytic leukemia, polycythemia vera, malignant lymphoma, multiple myeloma, Hodgkin's lymphoma, non-Hodgkin's lymphoma.

The term "treatment of cancer" as referred to in this description means that an anticancer agent is administered to a cancer case so as to inhibit the growth of the cancer cells in the case. Preferably, the treatment results in cancer growth regression, or that is, it reduces the size of a detectable cancer. More preferably, the treatment results in complete disappearance of cancer.

The cancer for which the therapeutical effect of the compounds of the invention is favorably expected includes, for example, human solid cancer. The human solid cancer includes, for example, brain cancer, cervicocerebral cancer, esophageal cancer, thyroid cancer, small cell cancer, non-small cell cancer, breast cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' cancer, skin cancer, malignant melanoma, neuroblastoma, osteosarcoma, Ewing's tumor, soft part sarcoma, acute leukemia, chronic lymphatic leukemia, chronic myelocytic leukemia, Hodgkin's lymphoma.

The pharmaceutical composition and the anticancer agent of the invention may contain a pharmaceutically-acceptable carrier or diluent. Here, the "pharmaceutically-acceptable carrier or diluent" refers to excipients [e.g., fats, beeswax, semi-solid and liquid polyols, natural or hardened oils]; water (e.g., distilled water, particularly distilled water for injection), physiological saline, alcohols (e.g., ethanol), glycerol, polyols, aqueous glucose solution, mannitol, plant oils; additives [e.g., extending agent, disintegrating agent, binder, lubricant, wetting agent, stabilizer, emulsifier, dispersant, preservative, sweetener, colorant, seasoning agent or aromatizer, thickener, diluent, buffer substance, solvent or solubilizing agent, chemical for achieving storage effect, salt for modifying osmotic pressure, coating agent or antioxidant}.

Various preparation forms can be selected for the pharmaceutical composition and the anticancer agent of the invention, and examples thereof include oral preparations such as tablets, capsules, powders, granules or liquids, or sterilized liquid parenteral preparations such as solutions or suspensions, as well as suppositories and ointments.

Solid preparations can be prepared in the form of tablet, capsule, granule and powder without any additives, or prepared using appropriate carriers (additives). Examples of such carriers (additives) may include saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; fatty acid salts such as calcium stearate or magnesium stearate; alcohols such as stearyl alcohol or benzyl alcohol; synthetic cellulose derivatives such as methyl cellulose, carboxymethylcellulose, ethyl cellulose or hydroxypropylmethyl cellulose; and other conventionally used additives such as gelatin, talc, plant oil and gum arabic.

These solid preparations such as tablets, capsules, granules and powders may generally contain, for example, from 0.1 to 100% by weight, and preferably from 5 to 98% by weight, of the compound of the above general formula (I-0) as the active ingredient thereof, based on the total weight of the preparation.

Liquid preparations are produced in the form of suspension, syrup, injection and drip infusion (intravenous fluid) using appropriate additives that are conventionally used in liquid preparations, such as water, alcohols or plant-derived oils such as soybean oil, peanut oil and sesame oil.

In particular, when the preparation is administered parenterally in a form of intramuscular injection, intravenous injection or subcutaneous injection, an appropriate solvent or diluent may be exemplified by distilled water for injection, an aqueous solution of lidocaine hydrochloride (for intramuscular injection), physiological saline, aqueous glucose solution, ethanol, polyethylene glycol, propylene glycol, liquid for intravenous injection (e.g., an aqueous solution of citric acid or sodium citrate) or an electrolytic solution (for intravenous drip infusion and intravenous injection), or a mixed solution thereof.

Such injection may be in a form of a preliminarily dissolved solution, or in a form of powder per se or powder associated with a suitable carrier (additive) which is dissolved at the time of use. The injection liquid may contain, for example, from 0.1 to 10% by weight of the active ingredient based on the total weight of the preparation.

Liquid preparations such as suspension or syrup for oral administration may contain, for example, from 0.1 to 10% by weight of the active ingredient based on the total weight of the preparation.

The preparations can be prepared by a person having ordinary skill in the art according to conventional methods or common techniques. For example, oral preparations can be prepared by mixing a suitable amount of a compound of the invention and a suitable amount of lactose and encapsulating the resulting mixture in hard gelatin capsules suitable to oral administration. On the other hand, injection preparations containing a compound of the invention can be prepared, for example, by mixing a suitable amount of a compound of the invention with a suitable amount of 0.9% physiological saline, and filling the resulting mixture in vials for injection.

As combined with various other agents useful for cancer treatment, or as combined with radiation therapy, the compounds of the invention can be used. The individual ingredients of such combinations may be administered at different times or at the same time during the treatment period, as divided preparations or as a single preparation. Accordingly, the invention should be interpreted to include all administration modes to be taken at the same time or at different times, and the administration as referred to in the invention should be interpreted as such. The range of the combination of the compound of the invention and other agents useful for treatment of the above-mentioned disorders shall include, in principle, all combinations with any and every pharmaceutical preparation useful for the treatment of the above-mentioned disorders.

Radiation therapy itself means an ordinary method in the field of cancer treatment. In radiation therapy, usable are various radiations and heat sources such as X-ray, γ-ray, neutron ray, electron ray, proton beam. Most ordinary radiation therapy is assisted with an external radiation, e.g., γ-ray from a linear accelerator.

As combined with radiation therapy, the compounds of the invention are effective for enhancing the therapeutical effect in the radiation therapy, and therefore, the compounds are useful as a radiation sensitizer in the field of cancer treatment.

As another aspect of the invention, the compounds are useful as a sensitizer for other anticancer agents in the field of cancer treatment.

As combined with radiation therapy, and/or as combined with any other anticancer agent mentioned below, the compounds of the invention can be used.

"Sensitizer" for radiations or anticancer agents as referred to herein means a medical agent, which enhances, when used in radiation therapy and/or in chemotherapy as combined with anticancer agent, additively or synergistically the therapeutical effect in the radiation therapy and/or the chemotherapy.

The individual preparations in the combined preparations of the invention may have various forms, and they may be prepared in the same manner as that for the above-mentioned preparations. Also, the combined preparations comprising the compound of the invention and some other anticancer agent can be readily prepared by those skilled in the art according to ordinary methods or conventional techniques.

The above-mentioned combination encompasses not only a combination of the composition of the invention as combined with one other active ingredient but also a combination thereof as combined with two or more other active ingredients, There exist many examples of the combinations of the composition of the invention as combined with one or two or more active ingredients selected from therapeutical pharmaceuticals for the above-mentioned disorders.

The agents to be combined with the compositions include, for example, an anticancer agent selected from the group consisting of anticancer alkylating agents, anticancer antimetabolites, anticancer antibiotics, plant-derived anticancer agents, anticancer platinum coordination compounds, anticancer camptothecin derivatives, anticancer tyrosine kinase inhibitors, monoclonal antibodies, interferons, biological response modifiers and other anticancer agents as well as pharmaceutically acceptable salt(s) or ester(s) thereof.

The term "anticancer alkylating agent" as used in the present specification refers to an alkylating agent having anticancer activity, and the term "alkylating agent" herein generally refers to an agent giving an alkyl group in the alkylation reaction in which a hydrogen atom of an organic compound is substituted with an alkyl group. The term "anticancer alkylating agent" may be exemplified by nitrogen mustard N-oxide, cyclophosphamide, ifosfamide, melphalan, busulfan, mitobronitol, carboquone, thiotepa, ranimustine, nimustine, temozolomide or carmustine.

The term "anticancer antimetabolite" as used in the specification refers to an antimetabolite having anticancer activity, and the term "antimetabolite" herein includes, in a broad sense, substances which disturb normal metabolism and substances which inhibit the electron transfer system to prevent the production of energy-rich intermediates, due to their structural or functional similarities to metabolites that are important for living organisms (such as vitamins, coenzymes, amino acids and saccharides). The term "anticancer antimetabolites" may be exemplified methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine or pemetrexed disodium, and preferred are cytarabine, gemcitabine and the like.

The term "anticancer antibiotic" as used in the specification refers to an antibiotic having anticancer activity, and the "antibiotic" herein includes substances that are produced by microorganisms and inhibit cell growth and other functions of microorganisms and of other living organisms. The term "anticancer antibiotic" may be exemplified by actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus or valrubicin, and preferred are doxorubicin, mitomycin C and the like.

The term "plant-derived anticancer agent" as used in the specification includes compounds having anticancer activities which originate from plants, or compounds prepared by applying chemical modification to the foregoing compounds. The term "plant-derived anticancer agent" may be exemplified by vincristine, vinblastine, vindesine, etoposide, sobuzoxane, docetaxel, paclitaxel and vinorelbine, and preferred are etoposide and the like.

The term "anticancer camptothecin derivative" as used in the specification refers to compounds that are structurally related to camptothecin and inhibit cancer cell growth, including camptothecin per se. The term "anticancer camptothecin derivative" is not particularly limited to, but may be exemplified by, camptothecin, 10-hydroxycamptothecin, topotecan, irinotecan or 9-aminocamptothecin, with camptothecin being preferred. Further, irinotecan is metabolized in vivo and exhibits anticancer effect as SN-38. The action mechanism and the activity of the camptothecin derivatives are believed to be virtually the same as those of camptothecin (e.g., Nitta, et al., *Gan to Kagaku Ryoho,* 14, 850-857 (1987)).

The term "anticancer platinum coordination compound" as used in the specification refers to a platinum coordination compound having anticancer activity, and the term "platinum coordination compound" herein refers to a platinum coordination compound which provides platinum in ion form. Preferred platinum compounds include cisplatin; cis-diamminediaquoplatinum (II)-ion; chloro(diethylenetriamine)-platinum (II) chloride; dichloro(ethylenediamine)-platinum (II); diammine(1,1-cyclobutanedicarboxylato)platinum (II) (carboplatin); spiroplatin; iproplatin; diammine(2-ethylmalonato)platinum (II); ethylenediaminemalonatoplatinum (II); aqua(1,2-diaminodicyclohexane)sulfatoplatinum (II); aqua (1,2-diaminodicyclohexane)malonatoplatinum (II); (1,2-diaminocyclohexane)malonatoplatinum (II); (4-carboxyphthalato)(1,2-diaminocyclohexane)platinum (II); (1,2-diaminocyclohexane)-(isocitrato)platinum (II); (1,2-diaminocyclohexane)oxalatoplatinum (II); ormaplatin; tetraplatin; carboplatin, nedaplatin and oxaliplatin, and preferred is carboplatin or cisplatin. Further, other anticancer platinum coordination compounds mentioned in the specification are known and are commercially available and/or producible by a person having ordinary skill in the art by conventional techniques.

The term "anticancer tyrosine kinase inhibitor" as used in the specification refers to a tyrosine kinase inhibitor having anticancer activity, and the term "tyrosine kinase inhibitor" herein refers to a chemical substance inhibiting "tyrosine kinase" which transfers a $\gamma$-phosphate group of ATP to a hydroxyl group of a specific tyrosine in protein. The term "anticancer tyrosine kinase inhibitor" may be exemplified by gefitinib, imatinib or erlotinib.

The term "monoclonal antibody" as used in the specification, which is also known as single clonal antibody, refers to an antibody produced by a monoclonal antibody-producing cell, and examples thereof include cetuximab, bevacizumab, rituximab, alemtuzumab and trastuzumab.

The term "interferon" as used in the specification refers to an interferon having anticancer activity, and it is a glycoprotein having a molecular weight of about 20,000 which is produced and secreted by most animal cells upon viral infection. It has not only the effect of inhibiting viral growth but also various immune effector mechanisms including inhibition of growth of cells (in particular, tumor cells) and enhancement of the natural killer cell activity, thus being designated as one type of cytokine. Examples of "interferon" include interferon $\alpha$, interferon $\alpha$-2a, interferon $\alpha$-2b, interferon $\beta$, interferon $\gamma$-1a and interferon $\gamma$-n1.

The term "biological response modifier" as used in the specification is the so-called biological response modifier or BRM and is generally the generic term for substances or drugs for modifying the defense mechanisms of living organisms or biological responses such as survival, growth or differentiation of tissue cells in order to direct them to be useful for an individual against tumor, infection or other diseases. Examples of the "biological response modifier" include krestin, lentinan, sizofiran, picibanil and ubenimex.

The term "other anticancer agent" as used in the specification refers to an anticancer agent which does not belong to any of the above-described agents having anticancer activities. Examples of the "other anticancer agent" include mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, and goserelin.

The above-described terms "anticancer alkylating agent", "anticancer antimetabolite", "anticancer antibiotic", "plant-derived anticancer agent", "anticancer platinum coordination compound", "anticancer camptothecin derivative", "anticancer tyrosine kinase inhibitor", "monoclonal antibody", "interferon", "biological response modifier" and "other anticancer agent" are all known and are either commercially available or producible by a person skilled in the art by methods known per se or by well-known or conventional methods. The process for preparation of gefitinib is described, for example, in U.S. Pat. No. 5,770,599; the process for preparation of cetuximab is described, for example, in WO 96/40210; the process for preparation of bevacizumab is described, for example, in WO 94/10202; the process for preparation of oxaliplatin is described, for example, in U.S. Pat. Nos. 5,420,319 and 5,959,133; the process for preparation of gemcitabine is described, for example, in U.S. Pat. Nos. 5,434,254 and 5,223,608; and the process for preparation of camptothecin is described in U.S. Pat. Nos. 5,162,532, 5,247,089, 5,191,082, 5,200,524, 5,243,050 and 5,321,140; the process for preparation of irinotecan is described, for example, in U.S. Pat. No. 4,604,463; the process for preparation of topotecan is described, for example, in U.S. Pat. No. 5,734,056; the process for preparation of temozolomide is described, for example, in JP-B No. 4-5029; and the process for preparation of rituximab is described, for example, in JP-W No. 2-503143.

The above-mentioned anticancer alkylating agents are commercially available, as exemplified by the following: nitrogen mustard N-oxide from Mitsubishi Pharma Corp. as Nitromin (tradename); cyclophosphamide from Shionogi & Co., Ltd. as Endoxan (tradename); ifosfamide from Shionogi & Co., Ltd. as Ifomide (tradename); melphalan from GlaxoSmithKline Corp. as Alkeran (tradename); busulfan from Takeda Pharmaceutical Co., Ltd. as Mablin (tradename); mitobronitol from Kyorin Pharmaceutical Co., Ltd. as Myebrol (tradename); carboquone from Sankyo Co., Ltd. as Esquinon (tradename); thiotepa from Sumitomo Pharmaceutical Co., Ltd. as Tespamin (tradename); ranimustine from Mitsubishi Pharma Corp. as Cymerin (tradename); nimustine from Sankyo Co., Ltd. as Nidran (tradename); temozolomide from Schering Corp. as Temodar (tradename); and carmustine from Guilford Pharmaceuticals Inc. as Gliadel Wafer (tradename).

The above-mentioned anticancer antimetabolites are commercially available, as exemplified by the following: methotrexate from Takeda Pharmaceutical Co., Ltd. as Methotrexate (tradename); 6-mercaptopurine riboside from Aventis Corp. as Thioinosine (tradename); mercaptopurine from Takeda Pharmaceutical Co., Ltd. as Leukerin (tradename); 5-fluorouracil from Kyowa Hakko Kogyo Co., Ltd. as 5-FU (tradename); tegafur from Taiho Pharmaceutical Co., Ltd. as Futraful (tradename); doxyfluridine from Nippon Roche Co., Ltd. as Furutulon (tradename); carmofur from Yamanouchi Pharmaceutical Co., Ltd. as Yamafur (tradename); cytarabine from Nippon Shinyaku Co., Ltd. as Cylocide (tradename); cytarabine ocfosfate from Nippon Kayaku Co., Ltd. as Strasid (tradename); enocitabine from Asahi Kasei Corp. as Sanrabin (tradename); S-1 from Taiho Pharmaceutical Co., Ltd. as TS-1 (tradename); gemcitabine from Eli Lilly & Co. as Gemzar (tradename); fludarabine from Nippon Schering Co., Ltd. as Fludara (tradename); and pemetrexed disodium from Eli Lilly & Co. as Alimta (tradename).

The above-mentioned anticancer antibiotics are commercially available, as exemplified by the following: actinomycin D from Banyu Pharmaceutical Co., Ltd. as Cosmegen (tradename); doxorubicin from Kyowa Hakko Kogyo Co., Ltd. as Adriacin (tradename); daunorubicin from Meiji Seika Kaisha Ltd. as Daunomycin; neocarzinostatin from Yamanouchi Pharmaceutical Co., Ltd. as Neocarzinostatin (tradename); bleomycin from Nippon Kayaku Co., Ltd. as Bleo (tradename); pepromycin from Nippon Kayaku Co, Ltd. as Pepro (tradename); mitomycin C from Kyowa Hakko Kogyo Co., Ltd. as Mitomycin (tradename); aclarubicin from Yamanouchi Pharmaceutical Co., Ltd. as Aclacinon (tradename); pirarubicin from Nippon Kayaku Co., Ltd. as Pinorabicin (tradename); epirubicin from Pharmacia Corp. as Pharmorubicin (tradename); zinostatin stimalamer from Yamanouchi Pharmaceutical Co., Ltd. as Smancs (tradename); idarubicin from Pharmacia Corp. as Idamycin (tradename); sirolimus from Wyeth Corp. as Rapamune (tradename); and valrubicin from Anthra Pharmaceuticals Inc. as Valstar (tradename).

The above-mentioned plant-derived anticancer agents are commercially available, as exemplified by the following: vincristine from Shionogi & Co., Ltd. as Oncovin (tradename); vinblastine from Kyorin Pharmaceutical Co., Ltd. as Vinblastine (tradename); vindesine from Shionogi & Co., Ltd. as Fildesin (tradename); etoposide from Nippon Kayaku Co., Ltd. as Lastet (tradename); sobuzoxane from Zenyaku Kogyo Co., Ltd. as Perazolin (tradename); docetaxel from Aventis Corp. as Taxotere (tradename); paclitaxel from Bristol-Myers Squibb Co. as Taxol (tradename); and vinorelbine from Kyowa Hakko Kogyo Co., Ltd. as Navelbine (tradename).

The above-mentioned anticancer platinum coordination compounds are commercially available, as exemplified by the following: cisplatin from Nippon Kayaku Co., Ltd. as Randa (tradename); carboplatin from Bristol-Myers Squibb Co. as Paraplatin (tradename); nedaplatin from Shionogi & Co., Ltd. as Aqupla (tradename); and oxaliplatin from Sanofi-Synthelabo Co. as Eloxatin (tradename).

The above-mentioned anticancer camptothecin derivatives are commercially available, as exemplified by the following: irinotecan from Yakult Honsha Co., Ltd. as Campto (tradename); topotecan from GlaxoSmithKline Corp. as Hycamtin (tradename); and camptothecin from Aldrich Chemical Co., Inc., U.S.A.

The above-mentioned anticancer tyrosine kinase inhibitors are commercially available, as exemplified by the following: gefitinib from AstraZeneca Corp. as Iressa (tradename); imatinib from Novartis AG as Gleevec (tradename); and erlotinib from OSI Pharmaceuticals Inc. as Tarceva (tradename).

The above-mentioned monoclonal antibodies are commercially available, as exemplified by the following: cetuximab from Bristol-Myers Squibb Co. as Erbitux (tradename); bevacizumab from Genentech, Inc. as Avastin (tradename); rituximab from Biogen Idee Inc. as Rituxan (tradename); alemtuzumab from Berlex Inc. as Campath (tradename); and trastuzumab from Chugai Pharmaceutical Co., Ltd. as Herceptin (tradename).

The above-mentioned interferons are commercially available, as exemplified by the following: interferon α from Sumitomo Pharmaceutical Co., Ltd. as Sumiferon (tradename); interferon α-2a from Takeda Pharmaceutical Co., Ltd. as Canferon-A (tradename); interferon α-2b from Schering-Plough Corp. as Intron A (tradename); interferon β from Mochida Pharmaceutical Co., Ltd. as IFNβ (tradename);

interferon γ-1a from Shionogi & Co., Ltd. as Imunomax-γ (tradename); and interferon γ-n1 from Otsuka Pharmaceutical Co., Ltd. as Ogamma (tradename).

The above-mentioned biological response modifiers are commercially available, as exemplified by the following: krestin from Sankyo Co., Ltd. as Krestin (tradename); lentinan from Aventis Corp. as Lentinan (tradename); sizofiran from Kaken Seiyaku Co., Ltd. as Sonifiran (tradename); picibanil from Chugai Pharmaceutical Co., Ltd. as Picibanil (tradename); and ubenimex from Nippon Kayaku Co., Ltd. as Bestatin (tradename).

The above-mentioned other anticancer agents are commercially available, as exemplified by the following: mitoxantrone from Wyeth Lederle Japan, Ltd. as Novantrone (tradename); L-asparaginase from Kyowa Hakko Kogyo Co., Ltd. as Leunase (tradename); procarbazine from Nippon Roche Co., Ltd. as Natulan (tradename); dacarbazine from Kyowa Hakko Kogyo Co., Ltd. as Dacarbazine (tradename); hydroxycarbamide from Bristol-Myers Squibb Co. as Hydrea (tradename); pentostatin from Kagaku Oyobi Kessei Ryoho Kenkyusho as Coforin (tradename); tretinoin from Nippon Roche Co., Ltd. As Vesanoid (tradename); alefacept from Biogen Idee Inc. as Amevive (tradename); darbepoetin alfa from Amgen Inc. as Aranesp (tradename); anastrozole from AstraZeneca Corp. as Arimidex (tradename); exemestane from Pfizer Inc. as Aromasin (tradename); bicalutamide from AstraZeneca Corp. as Casodex (tradename); leuprorelin from Takeda Pharmaceutical Co., Ltd. as Leuplin (tradename); flutamide from Schering-Plough Corp. as Eulexin (tradename); fulvestrant from AstraZeneca Corp. as Faslodex (tradename); pegaptanib octasodium from Gilead Sciences, Inc. as Macugen (tradename); denileukin diftitox from Ligand Pharmaceuticals Inc. as Ontak (tradename); aldesleukin from Chiron Corp. as Proleukin (tradename); thyrotropin alfa from Genzyme Corp. as Thyrogen (tradename); arsenic trioxide from Cell Therapeutics, Inc. as Trisenox (tradename); bortezomib from Millennium Pharmaceuticals, Inc. as Velcade (tradename); capecitabine from Hoffmann-La Roche, Ltd. as Xeloda (tradename); and goserelin from AstraZeneca Corp. as Zoladex (tradename).

The invention also relates to a method for the treatment of cancer, which comprises administering to a subject in need thereof a therapeutically-effective amount of the compound of the invention or a pharmaceutically acceptable salt or ester thereof.

In the process according to the invention, preferred therapeutic unit may vary in accordance with, for example, the administration route of the compound of the invention, the type of the compound of the invention used, and the dosage form of the compound of the invention used; the type, administration route and dosage form of the other anticancer agent used in combination; and the type of cells to be treated, the condition of patient, and the like. The optimal treatment under the given conditions can be determined by a person skilled in the art, based on the set conventional therapeutic unit and/or based on the content of the present specification.

In the process according to the invention, the therapeutic unit for the compound of the invention may vary in accordance with, specifically, the type of compound used, the type of compounded composition, application frequency and the specific site to be treated, seriousness of the disease, age of the patient, doctor's diagnosis, the type of cancer, or the like. However, as an exemplary reference, the daily dose for an adult may be within a range of, for example, 1 to 1,000 mg in the case of oral administration. In the case of parenteral administration, preferably intravenous administration, and more preferably intravenous drip infusion, the daily dose may be within a range of, for example, 1 to 100 mg/m$^2$ (body surface area). Here, in the case of intravenous drip infusion, administration may be continuously carried out for, for example, 1 to 48 hours. Moreover, the administration frequency may vary depending on the administering method and symptoms, but it is, for example, once to five times a day. Alternatively, periodically intermittent administration such as administration every other day, administration every two days or the like may be employed as well in the administering method. The period of withdraw from medication in the case of parenteral administration is, for example, 1 to 6 weeks.

Although the therapeutic unit for the other anticancer agent used in combination with the compound of the invention is not particularly limited, it can be determined, if needed, by those skilled in the art according to known literatures. Examples may be as follows.

The therapeutic unit of 5-fluorouracil (5-FU) is such that, in the case of oral administration, for example, 200 to 300 mg per day is administered in once to three times consecutively, and in the case of injection, for example, 5 to 15 mg/kg per day is administered once a day for the first 5 consecutive days by intravenous injection or intravenous drip infusion, and then 5 to 7.5 mg/kg is administered once a day every other day by intravenous injection or intravenous drip infusion (the dose may be appropriately increased or decreased).

The therapeutic unit of S-1 (Tegafur, Gimestat and Ostat potassium) is such that, for example, the initial dose (singe dose) is set to the following standard amount in accordance with the body surface area, and it is orally administered twice a day, after breakfast and after dinner, for 28 consecutive days, followed by withdrawal from medication for 14 days. This is set as one course of administration, which is repeated. The initial standard amount per unit body surface area (Tegafur equivalent) is 40 mg in one administration for an area less than 1.25 m$^2$; 50 mg in one administration for an area of 1.25 m$^2$ to less than 1.5 m$^2$; 60 mg in one administration for an area of 1.5 m$^2$ or more. This dose is appropriately increased or decreased depending on the condition of the patient.

The therapeutic unit for gemcitabine is, for example, 1 g as gemcitabine/m$^2$ in one administration, which is administered by intravenous drip infusion over a period of 30 minutes, and one administration per week is continued for 3 weeks, followed by withdrawal from medication on the fourth week. This is set as one course of administration, which is repeated. The dose is appropriately decreased in accordance with age, symptom or development of side-effects.

The therapeutic unit for doxorubicin (e.g., doxorubicin hydrochloride) is such that, for example, in the case of intravenous injection, 10 mg (0.2 mg/kg) (titer) is administered once a day by intravenous one-shot administration for 4 to 6 consecutive days, followed by withdrawal from medication for 7 to 10 days. This is set as one course of administration, which is repeated two or three times. Here, the total dose is preferably 500 mg (titer)/m$^2$ (body surface area) or less, and it may be appropriately increased or decreased within the range.

The therapeutic unit for etoposide is such that, for example, in the case of intravenous injection, 60 to 100 mg/m$^2$ (body surface area) per day is administered for 5 consecutive days, followed by withdrawal from medication for three weeks (the dose may be appropriately increased or decreased). This is set as one course of administration, which is repeated. Meanwhile, in the case of oral administration, for example, 175 to 200 mg per day is administered for 5 consecutive days, followed by withdrawal from medication for three weeks (the dose may be appropriately increased or decreased). This is set as one course of administration, which is repeated.

The therapeutic unit for docetaxel (docetaxel hydrate) is such that, for example, 60 mg as docetaxel/m² (body surface area) is administered once a day by intravenous drip infusion over a period of 1 hour or longer at an interval of 3 to 4 weeks (the dose may be appropriately increased or decreased).

The therapeutic unit of paclitaxel is such that, for example, 210 mg/m² (body surface area) is administered once a day by intravenous drip infusion over a period of 3 hours, followed by withdrawal from medication for at least 3 weeks. This is set as one course of administration, which is repeated. The dose may be appropriately increased or decreased.

The therapeutic unit for cisplatin is such that, for example, in the case of intravenous injection, 50 to 70 mg/m² (body surface area) is administered once a day, followed by withdrawal from medication for 3 weeks or longer (the dose may be appropriately increased or decreased). This is set as one course of administration, which is repeated.

The therapeutic unit for carboplatin is such that, for example, 300 to 400 mg/m² is administered once a day by intravenous drip infusion over a period of 30 minutes or longer, followed by withdrawal from medication for at least 4 weeks (the dose may be appropriately increased or decreased). This is set as one course of administration, which is repeated.

The therapeutic unit for oxaliplatin is such that 85 mg/m² is administered once a day by intravenous injection, followed by withdrawal from medication for two weeks. This is set as one course of administration, which is repeated.

The therapeutic unit for irinotecan (e.g., irinotecan hydrochloride) is such that, for example, 100 mg/m² is administered once a day by intravenous drip infusion for 3 or 4 times at an interval of one week, followed by withdrawal from medication for at least two weeks.

The therapeutic unit for topotecan is such that, for example, 1.5 mg/m² is administered once a day by intravenous drip infusion for 5 days, followed by withdrawal from medication for at least 3 weeks.

The therapeutic unit for cyclophosphamide is such that, for example, in the case of intravenous injection, 100 mg is administered once a day by intravenous injection for consecutive days. If the patient can tolerate, the daily dose may be increased to 200 mg. The total dose is 3,000 to 8,000 mg, which may be appropriately increased or decreased. If necessary, it may be injected or infused intramuscularly, intrathoracically or intratumorally. On the other hand, in the case of oral administration, for example, 100 to 200 mg is administered a day.

The therapeutic unit for gefitinib is such that 250 mg is orally administered once a day.

The therapeutic unit for cetuximab is such that, for example, 400 mg/m² is administered on the first day by intravenous drip infusion, and then 250 mg/m² is administered every week by intravenous drip infusion.

The therapeutic unit for bevacizumab is such that, for example, 3 mg/kg is administered every week by intravenous drip infusion.

The therapeutic unit for trastuzumab is such that, for example, typically for an adult, once a day, 4 mg as trastuzumab/kg (body weight) is administered initially, followed by intravenous drip infusion of 2 mg/kg over a period of 90 minutes or longer every week from the second administration.

The therapeutic unit for exemestane is such that, for example, typically for an adult, 25 mg is orally administered once a day after meal.

The therapeutic unit for leuprorelin (e.g., leuprorelin acetate) is such that, for example, typically for an adult, 11.25 mg is subcutaneously administered once in 12 weeks.

The therapeutic unit for imatinib is such that, for example, typically for an adult in the chronic phase of chronic myelogenous leukemia, 400 mg is orally administered once a day after meal.

The therapeutic unit for a combination of 5-FU and leucovorin is such that, for example, 425 mg/m² of 5-FU and 200 mg/m² of leucovorin are administered from the first day to the fifth day by intravenous drip infusion, and this course is repeated at an interval of 4 weeks.

Effect of the Invention

The compounds of the invention have an excellent Wee1 kinase-inhibitory effect, and are useful in the field of medicine, especially in the field of various cancer treatments.

BEST MODE FOR CARRYING OUT THE INVENTION

The invention is described more concretely with reference to the following Examples and Production Examples, which, however, are not intended to restrict the scope of the invention.

Examples

In thin-layer chromatography in Examples and Production Examples, Silica Gel$_{60}$F$_{254}$ (Merck) was used for the plate, and a UV detector was used for detection. Wakogel™ C-300 or C-200 (Wako Pure Chemical Industries) or NH (Fuji Silysia Chemical) was used for column silica gel. In MS spectrometry, used was JMS-SX102A (JEOL) or QUATTROII (Micromass). In NMR spectrometry, dimethyl sulfoxide was used as the internal standard in a heavy dimethyl sulfoxide solution; a spectrometer of JNM-AL 400 (400 MHz; JEOL), Mercury 400 (400 MHz; Varian) or Inova 400 (400 MHz; Varian) was used; and all δ values are by ppm.

The meanings of the abbreviations in Production Examples and Examples are mentioned below.
s: singlet
d: doublet
dd: double doublet
ddd: double double doublet
t: triplet
dt: double triplet
ddt: double double triplet
q: quartet
m: multiplet
br: broad
J: coupling constant
Hz: hertz
DMSO-d$_6$: heavy dimethyl sulfoxide
CDCl$_3$: heavy chloroform
CD$_3$OD: heavy methanol Production Example 1

Production of 2-allyl-6-(methylthio)-1,2-dihydro-3H-pyrazolo[3,4-d]pyrimidin-3-one 1) Tert-butyl 1-allylhydrazinecarboxylate Tert-butyl hydrazinecarboxylate (250 g) was added to a toluene (3 L) solution of phthalic anhydride (280 g). In a Dean Stark water separator, the reaction mixture was heated under reflux for 3 hours. After cooled to room temperature, the formed solid was collected through filtration to give crude tert-butyl (1,3-dioxo-1,3-dihydro-2H-isoindol-2-yl)carbamate (516 g).

Potassium carbonate (520 g), benzyltriethylammonium chloride (43.3 g) and allyl bromide (250 mL) were added in order to an acetonitrile (3.5 L) solution of the above compound, and stirred at room temperature for 18 hours. Water (1.5 L) was added to the reaction solution, and the acetonitrile layer was separated and concentrated. Water (1 L) was added to the residue and to the aqueous layer, extracted with ethyl acetate, the ethyl acetate layer was washed with saturated saline water, and dried with anhydrous sodium sulfate. The solvent was evaporated away under reduced pressure, and the precipitated colorless solid was washed with hexane and dried to give crude tert-butyl (1,3-dioxo-1,3-dihydro-2H-isoindol-2-yl)carbamate (460 g).

In an ice bath, methylhydrazine (100 mL) was added to a tetrahydrofuran (3.0 L) solution of the above compound, then restored to room temperature, and stirred for 18 hours. The precipitated insoluble matter was removed through filtration, and the filtrate was concentrated. A mixed solvent of hexane/ethyl acetate (3/1) was added to the residue, and the precipitated insoluble matter was removed through filtration. This operation was repeated five times, and the filtrate was evaporated under reduced pressure. The resulting residue was evaporated under reduced pressure to give the entitled compound as a pale yellow oil (211 g).

ESI-MS Found: m/z[M+H]+ 173.

2) Production of 2-allyl-6-(methylthio)-1,2-dihydro-3H-pyrazolo[3,4-d]pyrimidin-3-one N,N-diisopropylethylamine (260 mL) and the hydrazine (106 g) obtained in the above 1 were added to a tetrahydrofuran (1.5 L) solution of ethyl 4-chloro-2-(methylthio)pyrimidine-5-carboxylate (142 g), and stirred with heating under reflux for 18 hours. After cooled to room temperature, the reaction solution was evaporated under reduced pressure, then diethyl ether (500 mL) was added to the residue, and the precipitated solid was separated through filtration. The filtrate was evaporated under reduced pressure, the residue was cooled in an ice bath, then trifluoroacetic acid (400 mL) was gradually added thereto, stirred at room temperature for 1 hour, and further stirred at 70° C. for 1 hour. The reaction solution was evaporated under reduced pressure, then ethanol (500 mL) was added thereto, and cooled in an ice bath, and then 6 N potassium hydroxide solution (1.0 L) was added thereto and stirred at room temperature for 15 minutes. Cooled in an ice bath, the reaction solution was acidified with concentrated hydrochloric acid (400 mL), and then evaporated under reduced pressure. The residue was partitioned between chloroform and water, then the chloroform layer was extracted, washed with saturated saline water, and dried with anhydrous sodium sulfate. The solvent was evaporated away under reduced pressure, then the formed yellow solid was collected through filtration, washed with ethanol and diethyl ether, and dried to give the entitled compound as a yellow solid (99.1 g).

$^1$H-NMR (400 MHz, DMSO-$d_6$) δ: 8.66 (1H, brs), 5.83 (1H, ddt, J=17.1, 9.8, 5.4 Hz), 5.13 (1H, d, J=9.8 Hz), 5.06 (1H, d, J=17.1 Hz), 4.34 (2H, d, J=5.4 Hz), 2.51 (3H, s).

ESI-MS Found: m/z[M+H]+ 223.

Production Example 2

Production of 2-isopropyl-6-(methylthio)-1,2-dihydro-3H-pyrazolo[3,4-d]pyrimidin-3-one

1) Production of ethyl 4-hydrazino-2-(methylthio)pyrimidine-5-carboxylate

To a solution of hydrazine monohydrate (9.71 g) dissolved in ethanol (200 mL) and cooled at 0° C., added was a solution of ethyl 4-chloro-2-(methylthio)pyrimidine-5-carboxylate (15.0 g) dissolved in ethanol (200 mL), and stirred for 1 hour. The precipitated solid was collected through filtration, washed with distilled water and dried to give the entitled compound as a white solid (9.66 g).

$^1$H-NMR (400 MHz, CD$_3$OD) δ: 8.56 (1H, s), 4.36 (2H, q, J=7.2 Hz), 2.62 (3H, s), 1.39 (3H, t, J=7.2 Hz).

ESI-MS Found: m/z[M+H]+ 229.

2) Production of ethyl 4-[2-(1-methylethylidene)hydrazino]-2-(methylthio)pyrimidine-5-carboxylate The above compound (9.66 g) was dissolved in acetone (300 mL), and stirred at 70° C. for 12 hours. The reaction solution was cooled to room temperature, then the solvent was evaporated away under reduced pressure to give the entitled compound as a white solid (9.66 g).

$^1$H-NMR (400 MHz, CDCl$_3$) δ: 8.75 (1H, s), 4.36 (2H, q, J=6.8 Hz), 2.60 (3H, s), 2.17 (3H, s), 2.04 (3H, s), 1.40 (3H, t, J=6.8 Hz).

ESI-MS Found: m/z[M+H]+ 269.

3) Production of ethyl 4-(2-isopropylhydrazino)-2-(methylthio)pyrimidine-5-carboxylate The above-compound (9.66 g) was dissolved in methanol (180 mL), and cooled to 0° C. A methanol (36 mL) solution of sodium cyanoborohydride (2.26 g) and concentrated hydrochloric acid (0.15 mL) were added to the reaction solution, and stirred for 30 minutes. Aqueous saturated sodium hydrogencarbonate solution was added to the reaction solution, and extracted with ethyl acetate. This was dried with anhydrous sodium sulfate, then the solvent was evaporated away under reduced pressure to give the entitled compound as a yellow amorphous substance (10.2 g).

$^1$H-NMR (400 MHz, CDCl$_3$) δ: 9.39 (1H, s), 8.62 (1H, s), 4.34 (2H, q, J=7.2 Hz), 3.24 (1H, septet, J=6.3 Hz), 2.54 (3H, s), 1.37 (3H, t, J=7.1 Hz), 1.14 (6H, d, J=6.3 Hz).

ESI-MS Found: m/z[M+H]+ 271.

4) Production of 2-isopropyl-6-(methylthio)-1,2-dihydro-3H-pyrazolo[3,4-d]pyrimidin-3-one Aqueous 5 N sodium hydroxide solution (300 mL) was added to a methanol (100 mL) solution of the above compound (10.2 g), and stirred for 3 hours. Methanol was evaporated away under reduced pressure, then aqueous 5 N hydrochloric acid solution was added to the residue to make it have pH of about 2, and then stirred for 3 hours. The reaction solution was extracted with chloroform, washed with saturated saline water, and dried with anhydrous sodium sulfate. The solvent was evaporated away under reduced pressure to give the entitled compound as an orange amorphous substance (7.52 g).

$^1$H-NMR (400 MHz, CDCl$_3$) δ: 8.71 (1H, s), 4.85 (1H, septet, J=6.8 Hz), 2.60 (3H, s), 1.44 (6H, d, J=6.8 Hz).

ESI-MS Found: m/z[M+H]+ 225.

Production Example 3

Production of 2-methyl-6-(methylthio)-1,2-dihydro-3H-pyrazolo[3,4-d]pyrimidin-3-one

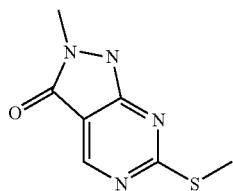

The entitled compound was obtained as a pale yellow solid according to the same method as in Production Example 1, for which, however, tert-butyl 1-methylhydrazinecarboxylate was used in place of tert-butyl 1-allylhydrazinecarboxylate used in Production Example 1-1.

ESI-MS Found: m/z[M+H]+ 197.

Production Example 4

Production of [5-amino-2-(4-ethylpiperazin-1-yl)phenyl]methanol

1) Production of [5-nitro-2-(4-ethylpiperazin-1-yl)phenyl]methanol

Potassium carbonate (4.24 g) was added to an N-methylpyrrolidone (4.24 mL) solution of 2-fluoro-5-nitrobenzyl alcohol (4.24 g) and N-ethylpiperazine (4.24 g), and stirred at 140° C. for 14 hours. Water was added to the reaction liquid, and extracted with ethyl acetate. The organic layer was washed with water and saturated saline water in order, dried with anhydrous magnesium sulfate, and the solvent was evaporated away under reduced pressure. The crude product was purified through silica gel column chromatography (hexane/ethyl acetate) to give the entitled compound as a yellow solid.

2) Production of [5-amino-2-(4-ethylpiperazin-1-yl)phenyl]methanol

Iron (7.0 g) and ammonium chloride (15 g) were added to an ethanol/water (1/1) (80 mL) solution of the compound obtained in the above reaction, and heated under reflux for 1 hour. The reaction liquid was concentrated under reduced pressure, and made basic with aqueous 5 N sodium hydroxide solution added thereto. This was extracted with chloroform/isopropanol (80/20), the organic layer was dried with anhydrous magnesium sulfate, and the solvent was evaporated away to give the entitled compound (2.49 g).

$^1$H-NMR (400 MHz, CDCl$_3$) δ: 8.27 (1H, d, J=2.4 Hz), 8.14 (1H, dd, J=8.8, 2.9 Hz), 7.16 (1H, d, J=9.3 Hz), 4.80 (2H, s), 3.10 (4H, t, J=4.9 Hz), 2.66 (4H, brs), 2.51 (2H, q, J=7.3 Hz), 1.14 (3H, t, J=7.1 Hz).

ESI-MS Found: m/z[M+H]+ 236.

Production Example 5

Production of 4-[4-(2-hydroxyethyl)piperazin-1-yl]-3-methylaniline

1) Production of 1-(2-hydroxyethyl)-4-(2-methyl-4-nitrophenyl)piperazine

The entitled compound was obtained as a yellow solid according to the same method as in Production Example 4-1, for which, however, 4-(2-hydroxyethyl)piperazine was used in place of N-ethylpiperazine used in Production Example 4-1, 5-nitro-2-fluoro toluene was used in place of 2-fluoro-5-nitrobenzyl alcohol, N,N-diisopropylethylamine was used in place of potassium carbonate, and dimethyl sulfoxide was used in place of N-methylpyrrolidone.

2) Production of 4-[4-(2-hydroxyethyl)piperazin-1-yl]-3-methylaniline

The entitled compound was obtained as a white solid according to the same method as in Production Example 4-2, for which, however, 1-(2-hydroxyethyl)-4-(2-methyl-4-nitrophenyl)piperazine was used in place of [5-nitro-2-(4-ethylpiperazin-1-yl)phenyl]methanol used in Production Example 4-2.

$^1$H-NMR (400 MHz, DMSO-d$_6$) δ: 6.73 (1H, d, J=8.3 Hz), 6.37 (1H, d, J=2.4 Hz), 6.3 (1H, dd, J=8.3, 2.4 Hz), 4.63 (2H, s), 4.38 (1H, t, J=5.4 Hz), 3.50 (2H, t, J=6.3 Hz), 2.67 (4H, t, J=4.6 Hz), 2.53-2.48 (4H, m), 2.41 (2H, t, J=6.3 Hz), 2.09 (3H, s).

ESI-MS Found: m/z[M+H]+ 236.

Production Example 6

Production of 1-(2-methyl-4-nitrophenyl)piperazine hydrochloride

Crude tert-butyl 4-[2-methyl-4-nitrophenyl]piperazine-1-carboxylate (4.91 g) was obtained according to the same method as in Production Example 4-1, for which, however, tert-butyl piperazine-1-carboxylate was used in place of N-ethylpiperazine used in Production Example 4-1, 2-fluoro-5-nitrotoluene was used in place of 2-fluoro-5-nitrobenzyl alcohol, N,N-diisopropylethylamine was used in place of potassium carbonate, and dimethyl sulfoxide was used in place of N-methylpyrrolidone.

4N hydrochloric acid/ethyl acetate solution was added to a methanol (50 mL) solution of the compound obtained in the above reaction, and stirred at room temperature for 30 minutes. The reaction liquid was concentrated under reduced pressure to give crude 4-(2-methyl-4-nitrophenyl)piperazine hydrochloride (3.86 g).

Production Example 7

Production of 4-(4-isopropylpiperazin-1-yl)-3-methylaniline

1) Production of 1-isopropyl-4-(2-methyl-4-nitrophenyl)piperazine

Acetone (1.13 g) and sodium cyanoborohydride (183 mg) were added to an ethanol (20 mL) solution of the compound (500 mg) obtained in Production Example 6, and stirred at room temperature for 15 hours. The reaction liquid was concentrated under reduced pressure, and the residue was made basic with aqueous 2 N sodium hydroxide solution added thereto. This was extracted with chloroform, the organic layer was dried with anhydrous magnesium sulfate, and the solvent was evaporated away. The crude product was purified through silica gel column chromatography (hexane/ethyl acetate) to give the entitled compound as a yellow solid (120 mg).

2) Production of 4-(4-isopropylpiperazin-1-yl)-3-methylaniline

The entitled compound was obtained as a white solid (91 mg) according to the same method as in Production 4-2, for which, however, 1-isopropyl-4-(2-methyl-4-nitrophenyl)piperazine was used in place of [5-nitro-2-(4-ethylpiperazin-1-yl)phenyl]methanol used in Production Example 4-2.

$^1$H-NMR (400 MHz, DMSO-$d_6$) δ: 6.73 (1H, d, J=8.3 Hz), 6.37 (1H, d, J=2.4 Hz), 6.32 (1H, dd, J=8.3, 2.4 Hz), 4.62 (2H, s), 2.66 (4H, t, J=4.9 Hz), 2.66-2.60 (1H, m), 2.54-2.47 (4H, m), 2.09 (3H, s), 0.98 (6H, d, J=6.3 Hz).

ESI-MS Found: m/z[M+H]+ 234.

Production Example 8

Production of 4-{4-[2-(methylsulfonyl)ethyl]piperazin-1-yl}aniline

1) Production of 1-(4-nitrophenyl)piperazine hydrochloride

Crude 4-(4-nitrophenyl)piperazine hydrochloride (4.33 g) was obtained according to the same method as in Production Example 6, for which, however, 4-fluoronitrobenzene was used in place of 2-fluoro-5-nitrotoluene used in Production Example 6.

2) Production of 1-[2-(methylsulfonyl)ethyl]-4-(4-nitrophenyl)piperazine

Methylvinyl sulfone (0.49 mL) and N,N-diisopropylethylamine (0.5 mL) were added to an ethanol (10 mL) solution of the compound (458 mg) obtained in Production Example 8-1, and stirred at room temperature for 15 hours. Aqueous saturated sodium hydrogencarbonate solution was added to the reaction liquid, and extracted three times with ethyl acetate. The organic layer was washed with saturated saline water, and dried with anhydrous sodium sulfate. The solvent was evaporated away to give crude 1-[2-(methylsulfonyl)ethyl]-4-(4-nitrophenyl)piperazine.

3) Production of 4-{4-[2-(methylsulfonyl)ethyl]piperazin-1-yl}aniline

10% palladium-carbon (200 mg) was added to a methanol (20 mL) solution of the compound obtained in Production Example 8-2, and stirred in 1-atmospheric hydrogen at room temperature for 4 hours. The palladium-carbon was removed through filtration, and the filtrate was concentrated under reduced pressure to give the entitled compound (611 mg).

$^1$H-NMR (400 MHz, DMSO-$d_6$) δ: 6.85 (2H, d, J=8.3 Hz), 6.47 (2H, d, J=8.8 Hz), 4.82 (2H, s), 3.28 (2H, t, J=6.6 Hz), 3.03 (3H, s), 2.96 (2H, d, J=10.7 Hz), 2.70 (2H, t, J=6.0 Hz), 2.01 (2H, t, J=11.2 Hz), 1.66 (2H, d, J=11.2 Hz), 1.51 (2H, ddd, J=24.5, 12.1, 3.3 Hz).

ESI-MS Found: m/z[M+H]+ 284.

Production Example 9

Production of 4-(1,1-dioxidothiomorpholin-4-yl)-3-methylaniline

1) Production of 4-(2-methyl-4-nitrophenyl)thiomorpholine-1,1-dioxide

Crude 4-(2-methyl-4-nitrophenyl)thiomorpholine was obtained according to the same method as in Production Example 4-1, for which, however, thiomorpholine was used in place of N-ethylpiperazine used in Production Example 4-1, 5-nitro-2-fluorotoluene was used in place of 2-fluoro-5-nitrobenzyl alcohol, N,N-diisopropylethylamine was used in place of potassium carbonate, and dimethyl sulfoxide was used in place of N-methylpyrrolidone.

M-chloroperbenzoic acid (19 g) was added to a chloroform (100 mL) solution of the compound obtained in the above reaction, and stirred with cooling with ice for 24 hours. The reaction liquid was washed with aqueous sodium sulfite solution and aqueous saturated sodium hydrogencarbonate solution in order, and dried with anhydrous sodium sulfate. The solvent was evaporated away under reduced pressure to give the entitled compound (4.85 g).

2) Production of 4-(1,1-dioxidothiomorpholin-4-yl)-3-methylaniline

The entitled compound was obtained as a white solid according to the same method as in Production Example 8-3, for which, however, 4-(2-methyl-4-nitrophenyl)thiomorpholine 1,1-dioxide was used in place of 1-[2-(methylsulfonyl)ethyl]-4-(4-nitrophenyl)piperazine used in Production Example 8-3.

$^1$H-NMR (400 MHz, DMSO-$d_6$) δ: 10.08-9.87 (2H, m), 7.19 (1H, d, J=8.3 Hz), 7.14-7.10 (1H, m), 7.13 (1H, s), 3.26 (8H, s), 2.28 (3H, s).

ESI-MS Found: m/z[M+H]+ 241.

Production Example 10

Production of 3-methyl-4-(1-methyl-1H-pyrazol-4-yl)aniline

1) Production of 1-methyl-4-(2-methyl-4-nitrophenyl)-1H-pyrazole

Aqueous 2 M sodium carbonate solution (5 mL) was added to a 1,2-dimethoxyethane (10 mL) solution of 2-bromo-5-nitrotoluene (216 mg), 1-methyl-4-(4,4,5,5-tetramethyl-1,3,2-dioxaboroaran-1-yl)-1H-pyrazole (208 mg) and tetrakis(triphenylphosphine)palladium(0) (10 mg), and heated under reflux for 16 hours. The reaction liquid was washed with water, and the organic layer was dried with anhydrous sodium sulfate. The solvent was evaporated away under reduced pressure, and the crude product was purified through silica gel column chromatography (hexane/ethyl acetate) to give the entitled compound as a white solid (357 mg).

$^1$H-NMR (400 MHz, CDCl$_3$) δ: 8.12 (1H, d, J=2.3 Hz), 8.04 (1H, dd, J=7.3, 2.3 Hz), 7.70 (1H, s), 7.58 (1H, s), 8.12 (1H, d, J=7.3 Hz), 4.00 (3H, s), 2.51 (3H, s).

ESI-MS Found: m/z[M+H]+ 218.

2) Production of 3-methyl-4-(1-methyl-1H-pyrazol-4-yl)aniline

The entitled compound was obtained as a white solid (311 mg) according to the same method as in Production Example 4-2, for which, however, 1-methyl-4-(2-methyl-4-nitrophenyl)-1H-pyrazole was used in place of [5-nitro-2-(4-ethylpiperazin-1-yl)phenyl]methanol used in Production Example 4-2.

ESI-MS Found: m/z[M+H]+ 188.

Production Example 11

Production of methyl 3-[2-allyl-6-(methylthio)-3-oxo-1,2-dihydro-3H-pyrazolo[3,4-d]pyrimidin-1-yl]benzoate Pyridine (20 mL) was added to a chloroform solution of 2-allyl-6-(methylthio)-1,2-dihydro-3H-pyrazolo[3,4-d]pyrimidin-3-one (7.5 g), copper(II)acetate (6.1 g) and [3-(methoxycarbonyl)]phenylboronic acid (10 g), and stirred at room temperature for 3 days. Aqueous 30% ammonia solution and saturated saline water were added to the reaction liquid in order, and extracted with chloroform. The organic layer was washed with saturated saline water, dried with anhydrous magnesium sulfate, and the solvent was evaporated away. The crude product was purified through silica gel column chromatography (hexane/ethyl acetate) to give methyl 3-[2-allyl-6-(methylthio)-3-oxo-1,2-dihydro-3H-pyrazolo[3,4-d]pyrimidin-1-yl]benzoate as a yellow oil (6.7 g).

$^1$H-NMR (400 MHz, CDCl$_3$) δ: 8.92 (1H, s), 8.11-8.06 (2H, m), 7.65-7.59 (2H, m), 5.68 (1H, ddt, J=17.1, 10.2, 5.9 Hz), 5.13 (1H, dd, J=10.2, 1.0 Hz), 4.97 (1H, dd, J=17.1, 1.0 Hz), 4.45 (2H, d, J=5.9 Hz), 3.96 (3H, s), 2.51 (3H, s).

Production Example 12

Production of 2-allyl-6-{[3-hydroxymethyl-4-(4-methylpiperazin-1-yl)phenyl]amino}-1-pyridin-2-yl-1,2-dihydro-3H-pyrazolo[3,4-d]pyrimidin-3-one 1) Production of 2-allyl-6-(methylthio)-1-pyridin-2-yl-3H-pyrazolo[3,4-d]pyrimidin-3-one N,N'-dimethylethylenediamine (2.4 mL) was added to a 1,4-dioxane (50 mL) solution of 2-allyl-6-(methylthio)-1,2-dihydro-3H-pyrazolo[3,4-d]pyrimidin-3-one (4.44 g), copper(I) iodide (3.80 g), 2-iodopyridine (5.33 g) and potassium carbonate (3.80 g), and stirred overnight at 95° C. The reaction liquid was cooled, then aqueous ammonia was added thereto and extracted with ethyl acetate, washed with saturated saline water, and dried with anhydrous magnesium sulfate. The solvent was evaporated away under reduced pressure, and the residue was crystallized with ethyl acetate to give the entitled compound as a white solid (5.15 g).

$^1$H-NMR (400 MHz, CDCl$_3$) δ: 8.94 (1H, s), 8.52 (1H, d, J=5.1 Hz), 7.90 (2H, d, J=3.5 Hz), 7.29-7.25 (1H, m), 5.68 (1H, ddt, J=17.0, 10.2, 6.3 Hz), 5.05 (1H, d, J=10.2 Hz), 4.91 (1H, d, J=17.0 Hz), 4.85 (2H, d, J=6.3 Hz), 2.58 (3H, s).

ESI-MS Found: m/z[M+H]+ 300.

2) Production of 2-allyl-6-{[3-hydroxymethyl-4-(4-methylpiperazin-1-yl)phenyl]amino}-1-pyridin-2-yl-1,2-dihydro-3H-pyrazolo[3,4-d]pyrimidin-3-one M-chloroperbenzoic acid (>65%) (796 mg) was added to a toluene (20 mL) solution of 2-allyl-6-(methylthio)-1-pyridin-2-yl-3H-pyrazolo[3,4-d]pyrimidin-3-one (898 mg), and stirred for 30 minutes. N,N-diisopropylethylamine (1.60 mL), [5-amino-2-(4-methylpiperazin-1-yl)phenyl]methanol (800 mg) and tetrahydrofuran (10 mL) were added to the reaction liquid, and stirred overnight. Aqueous saturated sodium hydrogencarbonate solution was added to the reaction liquid, and extracted with a chloroform/isopropanol (80/20) mixed solution. This was dried with anhydrous magnesium sulfate, the solvent was evaporated away, and the residue was purified through basic silica gel chromatography (hexane/ethyl acetate=50/50 to 0/100). The resulting crystal was recrystallized with ethanol to give the entitled compound as a white crystal (941 mg).

$^1$H-NMR (400 MHz, CDCl$_3$) δ: 8.85 (1H, s), 8.54 (1H, ddd, J=4.9, 4.9, 1.0 Hz), 7.91 (1H, ddd, J=8.8, 6.8, 1.5 Hz), 7.85 (1H, d, J=7.8 Hz), 7.61 (1H, s), 7.50 (1H, s), 7.34 (1H, d, J=8.8 Hz), 7.29-7.25 (1H, m), 7.21 (1H, d, J=8.8 Hz), 5.73 (1H, ddt, J=17.1, 10.0, 6.3 Hz), 5.48 (1H, s), 5.02 (1H, dd, J=10.0, 1.2 Hz), 4.91 (1H, dd, J=17.1, 1.5 Hz), 4.79 (2H, s), 4.78 (2H, d, J=6.3 Hz), 3.02 (4H, t, J=4.6 Hz), 2.62 (4H, s), 2.38 (3H, s).

ESI-MS Found: m/z[M+H]+ 473.

Production Example 13

Production of 1-(4-aminophenyl)-N-(tert-butyl)pyrrolidin-3-amine

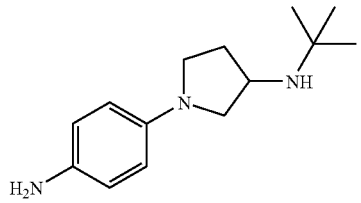

1) Production of 1-benzyl-N-(tert-butyl)pyrrolidin-3-amine

A methanol solution (38 mL) of 0.3 M sodium cyanoborohydride/0.15 M zinc chloride mixture was added to a tetrahydrofuran (10 mL) solution of 1-benzyl-3-pyrrolidone (1.83 mL). This was stirred at room temperature for 1 hour, then zinc chloride (1.56 g) was added thereto and stirred for 72 hours. Saturated sodium hydrogencarbonate was added to it, and extracted with ethyl acetate. This was washed with saturated saline water, then dried with anhydrous magnesium sulfate, the solvent was evaporated away, and the residue was purified through basic silica gel column chromatography (chloroform/methanol) to give the entitled compound as a colorless oily substance (739 mg).

$^1$H-NMR (400 MHz, CDCl$_3$) δ: 7.34-7.23 (5H, m), 3.58 (2H, dd, J=17.1, 12.7 Hz), 3.47-3.39 (1H, m), 2.95 (1H, t, J=7.8 Hz), 2.68 (1H, td, J=8.5, 4.9 Hz), 2.50-2.42 (1H, m), 2.25-2.15 (1H, m), 2.10 (1H, dd, J=9.3, 7.3 Hz), 2.05 (1H, s), 1.50-1.42 (1H, m), 1.29-1.22 (1H, m), 1.07 (9H, s).

2) Production of N-(tert-butyl)-1-(4-nitrophenyl)pyrrolidin-3-amine

4 N hydrochloric acid/dioxane solution (0.795 mL) and 20% palladium hydroxide/carbon (500 mg) were added to a tetrahydrofuran (10 mL)/methanol (10 mL) mixed solution of the compound (739 mg) obtained in the above reaction, and stirred overnight in a hydrogen atmosphere at room temperature. The reaction liquid was filtered, the solvent was evaporated away, and 4-fluoronitrobenzene (0.337 mL), sodium hydrogencarbonate (534 mg) and isopropanol (10 mL) were added to the resulting residue, and stirred overnight at 90° C.

Chloroform and water were added to the reaction liquid, the organic layer was separated, washed with saturated saline water, and dried with anhydrous magnesium sulfate. The solvent was evaporated away, the resulting crude product was purified through silica gel column chromatography (hexane/ethyl acetate) to give the entitled compound as a yellow solid substance (606 mg).

$^1$H-NMR (400 MHz, CDCl$_3$) δ: 8.12 (2H, d, J=9.3 Hz), 6.45 (2H, d, J=9.3 Hz), 3.68-3.50 (3H, m), 3.38 (1H, td, J=9.6, 7.0 Hz), 3.02 (1H, dd, J=9.3, 7.3 Hz), 2.35-2.28 (1H, m), 1.87-1.77 (1H, m), 1.16 (9H, s).

3) Production of 1-(4-aminophenyl)-N-(tert-butyl)pyrrolidin-3-amine

The compound obtained through the above reaction was reduced to give the entitled compound as a white solid (309 mg).

¹H-NMR (400 MHz, CDCl₃) δ: 6.67 (2H, d, J=8.8 Hz), 6.44 (2H, d, J=8.8 Hz), 3.57-3.47 (2H, m), 3.32-3.19 (2H, m), 2.90-2.84 (1H, m), 2.29-2.21 (1H, m), 1.79-1.69 (1H, m), 1.15 (9H, s).

Production Example 14

Production of 6'-[6-(methylthio)-3-oxo-(2-propynyl)-2,3-dihydro-1H-pyrazolo[3,4-d]pyrimidin-1-yl]-2H-1,2'-bipyridin-2-one

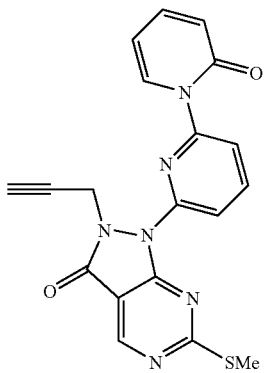

Ammonium formate (964 mg) and [1,1'-bis(diphenylphosphino)-ferrocene]dichloropalladium(II)/dichloromethane complex (208 mg) were added to a tetrahydrofuran (10 mL) solution of 6'-[2-allyl-6-(methylthio)-3-oxo-2,3-dihydro-1H-pyrazolo[3,4-d]pyrimidin-1-yl]-2H-1,2'-bipyridin-2-one (1 g), and heated overnight under reflux. The reaction liquid was cooled to room temperature, then diluted with chloroform, and washed with water and saturated saline water in order. The organic layer was dried with anhydrous magnesium sulfate. The insoluble matter was dissolved, and then the solvent was evaporated away to give crude 6'-[6-(methylthio)-3-oxo-2,3-dihydro-1H-pyrazolo[3,4-d]pyrimidin-1-yl]-2H-1,2'-bipyridin-2-one.

The above compound was dissolved in N,N'-dimethylformamide (10 mL), and sodium hydride (112 mg) was added thereto. This was stirred at room temperature for 1 hour, then propargyl bromide (909 mg) was added thereto, and stirred overnight at room temperature. Water was added to the reaction liquid, and extracted with chloroform. The resulting organic layer was washed with water and saturated saline water in order, then dried with anhydrous magnesium sulfate. The insoluble matter was removed through filtration, then the solvent was evaporated away, and the resulting residue was purified through silica gel column chromatography (n-hexane/ethyl acetate) to give the entitled compound as a pale brown solid (396 mg).

¹H-NMR (400 MHz, CDCl₃) δ: 8.95 (1H, s), 8.16-8.13 (1H, m), 8.07 (1H, t, J=8.0 Hz), 7.94 (1H, dd, J=7.8, 1.0 Hz), 7.81 (1H, dd, J=7.6, 1.7 Hz), 7.41 (1H, ddd, J=9.4, 6.5, 2.1 Hz), 6.67 (1H, d, J=9.3 Hz), 6.31 (1H, td, J=6.8, 1.0 Hz), 4.99 (2H, d, J=2.4 Hz), 2.64 (3H, s), 2.12 (1H, t, J=2.4 Hz).
ESI-MS Found: m/z[M+H]+ 391

Compounds of the following Production Examples were produced according to known methods, or according to the methods described in Examples, or according to methods similar thereto, optionally as combined.

Production Example 15

2-Allyl-1-(3-bromophenyl)-6-(methylthio)-1,2-dihydro-3H-pyrazolo[3,4-d]pyrimidin-3-one

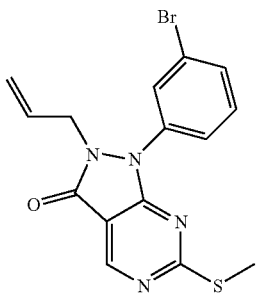

¹H-NMR (400 MHz, CDCl₃) δ: 8.91 (1H, s), 7.63-7.60 (1H, m), 7.55-7.52 (1H, m), 7.41-7.35 (2H, m), 5.73-5.63 (1H, m), 5.15 (1H, dd, J=10.2, 1.3 Hz), 5.01 (1H, dd, J=17.1, 1.3 Hz), 4.45-4.43 (2H, m), 2.53 (3H, s).

Production Example 16

4-(3,3-Difluoroazetidin-1-yl)aniline

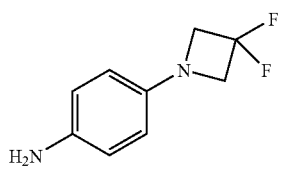

¹H-NMR (400 MHz, CDCl₃) δ: 6.66 (2H, d, J=8.8 Hz), 6.39 (2H, d, J=8.8 Hz), 4.12 (4H, t, J=11.7 Hz), 3.39 (2H, brs).

Production Example 17

1-(4-Aminophenyl)-N,N-dimethylazetidin-3-amine

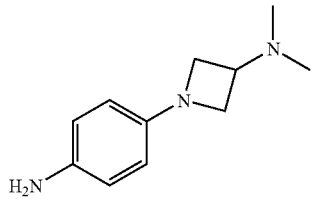

¹H-NMR (400 MHz, CDCl₃) δ: 6.62 (2H, d, J=8.3 Hz), 6.36 (2H, d, J=8.8 Hz), 3.89 (2H, t, J=6.8 Hz), 3.53 (2H, t, J=6.3 Hz), 3.23-3.17 (1H, m), 2.76 (2H, brs), 2.19 (6H, s).

Production Example 18

(2S)-1-(4-nitrophenyl)-2-(pyrrolidin-1-ylmethyl)pyrrolidine

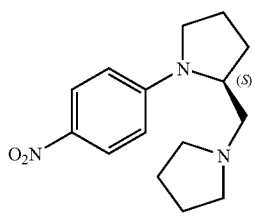

$^1$H-NMR (400 MHz, CDCl$_3$) δ: 8.11 (2H, d, J=9.3 Hz), 6.54 (2H, d, J=9.3 Hz), 4.02-3.97 (1H, m), 3.52-3.47 (1H, m), 3.27 (1H, dd, J=18.0, 8.8 Hz), 2.68-2.62 (2H, m), 2.57-2.49 (4H, m), 2.24-2.19 (1H, m), 2.14-1.98 (3H, m), 1.82-1.79 (4H, m).

Production Example 19

4-[(2S)-2-(pyrrolidin-1-ylmethyl)pyrrolidin-1-yl]aniline

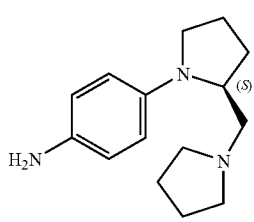

$^1$H-NMR (400 MHz, CDCl$_3$) δ: 6.67 (2H, d, J=8.8 Hz), 6.52 (2H, d, J=8.8 Hz), 3.76-3.70 (1H, m), 3.41-3.36 (1H, m), 3.02 (1H, ddd, J=16.1, 9.8, 3.4 Hz), 2.69-2.63 (2H, m), 2.57-2.53 (3H, m), 2.43 (1H, dd, J=12.2, 10.2 Hz), 2.08-1.93 (4H, m), 1.81-1.78 (4H, m).

Production Example 20

N-methyl-4-nitro-N-(pyridin-2-ylmethyl)aniline

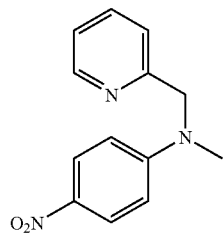

$^1$H-NMR (400 MHz, CDCl$_3$) δ: 8.61 (1H, d, J=4.9 Hz), 8.11 (2H, d, J=9.3 Hz), 7.64 (1H, td, J=7.7, 1.6 Hz), 7.21 (1H, dd, J=7.6, 5.1 Hz), 7.07 (1H, d, J=7.8 Hz), 6.67 (2H, d, J=9.3 Hz), 4.77 (2H, s), 3.28 (3H, s).

Production Example 21

N-methyl-N-(pyridin-2-ylmethyl)benzene-1,4-diamine

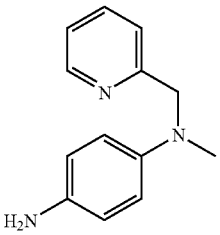

$^1$H-NMR (400 MHz, CDCl$_3$) δ: 8.57-8.56 (1H, m), 7.59 (1H, td, J=7.6, 1.8 Hz), 7.23 (1H, d, J=7.8 Hz), 7.14 (1H, dd, J=8.5, 4.6 Hz), 6.64 (4H, s), 4.52 (2H, s), 3.32 (2H, s), 2.99 (3H, s).

Production Example 22

4-(2-Methyl-2,7-diazaspiro[3.5]non-7-yl)aniline

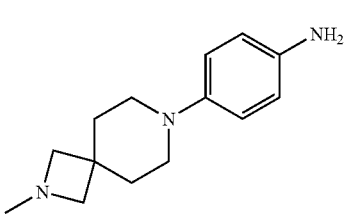

$^1$H-NMR (400 MHz, CDCl$_3$) δ: 6.81 (2H, d, J=8.8 Hz), 6.64 (2H, d, J=9.3 Hz), 3.42 (2H, s), 3.09 (4H, s), 2.93 (4H, t, J=5.6 Hz), 2.38 (3H, s), 1.89 (4H, t, J=5.6 Hz).

Production Example 23

Production of 2'-methyl-2',3'-dihydro-1'H-spiro[cyclopropane-1,4'-isoquinolin]-7'-amine 1) Production of methyl 1-(2-cyanophenyl)cyclopropanecarboxylate

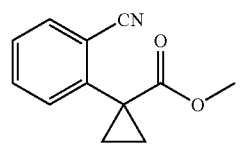

Tetra-n-butylammonium bromide (1.5 g), 1,2-dibromoethane (6.5 g) and aqueous 50% sodium hydroxide solution (20 mL) were added to a toluene (40 mL) solution of methyl 2-cyanophenylacetate (4.0 g), and stirred at room temperature for 1 hour. Water was added to the reaction liquid, and extracted with ethyl acetate. The organic layer was washed with saturated saline water, then dried with anhydrous magnesium sulfate, and the solvent was evaporated away under reduced pressure. The crude product was purified through silica gel column chromatography (hexane/ethyl acetate) to give the entitled compound as a colorless solid (3.0 g).

$^1$H-NMR (400 MHz, CDCl$_3$) δ: 7.66 (1H, dd, J=7.6, 1.2 Hz), 7.55 (1H, td, J=7.6, 1.2 Hz), 7.43-7.36 (2H, m), 3.66 (3H, s), 1.82 (2H, q, J=3.7 Hz), 1.30 (2H, q, J=3.7 Hz).

ESI-MS Found: m/z[M+H] 202.

2) Production of methyl 1-[2-(aminomethyl)phenyl]cyclopropanecarboxylate monohydrochloride

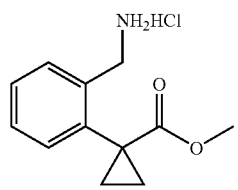

10% palladium/carbon (1.6 g) was added to an ethanol (50 mL) solution of the compound (2.95 g) obtained in the above reaction 1), and stirred in 2-atmospheric hydrogen at room temperature for 3 hours. The palladium/carbon was removed through filtration, the filtrate was concentrated under reduced pressure, and the crude product was washed with diethyl ether to give the entitled compound as a colorless solid (3.2 g).

$^1$H-NMR (DMSO-d$_6$) δ: 8.47 (2H, s), 7.55 (1H, d, J=6.8 Hz), 7.38 (3H, td, J=7.2, 2.1 Hz), 7.36-7.29 (2H, m), 4.04 (2H, d, J=4.9 Hz), 3.54 (3H, s), 1.61-1.56 (2H, m), 1.33-1.29 (2H, m).

ESI-MS Found: m/z[M+H] 206

3) Production of 1',2'-dihydro-3'H-spiro[cyclopropane-1,4'-isoquinolin]-3'-one

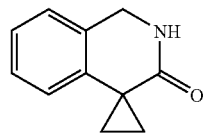

Aqueous 5 N sodium hydroxide solution (4 mL) was added to a methanol (50 mL) solution of the compound (3.2 g) obtained in the above reaction 2), and stirred at room temperature for 30 minutes. This was neutralized with aqueous 1 N hydrochloric acid solution added thereto, and methanol was evaporated away under reduced pressure. The residue was diluted with water, and extracted three times with ethyl acetate. The organic layer was washed with saturated saline water, dried with anhydrous magnesium sulfate, and the solvent was evaporated away under reduced pressure to give the entitled compound as a colorless solid (2.1 g).

$^1$H-NMR (CDCl$_3$) δ: 7.23 (1H, td, J=7.8, 1.1 Hz), 7.18 (1H, td, J=7.3, 1.1 Hz), 7.10 (1H, dd, J=7.3, 1.0 Hz), 6.73 (1H, dd, J=7.8, 1.0 Hz), 4.69 (2H, d, J=1.5 Hz), 1.85 (2H, q, J=3.7 Hz), 1.24 (2H, q, J=3.7 Hz).

ESI-MS Found: m/z[M+H] 174

4) Production of 7'-nitro-1',2'-dihydro-3'H-spiro[cyclopropane-1,4'-isoquinolin]-3'-one

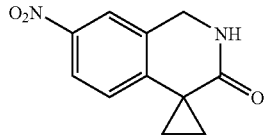

Potassium nitrate (1.3 g) was gradually added to a sulfuric acid (60 mL) solution of the compound (2.1 g) obtained in the above reaction 3), taking 5 minutes, and then stirred at room temperature for 10 minutes. The reaction liquid was poured into water with ice, the precipitated crystal was collected through filtration, and washed with water to give the entitled compound as a yellow solid (2.4 g).

$^1$H-NMR (CDCl$_3$) δ: 8.09 (1H, dd, J=8.8, 2.4 Hz), 8.01 (1H, t, J=2.4 Hz), 6.86 (1H, d, J=8.8 Hz), 6.30 (1H, s), 4.78 (2H, d, J=1.5 Hz), 2.01 (2H, q, J=4.1 Hz), 1.35 (2H, q, J=4.1 Hz).

ESI-MS Found: m/z[M+H] 219.

5) Production of 7'-nitro-1',2'-dihydro-3'H-spiro[cyclopropane-1,4'-isoquinoline]

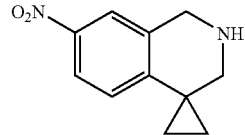

With cooling with ice, boron trifluoride/diethyl ether complex (6.3 g) was added to a tetrahydrofuran suspension of sodium borohydride (1.3 g), and stirred for 1 hour. A tetrahydrofuran solution (100 mL) of the compound (2.4 g) obtained in the above reaction 4) was added to the reaction liquid, and heated under reflux for 2 hours. The reaction liquid was cooled, and then neutralized with sodium bicarbonate water. The solvent was evaporated away under reduced pressure, the residue was dissolved in ethanol, 5 N hydrochloric acid was added thereto, and heated under reflux for 1 hour. The reaction liquid was cooled, then the solvent was evaporated away under reduced pressure, and the residue was neutralized with aqueous potassium carbonate solution. The aqueous layer was extracted with chloroform, the organic layer was dried with anhydrous magnesium sulfate, and the solvent was evaporated away under reduced pressure to give the entitled compound.

ESI-MS Found: m/z[M+H] 205.

6) Production of 2'-methyl-7'-nitro-2',3'-dihydro-1'H-spiro[cyclopropane-1,4'-isoquinoline]

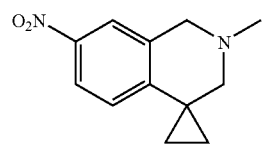

Sodium cyanoborohydride (1.5 g) was added to a methanol (50 mL) solution of the compound (2.3 g) obtained in the above reaction 5), aqueous 37% solution of formaldehyde (2.7 mL) and acetic acid (0.7 mL) and stirred at room temperature for 15 hours. The reaction liquid was neutralized with sodium bicarbonate water, and methanol was evaporated away under reduced pressure. The residue was diluted with water, and extracted three times with chloroform. The organic layer was dried with anhydrous magnesium sulfate, the solvent was evaporated away under reduced pressure, and the crude product was purified through silica gel column chromatography (hexane/ethyl acetate) to give the entitled compound as a colorless solid (1.7 g).

$^1$H-NMR (CDCl$_3$) δ: 7.97 (1H, dd, J=8.8, 2.4 Hz), 7.91 (1H, d, J=2.4 Hz), 6.78 (1H, d, J=8.8 Hz), 3.77 (2H, s), 2.57 (2H, s), 2.48 (3H, s), 1.16-1.12 (2H, m), 1.10-1.06 (2H, m).

ESI-MS Found: m/z[M+H] 219.

7) Production of 2'-methyl-2',3'-dihydro-1'H-spiro [cyclopropane-1,4'-isoquinolin]-7'-amine

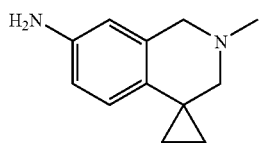

10% palladium/carbon (800 mg) was added to an ethanol (20 mL) solution of the compound (1.7 g) obtained in the above reaction 6), and stirred in 1-atmospheric hydrogen at room temperature for 15 hours. The palladium/carbon was removed through filtration, the filtrate was concentrated under reduced pressure, and the crude product was purified through basic silica gel column chromatography (hexane/ethyl acetate) to give the entitled compound as a colorless solid (1.1 g).

$^1$H-NMR (CDCl$_3$) δ: 6.50-6.48 (2H, m), 6.38-6.36 (1H, m), 3.61 (2H, s), 3.50 (2H, s), 2.49 (2H, s), 2.42 (3H, s), 0.91 (2H, dd, J=6.3, 4.6 Hz), 0.81 (2H, dd, J=6.3, 4.6 Hz).

ESI-MS Found: m/z[M+H] 189.

Production Example 24

Production of tert-butyl 6'-amino-3',4'-dihydro-2'H-spiro[cyclopropane-1,1'-isoquinoline]-2'-carboxylate 1) Production of 2'H-spiro[cyclopropane-1,1'-isoquinolin]-3'(4'H)-one

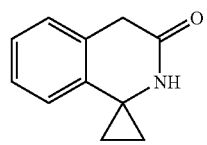

A diethyl ether solution (38 mL) of 2 M ethylmagnesium bromide was dropwise added at room temperature to a diethyl ether (200 mL) solution of methyl 2-cyanophenylacetate (10 g) and titanium tetraisopropoxide (17.9 g), and stirred for 1 hour. Aqueous 1 N hydrochloric acid solution was added to the reaction liquid, and the organic layer was separated. The aqueous layer was extracted with chloroform, the organic layer was washed with saturated saline water, and dried with anhydrous magnesium sulfate. The solvent was evaporated away under reduced pressure. The crude product was purified through basic silica gel column chromatography (hexane/ethyl acetate) to give the entitled compound as a colorless solid (1.8 g).

$^1$H-NMR (CDCl$_3$) δ: 7.39 (1H, s), 7.19-7.11 (2H, m), 6.80-6.76 (1H, m), 3.66 (2H, s), 1.24 (2H, t, J=2.2 Hz), 1.22 (2H, t, J=2.2 Hz).

ESI-MS Found: m/z[M+H] 174.

2) Production of 6'-nitro-2'H-spiro[cyclopropane-1, 1'-isoquinolin]-3'(4'H)-one

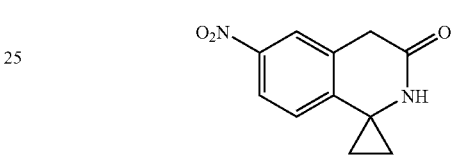

With cooling with ice, potassium nitrate (1.1 g) was gradually added to a sulfuric acid (20 mL) solution of the compound (1.8 g) obtained in the above reaction 1), and stirred at room temperature for 15 hours. The reaction liquid was neutralized with aqueous 28% ammonia, and extracted twice with chloroform. The organic layer was dried with anhydrous magnesium sulfate, and the solvent was evaporated away under reduced pressure. The resulting solid was washed with ethyl acetate to give the entitled compound as a yellow solid (1.3 g).

$^1$H-NMR (DMSO-d$_6$) δ: 8.26 (1H, s), 8.11 (1H, d, J=2.4 Hz), 8.02 (1H, dd, J=8.8, 2.4 Hz), 7.21 (1H, d, J=8.3 Hz), 3.73 (2H, s), 1.32 (2H, t, J=1.7 Hz), 1.31 (2H, t, J=1.7 Hz).

ESI-MS Found: m/z[M+H] 219.

3) Production of 6'-nitro-3',4'-dihydro-2'H-spiro[iso-quinoline-1,1'-isoquinoline]

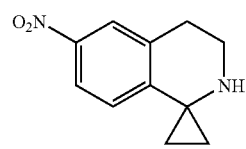

The entitled compound was obtained as a yellow oil (940 mg) according to the same method as in Production Example 21-5), for which, however, the compound obtained in the above reaction 2) was used in place of 7'-nitro-1',2'-dihydro-3'H-spiro[cyclopropane-1,4'-isoquinolin]-3'-one used in Production Example 23-5).

$^1$H-NMR (CDCl$_3$) δ: 7.98-7.93 (2H, m), 6.73 (1H, d, J=8.4 Hz), 3.23 (2H, t, J=6.0 Hz), 2.98 (2H, t, J=6.0 Hz), 1.28-1.24 (2H, m), 1.18-1.15 (2H, m).

ESI-MS Found: m/z[M+H] 205.

4) Production of tert-butyl 6'-nitro-3',4'-dihydro-2'H-spiro[cyclopropane-1,1'-isoquinoline]-2'-carboxylate

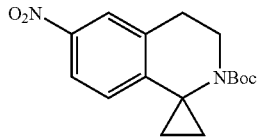

Di-tert-butyl dicarboxylate anhydride (0.06 mL) and triethylamine (0.05 mL) were added to a chloroform (2 mL) solution of the compound (38 mg) obtained in the above reaction 3), and stirred at room temperature for 18 hours. The reaction liquid was concentrated under reduced pressure, and the resulting crude product was purified through silica gel column chromatography (hexane/ethyl acetate) to give the entitled compound as a yellow oil (35 mg).

ESI-MS Found: m/z[M+H] 305.

5) Production of tert-butyl 6'-amino-3',4'-dihydro-2'H-spiro[cyclopropane-1,1'-isoquinoline]-2'-carboxylate

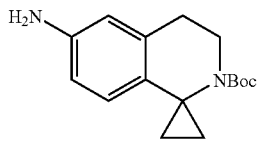

The entitled compound was obtained as a yellow solid (27 mg) according to the same method as in Production Example 23-7), for which, however, the compound (35 mg) obtained in the above reaction 3) was used in place of 2'-methyl-7'-nitro-2',3'-dihydro-1'H-spiro[cyclopropane-1,4'-isoquinoline] used in Production Example 23-7).

$^1$H-NMR (CDCl$_3$) δ: 6.52 (1H, d, J=8.2 Hz), 6.43-6.39 (2H, m), 3.72 (2H, t, J=6.3 Hz), 2.84 (2H, t, J=6.3 Hz), 1.37 (9H, s), 1.31-1.26 (2H, m), 1.14-1.10 (2H, m).

ESI-MS Found: m/z[M+H] 275

Production Example 25

Production of 2-methyl-1,2,3,4-tetrahydroisoquinolin-7-amine

1) Production of 7-nitro-1,2,3,4-tetrahydroisoquinoline monohydrochloride

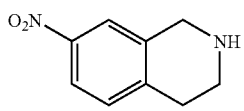

7-nitro-1,2,3,4-tetrahydroisoquinoline was obtained according to the same method as in Production Example 24-2), for which, however, 1,2,3,4-tetrahydroisoquinoline was used in place of 2'H-spiro[cyclopropane-1,1'-isoquinolin]-3'(4'H)-one used in Production Example 24-2). This was dissolved in ethyl acetate, then 4 N hydrochloric acid/ethyl acetate was added thereto, the precipitated solid was collected through filtration, and washed with ethyl acetate. This was recrystallized from methanol to give the entitled compound as a yellow solid (5.6 g).

$^1$H-NMR (DMSO-d$_6$) δ: 9.48 (2H, s), 8.21 (1H, d, J=2.0 Hz), 8.11 (1H, dd, J=8.3, 2.0 Hz), 7.52 (1H, d, J=8.3 Hz), 3.42-3.33 (4H, m), 3.14-3.10 (2H, m).

ESI-MS Found: m/z[M+H] 180.

2) Production of 2-methyl-7-nitro-1,2,3,4-tetrahydroisoquinoline

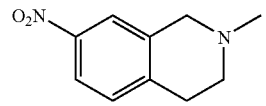

Sodium cyanoborohydride (5.9 g) was added to a methanol (450 mL) solution of the compound (10 g) obtained in the above reaction 1), aqueous 37% formaldehyde solution (10.4 mL) and acetic acid (4 mL), and stirred at 50° C. for 15 hours. The precipitated solid was collected through filtration, and washed with methanol. The resulting crude product was purified through basic silica gel column chromatography (hexane/ethyl acetate) to give the entitled compound as a colorless solid (8.7 g).

$^1$H-NMR (CDCl$_3$) δ: 7.99 (1H, dd, J=8.5, 2.0 Hz), 7.92 (1H, d, J=2.0 Hz), 7.26 (1H, d, J=8.5 Hz), 3.65 (2H, s), 3.01 (2H, t, J=5.9 Hz), 2.73 (2H, t, J=5.9 Hz), 2.49 (3H, s).

ESI-MS Found: m/z[M+H] 193.

3) Production of 2-methyl-1,2,3,4-tetrahydroisoquinolin-7-amine

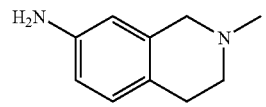

The entitled compound was obtained as a yellow solid (7.3 g) according to the same method as in Production Example 23-7), for which, however, the compound (8.7 g) obtained in the above reaction 2) was used in place of 2'-methyl-7'-nitro-2',3'-dihydro-1'H-spiro[cyclopropane-1,4'-isoquinoline] used in Production Example 23-7).

$^1$H-NMR (CDCl$_3$) δ: 6.89 (1H, d, J=8.3 Hz), 6.51 (1H, dd, J=8.3, 2.0 Hz), 6.36 (1H, d, J=2.0 Hz), 3.51 (2H, brs), 3.48 (2H, s), 2.80 (2H, t, J=6.1 Hz), 2.64 (2H, t, J=6.1 Hz), 2.43 (3H, s).

ESI-MS Found: m/z[M+H] 164.

Example 1

Production of 6'-(2-allyl-6-{[4-(4-methylpiperazin-1-yl)phenyl]amino}-3-oxo-2,3-dihydro-1H-pyrazolo[3,4-d]pyrimidin-1-yl)-2H-1,2'-bipyridin-2-one

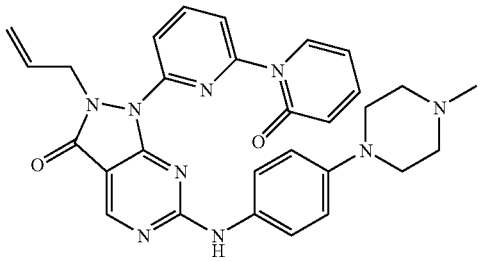

1) Production of 6'-bromo-2H-1,2'-bipyridin-2-one 2,6-dibromopyridine (4.74 g), 2-hydroxypyridine (2.85 g), potassium carbonate (4.15 g) and N-methylpyrrolidone (1 mL) were stirred at 150° C. for 6 hours. The reaction solution was cooled to room temperature, then ethyl acetate and aqueous sodium hydrogencarbonate solution were added thereto, the insoluble matter was removed through Celite filtration, and the organic layer was separated. This was washed with saturated saline water, dried with anhydrous magnesium sulfate, and the solvent was evaporated away under reduced pressure. The crude product was purified through silica gel column chromatography (hexane/ethyl acetate) to give the entitled compound as a white solid (1.63 g).

$^1$H-NMR (400 MHz, CDCl$_3$) δ: 8.02 (1H, d, J=7.3 Hz), 7.91 (1H, dd, J=7.6, 1.7 Hz), 7.70 (1H, t, J=7.8 Hz), 7.51 (1H, d, J=7.8 Hz), 7.41-7.37 (1H, m), 6.63 (1H, dd, J=9.3, 1.5 Hz), 6.33-6.29 (1H, m).

2) Production of 6'-[2-allyl-6-(methylthio)-3-oxo-2,3-dihydro-1H-pyrazolo[3,4-d]pyrimidin-1-yl]-2H-1,2'-bipyridin-2-one The entitled compound was obtained as a white oily substance (1.11 g) in the same manner as in Production Example 12-1, for which, however, 6'-bromo-2H-1,2'-bipyridin-2-one was used in place of 2-iodopyridine used in Production Example 12-1.

$^1$H-NMR (400 MHz, CDCl$_3$) δ: 8.95 (1H, s), 8.05 (1H, t, J=8.0 Hz), 7.94 (2H, d, J=8.3 Hz), 7.83 (1H, dd, J=7.6, 1.7 Hz), 7.44-7.40 (1H, m), 6.68 (1H, d, J=9.3 Hz), 6.34-6.30 (1H, m), 5.68 (1H, ddt, J=17.1, 10.2, 6.3 Hz), 5.07 (1H, dd, J=10.2, 1.0 Hz), 4.99 (1H, dd, J=17.1, 1.0 Hz), 4.79 (2H, d, J=6.3 Hz), 2.61 (3H, s).

3) Production of 6-(2-allyl-6-{[4-(4-methylpiperazin-1-yl)phenyl]amino}-3-oxo-2,3-dihydro-1H-pyrazolo[3,4-d]pyrimidin-1-yl)-2H-1,2'-bipyridin-2-one The entitled compound was obtained as a yellow solid (62.3 mg) in the same manner as in Production Example 12-2, for which, however, 4-(4-methylpiperazin-1-yl)aniline was used in place of [5-amino-2-(4-methylpiperazin-1-yl)phenyl]methanol used in Production Example 12-2, and 6'-[2-allyl-6-(methylthio)-3-oxo-2,3-dihydro-1H-pyrazolo[3,4-d]pyrimidin-1-yl]-2H-1,2'-bipyridin-2-one was used in place of 2-allyl-6-(methylthio)-1-pyridin-2-yl-3H-pyrazolo[3,4-d]pyrimidin-3-one.

$^1$H-NMR (400 MHz, CDCl$_3$) δ: 8.83 (1H, s), 7.98 (1H, dd, J=9.3, 6.8 Hz), 7.93-7.90 (2H, m), 7.86 (1H, dd, J=6.6, 1.7 Hz), 7.47-7.39 (4H, m), 6.93 (2H, d, J=9.3 Hz), 6.67 (1H, d, J=8.8 Hz), 6.31 (1H, t, J=6.8 Hz), 5.68 (1H, ddt, J=17.1, 10.5, 6.3 Hz), 5.04 (1H, d, J=10.2 Hz), 4.99 (1H, d, J=17.1 Hz), 4.73 (2H, d, J=6.3 Hz), 3.21 (4H, t, J=5.1 Hz), 2.60 (4H, t, J=5.1 Hz), 2.37 (3H, s).

ESI-MS Found: m/z[M+H] 536.

Example 2

Production of 6'-[2-allyl-6-({4-[(3R)-3-(dimethylamino)pyrrolidin-1-yl]phenyl}amino)-3-oxo-2,3-dihydro-1H-pyrazolo[3,4-d]pyrimidin-1-yl]-2H-1,2'-bipyridin-2-one

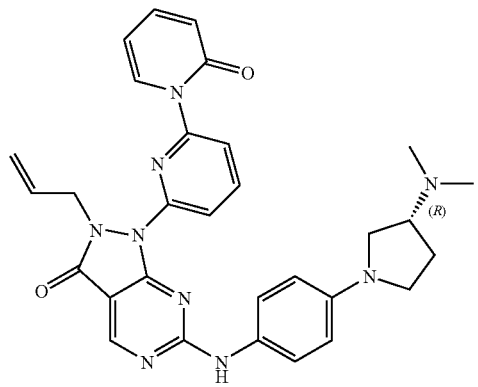

The entitled compound was obtained as a yellow solid (35.5 mg) in the same manner as in Production Example 12-2, for which, however, (3R)-1-(4-aminophenyl)-N,N-dimethylpyrrolidin-3-amine was used in place of [5-amino-2-(4-methylpiperazin-1-yl)phenyl]methanol used in Production Example 12-2, and 6'-[2-allyl-6-(methylthio)-3-oxo-2,3-dihydro-1H-pyrazolo[3,4-d]pyrimidin-1-yl]-2H-1,2'-bipyridin-2-one was used in place of 2-allyl-6-(methylthio)-1-pyridin-2-yl-3H-pyrazolo[3,4-d]pyrimidin-3-one.

$^1$H-NMR (400 MHz, CDCl$_3$) δ: 8.81 (1H, s), 7.96-7.85 (4H, m), 7.43-7.35 (4H, m), 6.67 (1H, d, J=9.3 Hz), 6.53 (2H, d, J=9.3 Hz), 6.30 (1H, t, J=6.8 Hz), 5.67 (1H, ddt, J=17.1, 10.2, 6.3 Hz), 5.04 (1H, d, J=10.2 Hz), 4.99 (1H, dd, J=17.1, 1.5 Hz), 4.72 (2H, d, J=6.3 Hz), 3.53-3.43 (2H, m), 3.39-3.31 (1H, m), 3.17 (1H, t, J=8.3 Hz), 2.87 (1H, t, J=8.5 Hz), 2.34 (6H, s), 2.28-2.20 (1H, m), 2.00-1.92 (1H, m).

ESI-MS Found: m/z[M+H] 550.

Example 3

Production of 6'-[2-allyl-6-({4-[(3S)-3-(dimethylamino)pyrrolidin-1-yl]phenyl}amino)-3-oxo-2,3-dihydro-1H-pyrazolo[3,4-d]pyrimidin-1-yl]-2H-1,2'-bipyridin-2-one

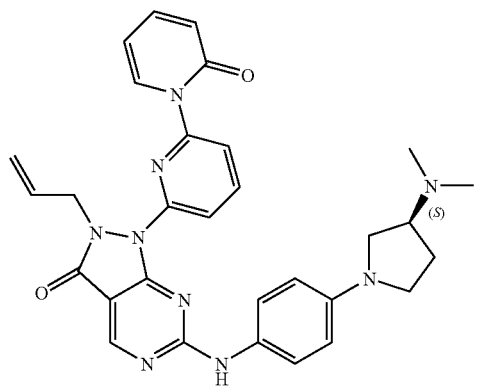

The entitled compound was obtained as a yellow solid (36.7 mg) in the same manner as in Production Example 12-2, for which, however, (3S)-1-(4-aminophenyl)-N,N-dimethylpyrrolidin-3-amine was used in place of [5-amino-2-(4-methylpiperazin-1-yl)phenyl]methanol used in Production Example 12-2, and 6'-[2-allyl-6-(methylthio)-3-oxo-2,3-dihydro-1H-pyrazolo[3,4-d]pyrimidin-1-yl]-2H-1,2'-bipyridin-2-one was used in place of 2-allyl-6-(methylthio)-1-pyridin-2-yl-3H-pyrazolo[3,4-d]pyrimidin-3-one.

1H-NMR (400 MHz, CDCl3) δ: 8.81 (1H, s), 7.96-7.85 (4H, m), 7.43-7.35 (4H, m), 6.67 (1H, d, J=9.3 Hz), 6.53 (2H, d, J=9.3 Hz), 6.32-6.28 (1H, m), 5.67 (1H, ddt, J=17.1, 10.2, 6.3 Hz), 5.04 (1H, d, J=10.2 Hz), 4.99 (1H, dd, J=17.1, 1.0 Hz), 4.72 (2H, d, J=6.3 Hz), 3.53-3.43 (2H, m), 3.35 (1H, dd, J=16.3, 9.0 Hz), 3.17 (1H, t, J=8.3 Hz), 2.87 (1H, t, J=8.5 Hz), 2.33 (6H, s), 2.28-2.20 (1H, m), 2.00-1.90 (1H, m).

ESI-MS Found: m/z[M+H] 550.

Example 4

Production of 2-allyl-1-[3-fluoro-5-(2-oxopyridin-1 (2H)-yl)phenyl]-6-{[4-(4-methylpiperazin-1-yl)phenyl]amino}-1,2-dihydro-3H-pyrazolo[3,4-d]pyrimidin-3-one

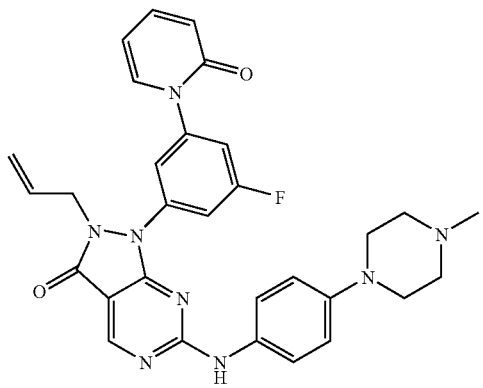

1) Production of 2-allyl-1-(3-bromo-5-fluorophenyl)-6-(methylthio)-1,2-dihydro-3H-pyrazolo[3,4-d]pyrimidin-3-one The entitled compound was obtained as a white oily substance (500 mg) in the same manner as in Production Example 11, for which, however, (3-bromo-5-fluorophenyl) boronic acid was used in place of [3-(methoxycarbonyl)]phenylboronic acid used in Production Example 11.

1H-NMR (400 MHz, CDCl3) δ: 8.91 (1H, s), 7.44-7.42 (1H, m), 7.28 (1H, dt, J=8.0, 2.1 Hz), 7.18 (1H, dt, J=8.9, 2.1 Hz), 5.73-5.63 (1H, m), 5.16 (1H, dd, J=10.2, 1.0 Hz), 5.04 (1H, dd, J=17.1, 1.0 Hz), 4.45 (2H, d, J=5.9 Hz), 2.55 (3H, s).

2) Production of 2-allyl-1-[3-fluoro-5-(2-oxopyridin-1 (2H)-yl)phenyl]-6-(methylthio)-1,2-dihydro-3H-pyrazolo[3,4-d]pyrimidin-3-one 2-Hydroxypyridine (48.1 mg), copper iodide (48.2 mg), potassium carbonate (35.0 mg), and trans-(1R,2R)—N,N'-bismethyl-1,2-cyclohexanediamine (39.9 μL) were added to a dioxane solution (5 mL) of 2-allyl-1-(3-bromo-5-fluorophenyl)-6-(methylthio)-1,2-dihydro-3H-pyrazolo[3,4-d]pyrimidin-3-one (100 mg), and stirred overnight in a sealed tube under heat at 100° C.

The reaction liquid was cooled, then aqueous ammonia solution was added thereto, and extracted three times with chloroform. The organic layer was washed with saturated saline water, dried with anhydrous magnesium sulfate, filtered, and the solvent was evaporated away. The resulting crude product was purified through silica gel column chromatography to give the entitled compound as a yellow oily substance (91 mg).

1H-NMR (400 MHz, CDCl3) δ: 8.91 (1H, s), 7.45-7.41 (1H, m), 7.38 (1H, dt, J=8.9, 2.1 Hz), 7.34 (1H, dd, J=6.8, 1.5 Hz), 7.30-7.29 (1H, m), 7.18 (1H, dt, J=8.9, 2.1 Hz), 6.67 (1H, d, J=9.3 Hz), 6.30 (1H, td, J=6.7, 1.1 Hz), 5.73-5.63 (1H, m), 5.15 (1H, dd, J=10.2, 1.0 Hz), 5.08 (1H, dd, J=17.1, 1.0 Hz), 4.53 (2H, d, J=5.9 Hz), 2.57 (3H, s).

3) Production of 2-allyl-1-[3-fluoro-5-(2-oxopyridin-1(2H)-yl)phenyl]-6-{[4-(4-methylpiperazin-1-yl)phenyl]amino}-1,2-dihydro-3H-pyrazolo[3,4-d]pyrimidin-3-one The entitled compound was obtained as a yellow solid (68.4 mg) in the same manner as in Production Example 12-2, for which, however, 4-(4-methylpiperazin-1-yl)aniline was used in place of [5-amino-2-(4-methylpiperazin-1-yl)phenyl]methanol used in Production Example 12-2, and 2-allyl-1-[3-fluoro-5-(2-oxopyridin-1(2H)-yl)phenyl]-6-(methylthio)-1,2-dihydro-3H-pyrazolo[3,4-d]pyrimidin-3-one was used in place of 2-allyl-6-(methylthio)-1-pyridin-2-yl-3H-pyrazolo[3,4-d]pyrimidin-3-one.

1H-NMR (400 MHz, CDCl3) δ: 8.80 (1H, s), 7.46-7.29 (7H, m), 7.15 (1H, dt, J=8.8, 2.0 Hz), 6.90-6.87 (2H, m), 6.68 (1H, d, J=9.3 Hz), 6.28 (1H, t, J=6.1 Hz), 5.74-5.64 (1H, m), 5.13 (2H, d, J=10.2 Hz), 5.09 (2H, dd, J=17.1, 1.5 Hz), 4.46 (2H, d, J=5.9 Hz), 3.21-3.18 (4H, m), 2.62-2.58 (4H, m), 2.38 (3H, s).

ESI-MS Found: m/z[M+H] 553.

Example 5

Production of 6'-(2-allyl-6-{[4-(4-methylpiperazin-1-yl)phenyl]amino}-3-oxo-2,3-dihydro-1H-pyrazolo[3,4-d]pyrimidin-1-yl)-5-fluoro-2H-1,2'-bipyridin-2-one

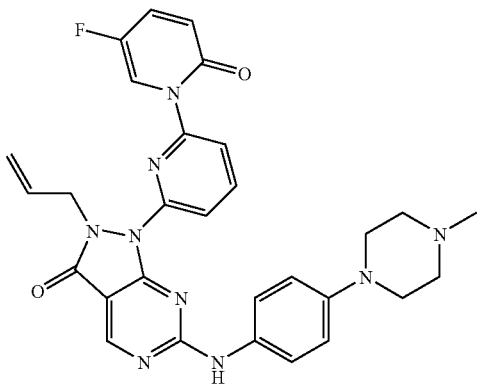

1) Production of 2-allyl-1-(6-bromopyridin-2-yl)-6-(methylthio)-1,2-dihydro-3H-pyrazolo[3,4-d]pyrimidin-3-one The entitled compound was obtained as a white solid substance (2.94 g) in the same manner as in Production Example 12-1, for which, however, 2,6-dibromopyridine was used in place of 2-iodopyridine used in Production Example 12-1.

1H-NMR (400 MHz, CDCl3) δ: 8.94 (1H, s), 7.95 (1H, d, J=7.8 Hz), 7.73 (1H, t, J=8.0 Hz), 7.43 (1H, d, J=7.8 Hz), 5.69

(1H, ddt, J=17.1, 10.2, 6.3 Hz), 5.06 (1H, dd, J=10.2, 1.2 Hz), 5.00 (1H, d, J=17.1 Hz), 4.88 (2H, d, J=6.3 Hz), 2.60 (3H, s).

2) Production of 6'-[2-allyl-6-(methylthio)-3-oxo-2,3-dihydro-1H-pyrazolo[3,4-d]pyrimidin-1-yl]-5-fluoro-2H-1,2'-bipyridin-2-one The entitled compound was obtained as a white oily substance (170 mg) in the same manner as in Example 4-2, for which, however, the compound obtained in the above reaction was used in place of 2-allyl-1-(3-bromo-5-fluorophenyl)-6-(methylthio)-1,2-dihydro-3H-pyrazolo[3,4-d]pyrimidin-3-one used in Example 4-2, and 5-fluoro-2-hydroxypyridine was used in place of 2-hydroxypyridine.
$^1$H-NMR (400 MHz, CDCl$_3$) δ: 8.96 (1H, s), 8.07 (1H, s), 8.06 (1H, d, J=3.4 Hz), 7.93-7.89 (2H, m), 7.41-7.36 (1H, m), 6.66 (1H, dd, J=10.2, 5.4 Hz), 5.69 (1H, ddt, J=17.1, 10.2, 6.3 Hz), 5.08 (1H, d, J=10.2 Hz), 4.99 (1H, d, J=17.1 Hz), 4.77 (2H, d, J=6.3 Hz), 2.61 (3H, s).

3) Production of 6'-(2-allyl-6-{[4-(4-methylpiperazin-1-yl)phenyl]amino}-3-oxo-2,3-dihydro-1H-pyrazolo[3,4-d]pyrimidin-1-yl)-5-fluoro-2H-1,2'-bipyridin-2-one The entitled compound was obtained as a yellow solid (23.6 mg) in the same manner as in Production Example 12-2, for which, however, 4-(4-methylpiperazin-1-yl)aniline was used in place of [5-amino-2-(4-methylpiperazin-1-yl)phenyl]methanol used in Production Example 12-2, and 6'-[2-allyl-6-(methylthio)-3-oxo-2,3-dihydro-1H-pyrazolo[3,4-d]pyrimidin-1-yl]-5-fluoro-2H-1,2'-bipyridin-2-one was used in place of 2-allyl-6-(methylthio)-1-pyridin-2-yl-3H-pyrazolo[3,4-d]pyrimidin-3-one.
$^1$H-NMR (400 MHz, CDCl$_3$) δ: 8.83 (1H, s), 8.02 (1H, dd, J=7.8, 1.0 Hz), 7.98 (1H, t, J=7.8 Hz), 7.94-7.89 (2H, m), 7.47-7.42 (2H, m), 7.40-7.35 (1H, m), 6.95-6.90 (2H, m), 6.66 (1H, dd, J=10.2, 5.4 Hz), 5.74-5.64 (1H, m), 5.06 (1H, dd, J=10.2, 1.0 Hz), 4.99 (1H, dd, J=17.1, 1.0 Hz), 4.71 (2H, d, J=6.3 Hz), 3.24-3.20 (4H, m), 2.64-2.59 (4H, m), 2.38 (3H, s).
ESI-MS Found: m/z[M+H] 554.

Example 6

Production of 6'-[2-allyl-6-({4-[(tert-butylamino)methyl]phenyl}amino)-3-oxo-2,3-dihydro-1H-pyrazolo[3,4-d]pyrimidin-1-yl]-2H-1,2'-bipyridin-2-one Chloromethanesulfonic acid (37 μL) was added to a tetrahydrofuran solution (10 mL) of 6'-[2-allyl-6-{[4-(hydroxymethyl)phenyl]amino}-3-oxo-2,3-dihydro-1H-pyrazolo[3,4-d]pyrimidin-1-yl]-2H-1,2'-bipyridin-2-one (110 mg) and triethylamine (164 μL), and stirred at room temperature for 1 hour, then tert-butylamine (500 μL) was added to the reaction liquid, and stirred for 6 hours. Chloroform and aqueous sodium hydrogencarbonate solution were added to the reaction liquid, and the organic layer was separated. The organic layer was washed with saturated saline water, then dried with anhydrous magnesium sulfate, filtered, the solvent was evaporated away, and the resulting crude product was purified through basic silica gel column chromatography (hexane-ethyl acetate/ethanol (19/1) mixture) to give the entitled compound as a white solid substance (9.2 mg).
1H-NMR (400 MHz, CDCl3) δ: 8.86 (1H, s), 8.03 (1H, t, J=8.0 Hz), 7.94-7.91 (2H, m), 7.88-7.85 (1H, m), 7.54 (3H, d, J=8.3 Hz), 7.44-7.39 (1H, m), 7.33 (2H, d, J=8.3 Hz), 6.68 (1H, d, J=8.8 Hz), 6.32 (1H, t, J=6.8 Hz), 5.68 (1H, ddt, J=17.1, 10.2, 6.3 Hz), 5.05 (1H, d, J=10.2 Hz), 5.00 (1H, d, J=17.1 Hz), 4.74 (2H, d, J=6.3 Hz), 3.73 (2H, s), 1.20 (9H, s).
ESI-MS Found: m/z[M+H] 523.

Compounds of the following Examples 7 to 42 were produced in the same manner as in the above-mentioned Examples and using the corresponding starting materials.

Example 7

2-Allyl-6-{[4-(4-methylpiperazin-1-yl)phenyl]amino}-1-[3-(2-oxopyridin-1(2H)-yl)phenyl]-1,2-dihydro-3H-pyrazolo[3,4-d]pyrimidin-3-one

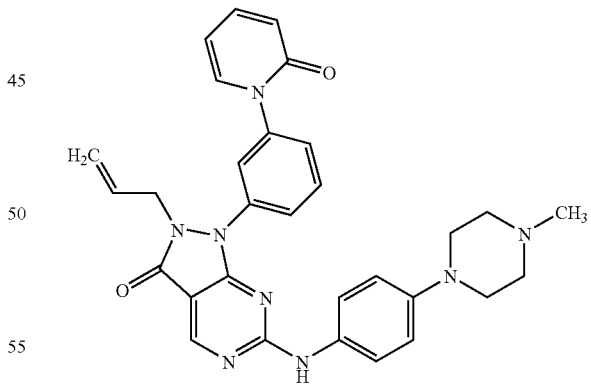

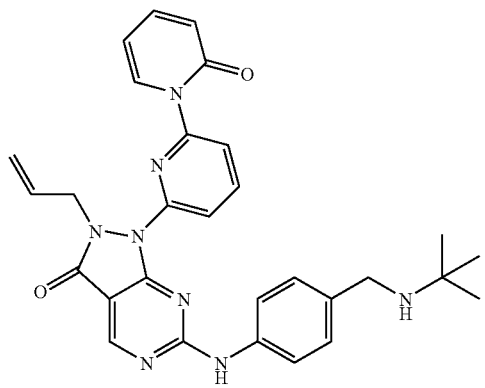

$^1$H-NMR (400 MHz, CDCl$_3$) δ: 8.80 (1H, s), 7.62 (1H, t, J=8.0 Hz), 7.55-7.51 (2H, m), 7.46-7.38 (4H, m), 7.36-7.32 (1H, m), 6.87-6.83 (2H, m), 6.68 (1H, d, J=9.3 Hz), 6.28 (1H, td, J=6.7, 1.1 Hz), 5.75-5.64 (1H, m), 5.12 (1H, dd, J=10.2, 1.0 Hz), 5.05 (1H, dd, J=17.1, 1.0 Hz), 4.45 (2H, d, J=6.3 Hz), 3.25-3.19 (4H, m), 2.71-2.63 (4H, m), 2.42 (3H, s).
ESI-MS Found: m/z[M+H] 535.

Example 8

2-Allyl-6-{[4-(1-methylpiperidin-1-yl)phenyl]amino}-1-[3-(2-oxopyridin-1(2H)-yl)phenyl]-1,2-dihydro-3H-pyrazolo[3,4-d]pyrimidin-3-one

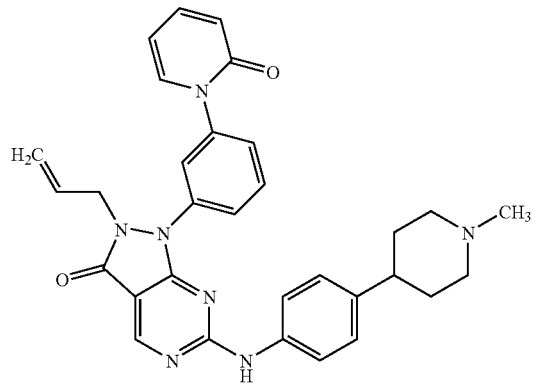

$^1$H-NMR (400 MHz, CDCl$_3$) δ: 8.83 (1H, s), 7.64 (1H, t, J=7.8 Hz), 7.60-7.56 (1H, m), 7.54-7.42 (5H, m), 7.42-7.36 (2H, m), 7.17-7.12 (2H, m), 6.70 (1H, d, J=9.3 Hz), 6.29 (1H, td, J=6.8, 1.5 Hz), 5.75-5.65 (1H, m), 5.12 (1H, dd, J=10.2, 1.0 Hz), 5.06 (1H, dd, J=17.1, 1.0 Hz), 4.47 (2H, d, J=5.9 Hz), 3.10-3.03 (2H, m), 2.52-2.43 (1H, m), 2.39 (3H, s), 2.20-2.10 (2H, m), 1.88-1.81 (4H, m).

ESI-MS Found: m/z[M+H] 534.

Example 9

6'-(2-Allyl-6-{[4-(1-methylpiperidin-4-yl)phenyl]amino}-3-oxo-2,3-dihydro-1H-pyrazolo[3,4-d]pyrimidin-1-yl)-2H-1,2'-bipyridin-2-one

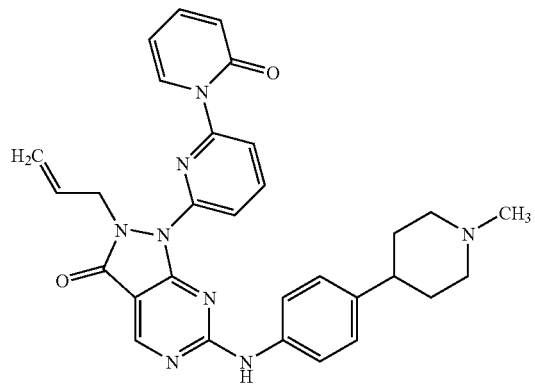

$^1$H-NMR (400 MHz, CDCl$_3$) δ: 8.86 (1H, s), 7.99 (1H, dd, J=9.0, 6.6 Hz), 7.94-7.91 (2H, m), 7.86 (1H, dd, J=7.6, 1.7 Hz), 7.52 (2H, d, J=8.8 Hz), 7.44-7.39 (2H, m), 7.22 (2H, d, J=8.8 Hz), 6.68 (1H, d, J=8.8 Hz), 6.33-6.29 (1H, m), 5.68 (1H, ddt, J=17.1, 10.2, 6.3 Hz), 5.05 (1H, d, J=10.2 Hz), 4.99 (1H, dd, J=17.1, 1.0 Hz), 4.74 (2H, d, J=6.3 Hz), 2.99 (2H, d, J=11.7 Hz), 2.53-2.45 (1H, m), 2.34 (3H, s), 2.09-2.03 (2H, m), 1.86-1.78 (4H, m).

ESI-MS Found: m/z[M+H] 535.

Example 10

6'-(2-Allyl-6-{[3-(hydroxymethyl)-4-(4-methylpiperazin-1-yl)phenyl]amino}-3-oxo-2,3-dihydro-1H-pyrazolo[3,4-d]pyrimidin-1-yl)-2H-1,2'-bipyridin-2-one

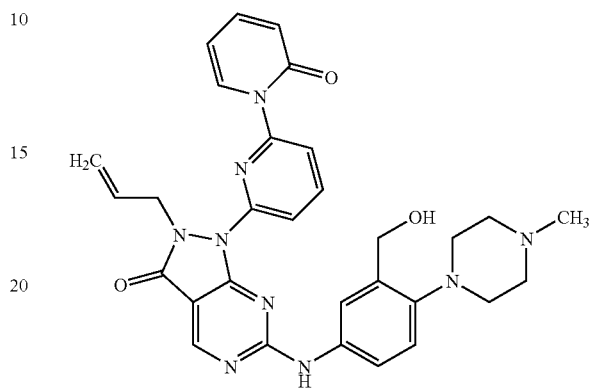

$^1$H-NMR (400 MHz, CDCl$_3$) δ: 8.86 (1H, s), 8.05 (1H, t, J=8.0 Hz), 7.93 (2H, dd, J=7.6, 4.1 Hz), 7.84 (1H, dd, J=6.8, 2.0 Hz), 7.58 (1H, s), 7.45-7.36 (2H, m), 7.21 (1H, d, J=8.8 Hz), 6.68 (1H, d, J=8.8 Hz), 6.31 (1H, t, J=6.8 Hz), 5.68 (1H, ddt, J=17.1, 10.2, 6.3 Hz), 5.05 (1H, d, J=10.2 Hz), 4.99 (1H, d, J=17.1 Hz), 4.80 (2H, s), 4.74 (2H, d, J=6.3 Hz), 3.02 (4H, t, J=4.9 Hz), 2.63 (4H, brs), 2.38 (3H, s).

ESI-MS Found: m/z[M+H] 566.

Example 11

6'-(2-Allyl-6-{[3-methyl-4-(4-methylpiperazin-1-yl)phenyl]amino}-3-oxo-2,3-dihydro-1H-pyrazolo[3,4-d]pyrimidin-1-yl)-2H-1,2'-bipyridin-2-one

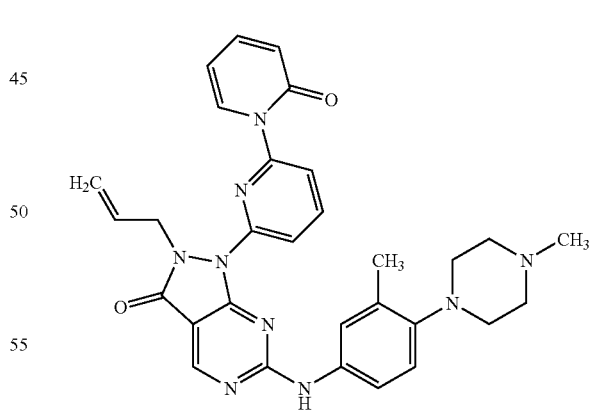

$^1$H-NMR (400 MHz, CDCl$_3$) δ: 8.84 (1H, s), 8.01-7.91 (3H, m), 7.87-7.85 (1H, m), 7.48 (1H, brs), 7.44-7.39 (1H, m), 731 (1H, dd, J=8.8, 2.4 Hz), 7.02 (1H, d, J=8.8 Hz), 6.67 (1H, d, J=9.3 Hz), 6.33-6.29 (1H, m), 5.68 (1H, ddt, J=17.1, 10.2, 6.3 Hz), 5.04 (1H, dd, J=10.2, 1.5 Hz), 4.99 (1H, dd, J=17.1, 1.5 Hz), 4.74 (2H, d, J=6.3 Hz), 2.94 (4H, t, J=4.6 Hz), 2.60 (4H, brs), 2.38 (3H, s), 2.34 (3H, s).

ESI-MS Found: m/z[M+H] 550.

Example 12

6'-(2-Allyl-6-{[4-(4-methylpiperazin-1-yl)phenyl]amino}-3-oxo-2,3-dihydro-1H-pyrazolo[3,4-d]pyrimidin-1-yl)-3-methyl-2H-1,2'-bipyridin-2-one

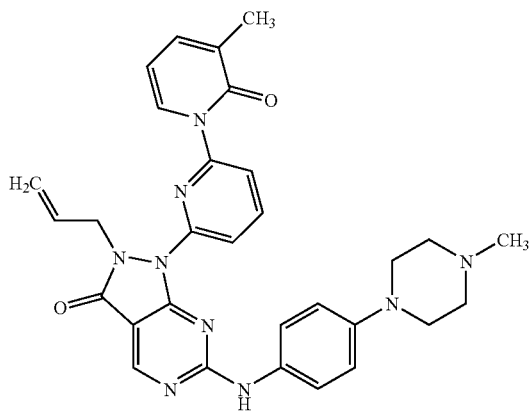

$^1$H-NMR (400 MHz, CDCl$_3$) δ: 8.83 (1H, s), 7.99-7.94 (1H, m), 7.92-7.87 (2H, m), 7.75-7.72 (1H, m), 7.48-7.43 (2H, m), 7.30-7.27 (1H, m), 6.94-6.90 (2H, m), 6.23 (1H, t, J=6.8 Hz), 5.73-5.63 (1H, m), 5.04 (1H, dd, J=10.2, 1.0 Hz), 4.99 (1H, dd, J=17.3, 1.0 Hz), 4.72 (2H, d, J=5.9 Hz), 3.24-3.19 (4H, m), 2.64-2.58 (4H, m), 2.38 (3H, s), 2.21 (3H, s).

ESI-MS Found: m/z[M+H] 550.

Example 13

6'-(2-Allyl-6-{[4-(4-methylpiperazin-1-yl)phenyl]amino}-3-oxo-2,3-dihydro-1H-pyrazolo[3,4-d]pyrimidin-1-yl)-4-methyl-2H-1,2'-bipyridin-2-one

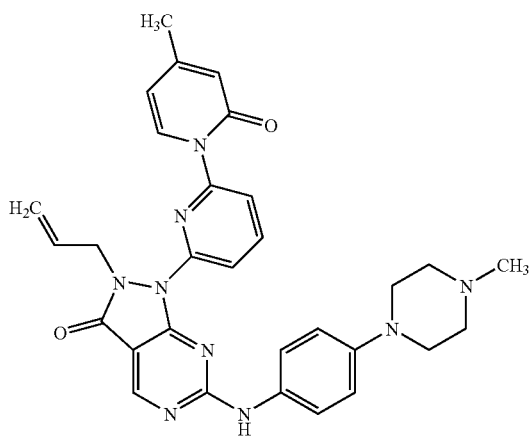

$^1$H-NMR (400 MHz, CDCl$_3$) δ: 8.83 (1H, s), 7.98-7.92 (2H, m), 7.88 (1H, dd, J=7.1, 1.6 Hz), 7.79 (1H, d, J=7.3 Hz), 7.48-7.43 (2H, m), 6.95-6.90 (2H, m), 6.47 (1H, s), 6.15 (1H, dd, J=7.3, 1.6 Hz), 5.72-5.62 (1H, m), 5.04 (1H, dd, J=10.2, 1.0 Hz), 4.98 (1H, dd, J=17.1, 1.0 Hz), 4.72 (2H, d, J=6.3 Hz), 3.24-3.18 (4H, m), 2.65-2.59 (4H, m), 2.37 (3H, s), 2.25 (3H, s).

ESI-MS Found: m/z[M+H] 550.

Example 14

6'-(2-Allyl-6-{[4-(4-methylpiperazin-1-yl)phenyl]amino}-3-oxo-2,3-dihydro-1H-pyrazolo[3,4-d]pyrimidin-1-yl)-5-methyl-2H-1,2'-bipyridin-2-one

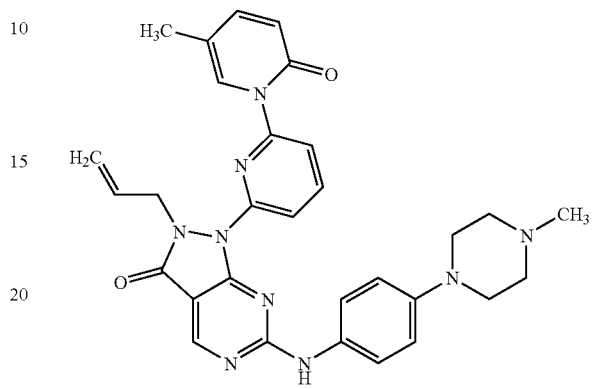

$^1$H-NMR (400 MHz, CDCl$_3$) δ: 8.84 (1H, s), 7.97 (1H, t, J=7.8 Hz), 7.91-7.87 (2H, m), 7.61 (1H, s), 7.48-7.43 (2H, m), 7.29-7.27 (1H, m), 6.94-6.90 (2H, m), 6.62 (1H, d, J=9.8 Hz), 5.74-5.64 (1H, m), 5.05 (1H, dd, J=10.0, 1.0 Hz), 5.00 (1H, dd, J=17.1, 1.0 Hz), 4.73 (2H, d, J=6.3 Hz), 3.24-3.19 (4H, m), 2.64-2.59 (4H, m), 2.38 (3H, s), 2.13 (3H, s).

ESI-MS Found: m/z[M+H] 550.

Example 15

6'-(2-Allyl-6-{[4-(4-methylpiperazin-1-yl)phenyl]amino}-3-oxo-2,3-dihydro-1H-pyrazolo[3,4-d]pyrimidin-1-yl)-3-methoxy-2H-1,2'-bipyridin-2-one

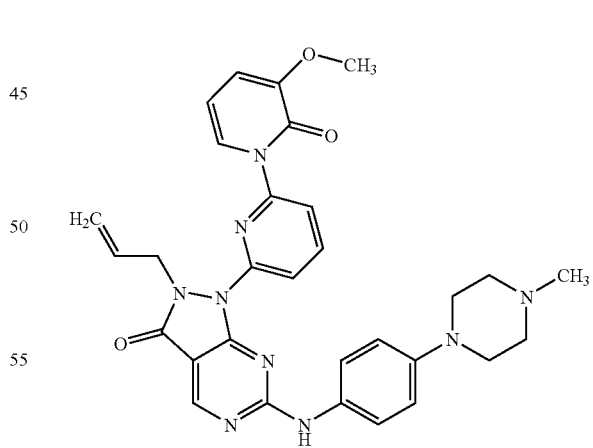

$^1$H-NMR (400 MHz, CDCl$_3$) δ: 8.83 (1H, s), 8.01-7.96 (1H, m), 7.93-7.87 (2H, m), 7.49-7.44 (3H, m), 6.95-6.90 (2H, m), 6.67 (1H, dd, J=7.3, 1.5 Hz), 6.24 (1H, t, J=7.3 Hz), 5.71-5.61 (1H, m), 5.03 (1H, dd, J=11.2, 1.0 Hz), 4.99 (1H, dd, J=17.1, 1.5 Hz), 4.74 (2H, d, J=6.3 Hz), 3.88 (3H, s), 3.25-3.19 (4H, m), 2.64-2.59 (4H, m), 2.37 (3H, s).

ESI-MS Found: m/z[M+H] 566.

Example 16

6'-(2-Allyl-6-{[4-(4-methylpiperazin-1-yl)phenyl]amino}-3-oxo-2,3-dihydro-1H-pyrazolo[3,4-d]pyrimidin-1-yl)-5-(trifluoromethyl-2H-1,2'-bipyridin-2-one

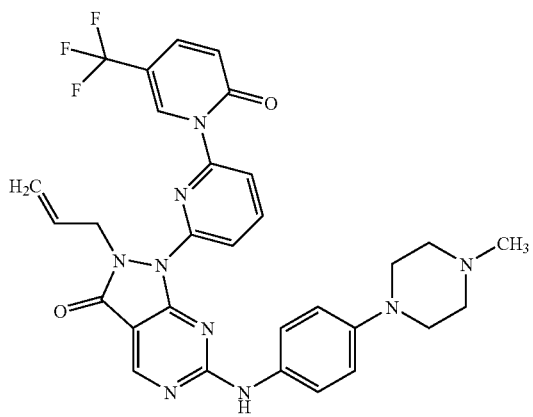

$^1$H-NMR (400 MHz, CDCl$_3$) δ: 8.84 (1H, s), 8.28-8.23 (1H, m), 8.03-7.97 (2H, m), 7.85-7.80 (1H, m), 7.54 (1H, dd, J=9.8, 2.4 Hz), 7.47-7.42 (2H, m), 6.96-6.91 (2H, m), 6.76 (1H, d, J=9.8 Hz), 5.74-5.65 (1H, m), 5.06 (1H, dd, J=10.2, 1.0 Hz), 5.01 (1H, dd, J=17.1, 1.0 Hz), 4.71 (2H, d, J=6.3 Hz), 3.24-3.20 (4H, m), 2.64-2.59 (4H, m), 2.38 (3H, s).

ESI-MS Found: m/z[M+H] 604.

Example 17

6'-(2-Allyl-6-{[4-(3,3-difluoroazetidin-1-yl)phenyl]amino}-3-oxo-2,3-dihydro-1H-pyrazolo[3,4-d]pyrimidin-1-yl)-2H-1,2'-bipyridin-2-one

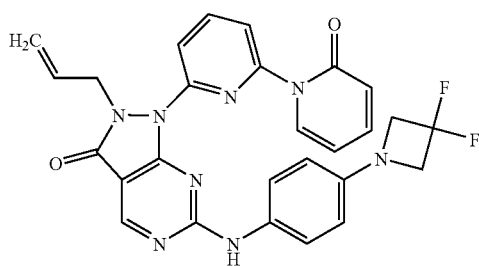

$^1$H-NMR (400 MHz, CDCl$_3$) δ: 8.83 (1H, s), 7.98-7.85 (4H, m), 7.45-7.40 (3H, m), 6.68 (1H, d, J=9.6 Hz), 6.50 (2H, d, J=9.2 Hz), 6.31 (1H, td, J=7.2, 1.2 Hz), 5.68 (1H, ddt, J=16.8, 10.4, 6.0 Hz), 5.05 (1H, d, J=10.4 Hz), 4.99 (1H, d, J=16.8 Hz), 4.72 (2H, d, J=6.0 Hz), 4.24 (4H, t, J=12.0 Hz).

ESI-MS Found: m/z[M+H] 529.

Example 18

N-(3-{([2-Allyl-3-oxo-1-(2-oxo-2H-1,2'-bipyridin-6'-yl)-2,3-dihydro-1H-pyrazolo[3,4-d]pyrimidin-6-yl]amino}phenyl)cyclopropanecarboxamide

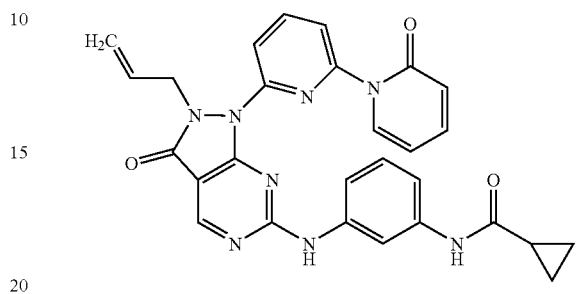

$^1$H-NMR (400 MHz, CDCl$_3$) δ: 8.86 (1H, s), 8.03-7.74 (7H, m), 7.42 (1H, m), 7.12 (1H, m), 6.67 (1H, d, J=8.8 Hz), 6.32 (1H, dd, J=6.8, 6.8 Hz), 5.68 (1H, ddt, J=17.2, 10.4, 6.0 Hz), 5.05 (1H, d, J=10.4 Hz), 4.99 (1H, d, J=17.2 Hz), 4.72 (2H, d, J=6.0 Hz), 1.57 (1H, m), 1.10 (2H, m), 0.88 (2H, m).

ESI-MS Found: m/z[M+H] 521.

Example 19

6'-[2-Allyl-6-({4-[3-(dimethylamino)propyl]phenyl}amino)-3-oxo-2,3-dihydro-1H-pyrazolo[3,4-d]pyrimidin-1-yl]-2H-1,2'-bipyridin-2-one

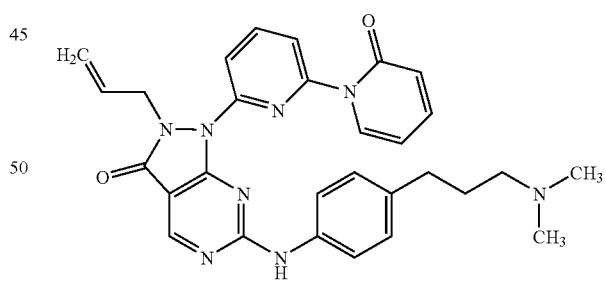

$^1$H-NMR (400 MHz, CDCl$_3$) δ: 8.86 (1H, s), 7.99 (1H, d, J=7.6 Hz), 7.93 (2H, dd, J=7.6, 2.0 Hz), 7.86 (1H, dd, J=7.2, 2.0 Hz), 7.50 (2H, d, J=8.4 Hz), 7.42 (1H, m), 7.19 (2H, d, J=8.4 Hz). 6.68 (1H, d, J=9.6 Hz), 6.31 (1H, td, J=6.0, 1.2 Hz), 5.68 (1H, ddt, J=16.0, 10.4, 6.4 Hz), 5.05 (1H, d, J=10.4 Hz), 4.99 (1H, d, J=16.0 Hz), 4.74 (2H, d, J=6.4 Hz), 2.65 (2H, t, J=7.2 Hz), 2.31 (2H, t, J=7.2 Hz), 2.24 (6H, s), 1.80 (2H, tt, J=7.2, 7.2 Hz), ESI-MS Found: m/z[M+H] 523.

Example 20

6'-[2-Allyl-6-({4-[3-(dimethylamino)azetidin-1-yl]phenyl}amino)-3-oxo-2,3-dihydro-1H-pyrazolo[3,4-d]pyrimidin-1-yl]-2H-1,2'-bipyridin-2-one

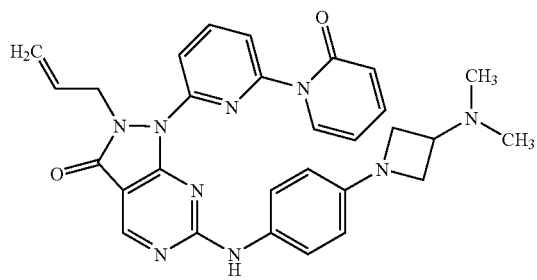

$^1$H-NMR (400 MHz, CDCl$_3$) δ: 8.81 (1H, s), 7.97-7.85 (4H, m), 7.44-7.35 (3H, m), 6.67 (1H, d, J=8.8 Hz), 6.45 (2H, d, J=9.2 Hz), 6.31 (1H, ddd, J=6.0, 6.0, 0.4 Hz), 5.67 (1H, ddt, J=17.2, 10.8, 6.4 Hz) 5.04 (1H, d, J=10.8 Hz), 4.99 (1H, d, J=17.2 Hz), 4.72 (2H, d, J=6.4 Hz), 3.99 (2H, dd, J=6.8, 6.8 Hz), 3, 67 (2H, dd, J=6.8, 6.8 Hz), 3.25 (1H, dd, J=6.8, 6.8 Hz), 2.23 (6H, s)

ESI-MS Found: m/z[M+H] 536.

Example 21

6'-[2-Allyl-6-({4-[(diethylamino)methyl]phenyl}amino)-3-oxo-2,3-dihydro-1H-pyrazolo[3,4-d]pyrimidin-1-yl]-2H-1,2'-bipyridin-2-one

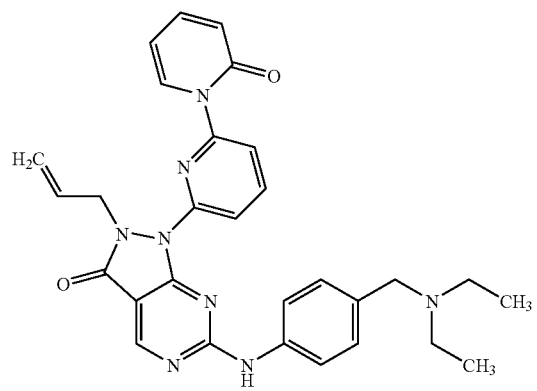

$^1$H-NMR (400 MHz, CDCl$_3$) δ: 8.87 (1H, s), 8.01 (1H, t, J=7.8 Hz), 7.93 (2H, dd, J=7.8, 4.4 Hz), 7.86 (1H, dd, J=7.1, 1.7 Hz), 7.54 (2H, d, J=8.8 Hz), 7.44-7.39 (1H, m), 7.33 (2H, d, J=8.3 Hz), 6.68 (1H, d, J=9.3 Hz), 6.32 (1H, t, J=6.8 Hz), 5.68 (1H, ddt, J=17.1, 10.2, 6.3 Hz), 5.05 (1H, dd, J=10.5, 1.2 Hz), 4.99 (1H, dd, J=17.1, 1.0 Hz), 4.74 (2H, d, J=6.3 Hz), 3.57 (2H, s), 2.54 (4H, q, J=7.2 Hz), 1.06 (6H, t, J=7.1 Hz).

ESI-MS Found: m/z[M+H] 523.

Example 22

6'-(2-Allyl-3-oxo-6-{[4-(2-oxopyrrolidin-1-yl)phenyl]amino}-2,3-dihydro-1H-pyrazolo[3,4-d]pyrimidin-1-yl)-2H-1,2'-bipyridin-2-one

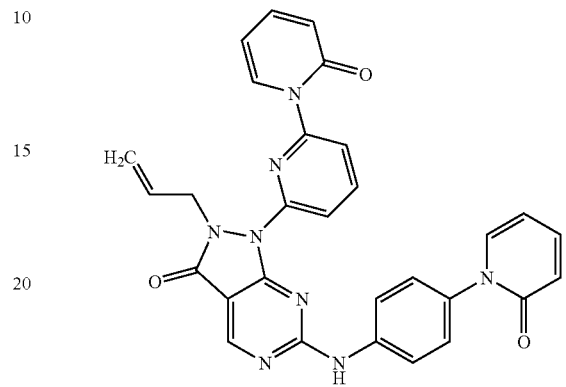

$^1$H-NMR (400 MHz, CDCl$_3$) δ: 8.87 (1H, s), 8.03 (1H, t, J=8.0 Hz), 7.91 (2H, dd, J=8.0, 3.2 Hz), 7.85 (1H, dd, J=7.1, 1.7 Hz), 7.64-7.58 (5H, m), 7.44-7.40 (1H, m), 6.68 (1H, d, J=8.8 Hz), 6.32 (1H, t, J=6.8 Hz), 5.68 (1H, ddt, J=17.1, 10.2, 6.3 Hz), 5.05 (1H, d, J=10.2 Hz), 5.00 (1H, d, J=17.1 Hz), 4.74 (2H, d, J=6.3 Hz), 3.89 (2H, t, J=6.8 Hz), 2.64 (2H, t, J=8.0 Hz), 2.20 (2H, t, J=7.5 Hz).

ESI-MS Found: m/z[M+H] 521.

Example 23

6'-(2-Allyl-3-oxo-6-{[4-(2-oxopyridin-1(2H)-yl)phenyl]amino}-2,3-dihydro-1H-pyrazolo[3,4-d]pyrimidin-1-yl)-2H-1,2'-bipyridin-2-one

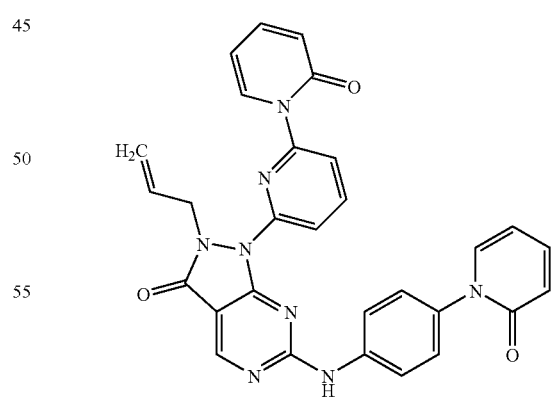

$^1$H-NMR (400 MHz, CDCl$_3$) δ: 8.89 (1H, s), 8.06 (1H, s), 8.01 (1H, t, J=8.0 Hz), 7.92-7.84 (3H, m), 7.71 (2H, d, J=8.8 Hz), 7.46-7.33 (5H, m), 6.68 (2H, t, J=10.2 Hz), 6.34-6.26 (2H, m), 5.69 (1H, ddt, J=17.1, 10.2, 6.3 Hz), 5.06 (1H, d, J=10.2 Hz), 5.00 (1H, d, J=17.1 Hz), 4.74 (2H, d, J=6.3 Hz).

ESI-MS Found: m/z[M+H] 531.

Example 24

6'-[2-Allyl-6-({4-[(2S)-2-(hydroxymethyl)pyrrolidin-1-yl]phenyl}amino)-3-oxo-2,3-dihydro-1H-pyrazolo[3,4-d]pyrimidin-1-yl]-2H-1,2'-bipyridin-2-one

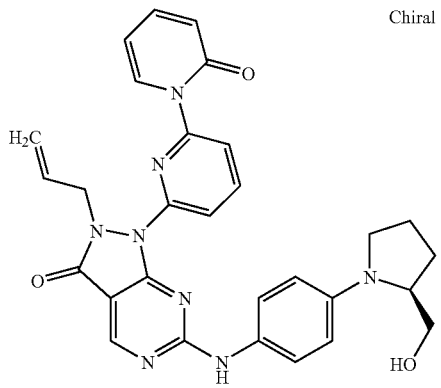

$^1$H-NMR (400 MHz, CDCl$_3$) δ: 8.81 (1H, s), 7.99-7.85 (4H, m), 7.44-7.35 (4H, m), 6.70-6.65 (3H, m), 6.33-6.29 (1H, m), 5.68 (1H, ddt, J=17.1, 10.2, 6.3 Hz), 5.05 (1H, dd, J=10.2, 1.0 Hz), 4.99 (2H, dd, J=17.1, 1.0 Hz), 4.71 (2H, d, J=5.9 Hz), 3.89-3.83 (1H, m), 3.70-3.63 (2H, m), 3.53 (1H, t, J=8.0 Hz), 3.20-3.13 (1H, m), 2.13-1.88 (4H, m).

ESI-MS Found: m/z[M+H] 537.

Example 25

6'-[2-Allyl-6-({4-[(2R)-2-(hydroxymethyl)pyrrolidin-1-yl]phenyl}amino)-3-oxo-2,3-dihydro-1H-pyrazolo[3,4-d]pyrimidin-1-yl]-2H-1,2'-bipyridin-2-one

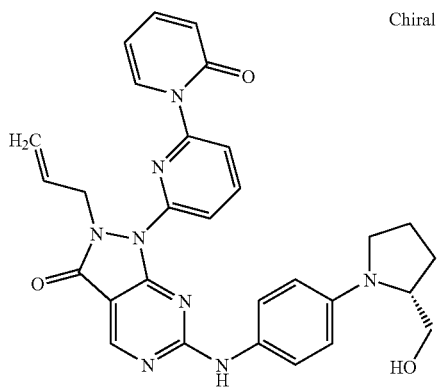

$^1$H-NMR (400 MHz, CDCl$_3$) δ: 8.81 (1H, s), 8.00-7.85 (4H, m), 7.44-7.36 (4H, m), 6.68 (3H, d, J=9.3 Hz), 6.33-6.29 (1H, m), 5.68 (1H, ddt, J=17.1, 10.2, 6.3 Hz), 5.05 (1H, dd, J=10.2, 1.0 Hz), 4.99 (2H, dd, J=17.3, 1.2 Hz), 4.71 (2H, d, J=5.4 Hz), 3.86 (1H, s), 3.71-3.63 (2H, m), 3.53 (1H, t, J=7.8 Hz), 3.19-3.13 (1H, m), 2.17-1.99 (4H, m).

ESI-MS Found: m/z[M+H] 537.

Example 26

6'-{2-Allyl-3-oxo-6-[(2,2,3,3-tetrafluoro-2,3-dihydro-1,4-benzodioxin-6-yl)amino]-2,3-dihydro-1H-pyrazolo[3,4-d]pyrimidin-1-yl}-2H-1,2'-bipyridin-2-one

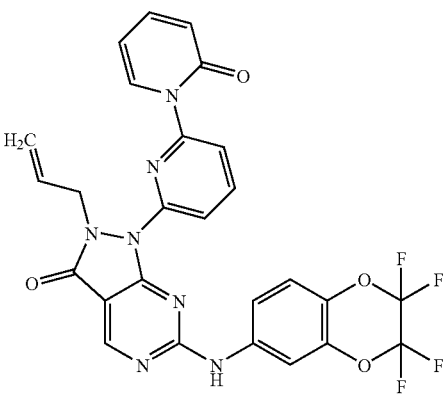

$^1$H-NMR (400 MHz, CDCl$_3$) δ: 8.89 (1H, s), 8.05 (1H, t, J=7.8 Hz), 7.96 (1H, d, J=7.8 Hz), 7.92 (1H, s), 7.89 (1H, d, J=8.3 Hz), 7.84 (1H, dd, J=6.6, 1.7 Hz), 7.70 (1H, s), 7.44-7.40 (1H, m), 7.11 (2H, s), 6.69 (1H, dd, J=9.3, 1.5 Hz), 6.34-6.30 (1H, m), 5.69 (1H, ddt, J=17.1, 10.2, 6.3 Hz), 5.06 (1H, dd, J=10.0, 1.2 Hz), 5.00 (1H, dd, J=17.1, 1.5 Hz), 4.75 (2H, d, J=6.3 Hz).

ESI-MS Found: m/z[M+H] 568.

Example 27

6'-(2-Allyl-6-{[3-(1-methylpiperizin-4-yl)phenyl]amino}-3-oxo-2,3-dihydro-1H-pyrazolo[3,4-d]pyrimidin-1-yl)-2H-1,2'-bipyridin-2-one

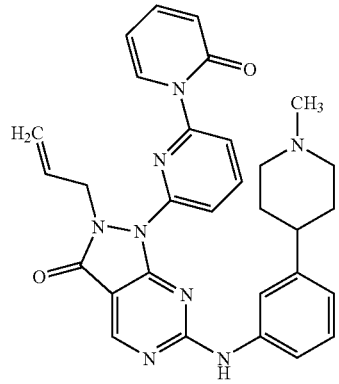

$^1$H-NMR (400 MHz, CDCl$_3$) δ: 8.87 (1H, s), 8.09 (1H, t, J=7.8 Hz), 7.94 (2H, dd, J=7.6, 5.6 Hz), 7.86 (1H, dd, J=6.8, 1.5 Hz), 7.53 (1H, brs), 7.47-7.39 (3H, m), 7.29 (1H, t, J=7.8 Hz), 7.02 (1H, d, J=7.3 Hz), 6.67 (1H, d, J=9.3 Hz), 6.33-6.29 (1H, m), 5.68 (1H, ddt, J=17.1, 10.2, 6.3 Hz), 5.05 (1H, dd, J=10.2, 1.0 Hz), 4.99 (1H, dd, J=17.1, 1.0 Hz), 4.74 (2H, d, J=6.3 Hz), 2.99 (2H, d, J=11.7 Hz), 2.53-2.44 (1H, m), 2.33 (3H, s), 2.09-2.02 (2H, m), 1.87-1.79 (4H, m).

ESI-MS Found: m/z[M+H] 535.

Example 28

6'-[2-Allyl-3-oxo-6-({4-[(2S)-2-(pyrrolidin-1-ylmethyl)pyrrolidin-1-yl]phenyl}amino)-2,3-dihydro-1H-pyrazolo[3,4-d]pyrimidin-1-yl]-2H-1,2'-bipyridin-2-one

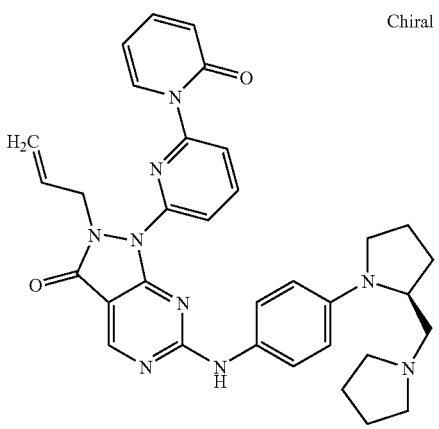

Chiral $^1$H-NMR (400 MHz, CDCl$_3$) δ: 8.81 (1H, s), 7.95 (2H, s), 7.90-7.85 (2H, m), 7.43-7.34 (3H, m), 6.67 (1H, d, J=8.8 Hz), 6.61 (2H, d, J=9.3 Hz), 6.30 (1H, t, J=6.3 Hz), 5.67 (1H, ddt, J=17.1, 10.2, 6.3 Hz), 5.04 (1H, d, J=10.2 Hz), 4.99 (1H, d, J=17.1 Hz), 4.73 (2H, d, J=6.3 Hz), 3.85 (1H, s), 3.46-3.42 (1H, m), 3.18-3.11 (1H, m), 2.70-2.64 (2H, m), 2.60-2.55 (3H, m), 2.47 (1H, t, J=11.2 Hz), 2.16-1.99 (4H, m), 1.83-1.79 (4H, m).
ESI-MS Found: m/z[M+H] 590.

Example 29

6'-(2-Allyl-6-{[3-(hydroxymethyl)-4-methoxyphenyl]amino}-3-oxo-2,3-dihydro-1H-pyrazolo[3,4-d]pyrimidin-1-yl)-2H-1,2'-bipyridin-2-one

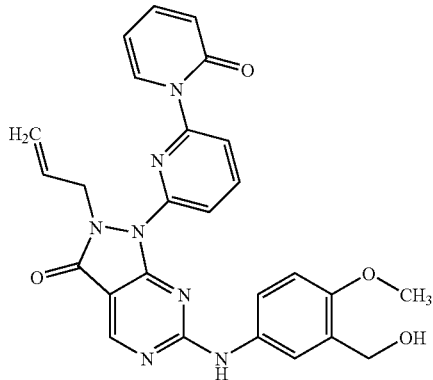

$^1$H-NMR (400 MHz, CDCl$_3$) δ: 8.84 (1H, s), 8.06 (1H, t, J=7.6 Hz), 7.95 (1H, d, J=7.8 Hz), 7.89 (1H, d, J=7.8 Hz), 7.83 (1H, d, J=7.3 Hz), 7.68 (1H, bra), 7.50 (1H, brs), 7.44-7.39 (1H, m), 6.86 (1H, d, J=8.8 Hz), 6.67 (1H, d, J=8.8 Hz), 6.31 (1H, t, J=6.8 Hz), 5.68 (1H, ddt, J=17.1, 10.2, 6.3 Hz), 5.04 (1H, d, J=10.2 Hz), 4.99 (1H, d, J=17.1 Hz), 4.74 (2H, d, J=5.9 Hz), 4.70 (2H, d, J=6.3 Hz), 3.89 (3H, s), 2.35 (1H, t, J=5.9 Hz).
ESI-MS Found: m/z[M+H] 498.

Example 30

6'-{2-Allyl-6-[(2-methyl-1,2,3,4-tetrahydroisoquinolin-7-yl)amino]-3-oxo-2,3-dihydro-1H-pyrazolo[3,4-d]pyrimidin-1-yl}-2H-1,2'-bipyridin-2-one

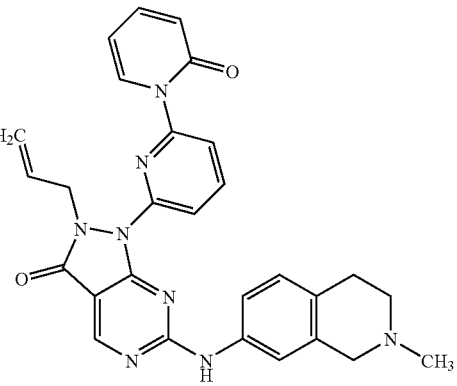

$^1$H-NMR (400 MHz, CDCl$_3$) δ: 8.86 (1H, s), 8.00 (1H, t, J=7.8 Hz), 7.96-7.92 (2H, m), 7.86 (1H, dd, J=7.6, 1.7 Hz), 7.48 (1H, brs), 7.44-7.39 (1H, m), 7.34 (1H, s), 7.30 (1H, dd, J=8.0, 2.2 Hz), 7.10 (1H, d, J=8.3 Hz), 6.68 (1H, d, J=9.3 Hz), 6.33-6.29 (1H, m), 5.68 (1H, ddt, J=17.1, 10.2, 6.3 Hz), 5.05 (1H, d, J=10.2 Hz), 4.99 (1H, dd, J=17.1, 1.5 Hz), 4.74 (2H, d, J=6.3 Hz), 3.59 (2H, s), 2.92 (2H, t, J=5.9 Hz), 2.72 (2H, t, J=5.9 Hz), 2.49 (3H, s).
ESI-MS Found: m/z[M+H] 507.

Example 31

6'-[2-Allyl-6-({4-[methyl(pyridin-2-ylmethyl)amino]phenyl}amino)-3-oxo-2,3-dihydro-1H-pyrazolo[3,4-d]pyrimidin-1-yl]-2H-1,2'-bipyridin-2-one

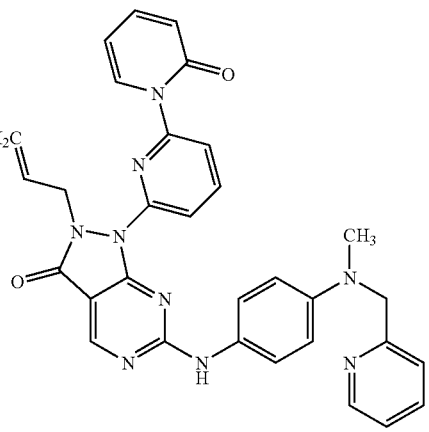

$^1$H-NMR (400 MHz, CDCl$_3$) δ: 8.81 (1H, s), 8.61 (1H, d, J=4.9 Hz), 7.91-7.84 (3H, m), 7.62 (1H, td, J=7.7, 1.8 Hz), 7.43-7.35 (4H, m), 7.19 (2H, t, J=6.6 Hz), 6.71 (2H, d, J=8.8 Hz), 6.66 (1H, d, J=8.8 Hz), 6.32-6.28 (1H, m), 5.67 (1H, ddt, J=17.1, 10.2, 5.9 Hz), 5.03 (1H, d, J=10.2 Hz), 4.98 (1H, dd, J=17.1, 1.0 Hz), 4.72 (2H, d, J=5.9 Hz), 4.67 (2H, s), 3.16 (3H, s).
ESI-MS Found: m/z[M+H] 558.

Example 32

6'-(2-Allyl-6-{[4-(2-methyl-2,7-diazaspiro[3.5]non-7-yl)phenyl]amino}-3-oxo-2,3-dihydro-1H-pyrazolo[3,4-d]pyrimidin-1-yl)-2H-1,2'-bipyridin-2-one

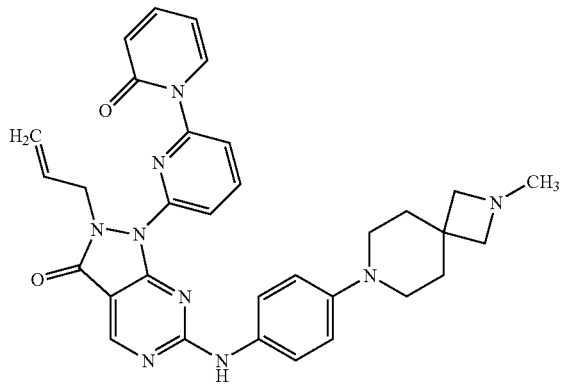

¹H-NMR (400 MHz, CDCl₃) δ: 8.82 (1H, s), 7.97 (1H, d, J=7.3 Hz), 7.93-7.85 (4H, m), 7.45-7.39 (3H, m), 6.92 (2H, d, J=9.3 Hz), 6.67 (1H, d, J=9.3 Hz), 6.33-6.29 (1H, m), 5.68 (1H, ddt, J=17.2, 10.2, 6.3 Hz), 5.04 (1H, d, J=10.2 Hz), 4.99 (1H, dd, J=16.8, 1.2 Hz), 4.73 (2H, d, J=6.3 Hz), 3.10 (4H, t, J=5.6 Hz), 3.08 (4H, s), 2.37 (3H, s), 1.90 (4H, t, J=5.6 Hz).
ESI-MS Found: m/z[M+H] 576.

Example 33

6'-(2-Allyl-6-{[4-(5-methylhexahydropyrrolo[3,4-b]pyrrol-1(2H)-yl)phenyl]amino}-3-oxo-2,3-dihydro-1H-pyrazolo[3,4-d]pyrimidin-1-yl)-2H-1,2'-bipyridin-2-one

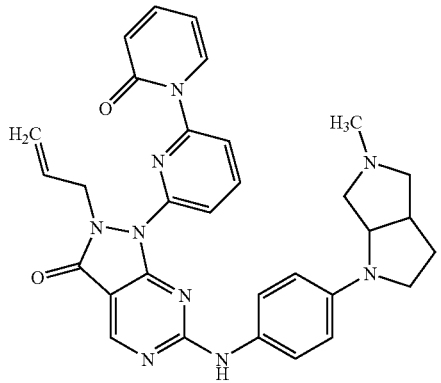

¹H-NMR (400 MHz, CDCl₃) δ: 8.81 (1H, s), 7.94-7.85 (4H, m), 7.43-7.35 (3H, m), 6.67 (1H, d, J=9.3 Hz), 6.57 (2H, d, J=9.3 Hz), 6.33-6.29 (1H, m), 5.74-5.62 (1H, m), 5.04 (1H, d, J=10.2 Hz), 4.99 (1H, dd, J=17.1, 1.5 Hz), 4.73 (2H, d, J=6.3 Hz), 3.57-3.51 (1H, m), 3.27-3.20 (1H, m), 2.96 (1H, brs), 2.73 (1H, d, J=11.7 Hz), 2.60-2.48 (4H, m), 2.33 (3H, s), 2.24-2.14 (1H, m), 1.99-1.90 (1H, m).
ESI-MS Found: m/z[M+H] 562.

Example 34

6'-(2-Allyl-6-{[4-(1-methylhexahydropyrrolo[3,4-b]pyrrol-5(1H)-yl)phenyl]amino}-3-oxo-2,3-dihydro-1H-pyrazolo[3,4-d]pyrimidin-1-yl)-2H-1,2'-bipyridin-2-one

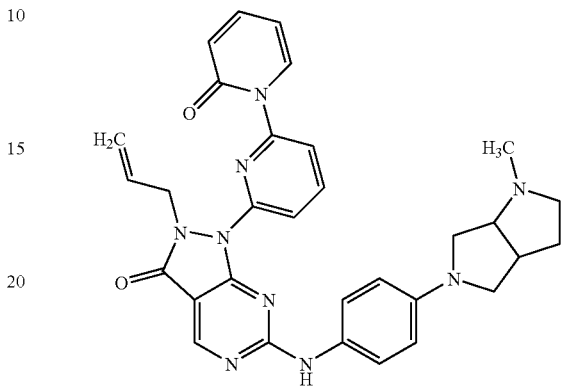

¹H-NMR (400 MHz, CDCl₃) δ: 8.80 (1H, s), 7.98-7.85 (4H, m), 7.68 (1H, brs), 7.43-7.39 (1H, m), 7.36 (2H, d, J=8.8 Hz), 6.67 (1H, d, J=9.3 Hz), 6.63 (2H, d, J=8.8 Hz), 6.31 (1H, t, J=6.1 Hz), 5.72-5.62 (1H, m), 5.04 (1H, d, J=10.2 Hz), 4.99 (1H, dd, J=16.8, 1.2 Hz), 4.73 (2H, d, J=6.3 Hz), 3.51 (1H, d, J=10.2 Hz), 3.33-3.31 (2H, m), 3.15 (dd, J=10.2, 5.4 Hz), 3.02-2.91 (2H, m), 2.44 (3H, s), 2.42-2.38 (1H, m), 2.22-2.14 (1H, m), 1.83-1.74 (1H, m).
ESI-MS Found: m/z[M+H] 562.

Example 35

6'-[2-Allyl-6-({4-[3-(tert-butylamino)pyrrolidin-1-yl]phenyl}amino)-3-oxo-2,3-dihydro-1H-pyrazolo[3,4-d]pyrimidin-1-yl]-2H-1,2'-bipyridin-2-one

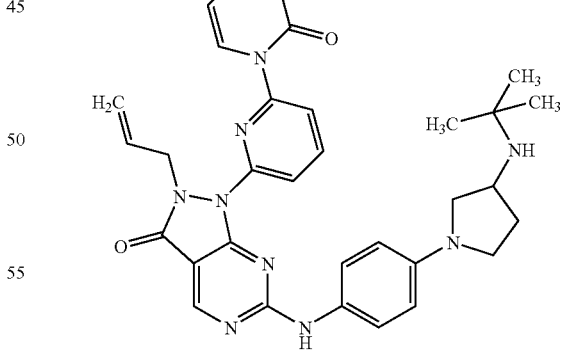

¹H-NMR (400 MHz, CDCl₃) δ: 8.81 (1H, s), 7.97-7.85 (4H, m), 7.44-7.33 (4H, m), 6.67 (1H, d, J=8.8 Hz), 6.52 (2H, d, J=8.8 Hz), 6.30 (1H, t, J=6.8 Hz), 5.67 (1H, ddt, J=17.2, 10.2, 6.3 Hz), 5.04 (1H, d, J=10.2 Hz), 4.99 (1H, d, J=17.1 Hz), 4.73 (2H, d, J=6.3 Hz), 3.61-3.56 (2H, m), 3.41 (1H, t, J=7.1 Hz), 3.35-3.28 (1H, m), 2.95 (1H, s), 2.30 (1H, s), 1.85-1.74 (1H, m), 1.17 (9H, s).
ESI-MS Found: m/z[M+H] 578.

Example 36

6'-{2-Isopropyl-6-[(2-methyl-1,2,3,4-tetrahydroisoquinolin-7-yl)amino]-3-oxo-2,3-dihydro-1H-pyrazolo[3,4-d]pyrimidin-1-yl}-2H-1,2'-bipyridin-2-one

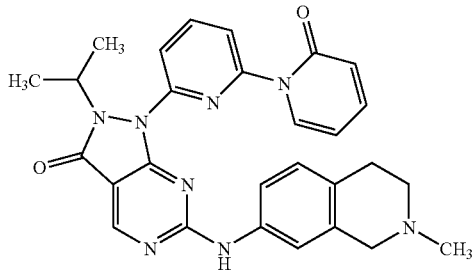

$^1$H-NMR (400 MHz, DMSO-$d_6$) δ: 10.24 (1H, brs), 8.81 (1H, s), 8.22 (1H, t, J=7.8 Hz), 7.95 (1H, d, J=7.8 Hz), 7.87 (1H, dd, J=7.6, 1.7 Hz), 7.81 (1H, d, J=7.8 Hz), 7.53 (1H, ddd, J=9.0, 6.6, 2.2 Hz), 7.46 (1H, brs), 7.41 (1H, dd, J=8.3, 2.0 Hz), 7.01 (1H, d, J=8.3 Hz), 6.52 (1H, dd, J=9.3, 1.0 Hz), 6.37 (1H, td, J=6.7, 1.1 Hz), 4.25-4.17 (1H, m), 3.44 (2H, s), 2.75 (2H, t, J=5.6 Hz), 2.57 (2H, t, J=5.9 Hz), 2.35 (3H, s), 1.33 (6H, d, J=6.8 Hz).

ESI-MS Found: m/z[M+H] 509.

Example 37

6'-{2-Methyl-6-[(2-methyl-1,2,3,4-tetrahydroisoquinolin-6-yl)amino]-3-oxo-2,3-dihydro-1H-pyrazolo[3,4-d]pyrimidin-1-yl}-2H-1,2'-bipyridin-2-one

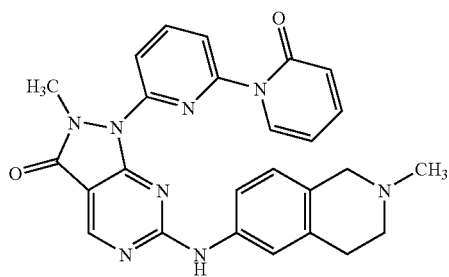

$^1$H-NMR (400 MHz, DMSO-$d_6$) δ: 10.26 (1H, s), 8.86 (1H, s), 8.25 (1H, t, J=8.0 Hz), 8.01 (1H, d, J=8.3 Hz), 7.90 (1H, dd, J=6.8, 1.5 Hz), 7.73 (1H, d, J=7.8 Hz), 7.62 (1H, brs), 7.54 (1H, ddd, J=9.1, 6.7, 2.3 Hz), 7.40 (1H, dd, J=8.5, 2.2 Hz), 6.98 (1H, d, J=8.8 Hz), 6.53 (1H, d, J=9.3 Hz), 6.37 (1H, td, J=6.8, 1.0 Hz), 3.44 (2H, s), 3.38 (3H, s), 2.81 (2H, t, J=5.4 Hz), 2.59 (2H, t, J=5.9 Hz), 2.34 (3H, s).

ESI-MS Found: m/z[M+H] 481.

Example 38

6'-{2-Methyl-6-[(2'-methyl-2',3'-dihydro-1'H-spiro[cyclopropane-1,4'-isoquinolin]-7'-yl)amino]-3-oxo-2,3-dihydro-1H-pyrazolo[3,4-d]pyrimidin-1-yl}-2H-1,2'-bipyridin-2-one

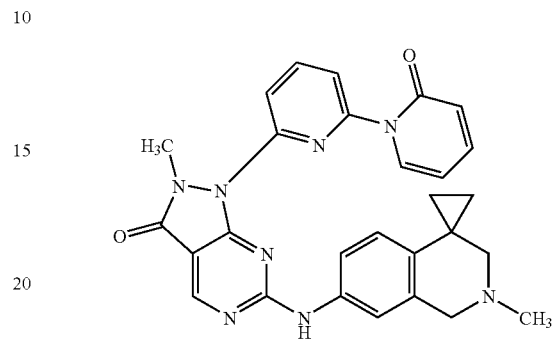

$^1$H-NMR (400 MHz, DMSO-$d_6$) δ: 10.25 (1H, brs), 8.86 (1H, s), 8.24 (1H, t, J=8.0 Hz), 8.00 (1H, d, J=8.3 Hz), 7.90 (1H, dd, J=7.3, 1.5 Hz), 7.75 (1H, d, J=7.8 Hz), 7.54 (1H, ddd, J=9.0, 6.6, 2.2 Hz), 7.50-7.41 (2H, m), 6.65 (1H, d, J=8.8 Hz), 6.53 (1H, d, J=9.3 Hz), 6.38 (1H, td, J=6.7, 1.1 Hz), 3.58 (2H, s), 3.38 (3H, s), 2.34 (3H, s), 0.90-0.84 (4H, m).

ESI-MS Found: m/z[M+H] 507.

Example 39

6'-{2-Isopropyl-6-[(2'-methyl-2',3'-dihydro-1'H-spiro[cyclopropane-1,4'-isoquinolin]-7'-yl)amino)-3-oxo-2,3-dihydro-1H-pyrazolo[3,4-d]pyrimidin-1-yl]-2H-1,2'-bipyridin-2-one

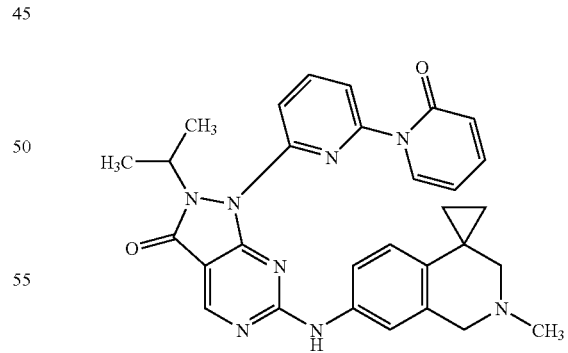

$^1$H-NMR (400 MHz, CDCl$_3$) δ: 8.80 (1H, s), 8.04-7.98 (2H, m), 7.94 (1H, dd, J=7.1, 1.7 Hz), 7.84 (1H, dd, J=7.1, 1.7 Hz), 7.61 (1H, brs), 7.40 (1H, ddd, J=9.1, 6.7, 2.3 Hz), 7.29 (1H, d, J=2.4 Hz), 6.65 (2H, dd, J=18.8, 8.5 Hz), 6.29 (1H, td, J=6.8, 1.0 Hz), 4.28-4.21 (1H, m), 3.69 (2H, s), 2.54 (2H, s), 2.47 (3H, s), 1.47 (6H, d, J=6.8 Hz), 1.03-0.90 (4H, m).

ESI-MS Found: m/z[M+H] 535.

Example 40

6'-{2-Isopropyl-3-oxo-6-[(2,4,4-trimethyl-1,2,3,4-tetrahydroisoquinolin-7-yl)amino]-2,3-dihydro-1H-pyrazolo[3,4-d]pyrimidin-1-yl}-2H-1,2'-bipyridin-2-one

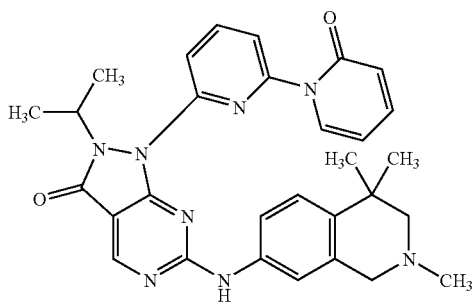

$^1$H-NMR (400 MHz, CDCl$_3$) δ: 8.80 (1H, s), 8.05-7.98 (2H, m), 7.95 (1H, dd, J=7.3, 2.0 Hz), 7.86 (1H, dd, J=6.8, 2.0 Hz), 7.40 (1H, ddd, J=9.0, 6.6, 2.2 Hz), 7.33 (1H, dd, J=8.8, 2.4 Hz), 7.30-7.24 (2H, m), 6.67 (1H, d, J=9.3 Hz), 6.29 (1H, td, J=6.8, 0.7 Hz), 4.31-4.20 (1H, m), 3.52 (2H, s), 2.43 (3H, s), 2.40 (2H, s), 1.47 (6H, d, J=6.8 Hz), 1.31 (6H, s).

ESI-MS Found: m/z[M+H] 537.

Example 41

6'-{2-Ethyl-6-[(2'-methyl-2',3'-dihydro-1'H-spiro[cyclopropane-1,4'-isoquinolin]-7'-yl)amino]-3-oxo-2,3-dihydro-1H-pyrazolo[3,4-d]pyrimidin-1-yl}-2H-1,2'-bipyridin-2-one

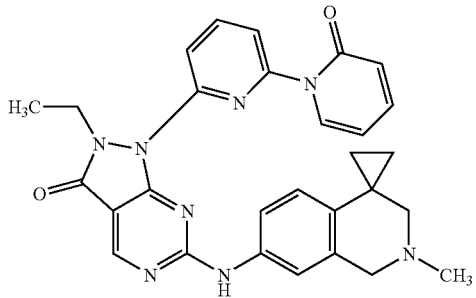

$^1$H-NMR (400 MHz, DMSO-d$_6$) δ: 10.25 (1H, brs), 8.85 (1H, s), 8.25 (1H, t, J=7.8 Hz), 8.02 (1H, d, J=8.3 Hz), 7.88 (1H, dd, J=7.1, 1.7 Hz), 7.76 (1H, d, J=7.8 Hz), 7.54 (1H, ddd, J=9.3, 6.6, 2.2 Hz), 7.50-7.40 (2H, m), 6.64 (1H, d, J=8.8 Hz), 6.52 (1H, d, J=8.8 Hz), 6.37 (1H, td, J=6.8, 1.5 Hz), 3.96 (2H, q, J=7.0 Hz), 3.57 (2H, s), 2.44 (2H, s), 2.33 (3H, s), 0.99 (3H, t, J=6.8 Hz), 0.92-0.80 (4H, m).

ESI-MS Found: m/z[M+H] 521.

Example 42

6'-{6-[(2-Methyl-1,2,3,4-tetrahydroisoquinolin-7-yl)amino]-3-oxo-2-(2-propynyl)-2,3-dihydro-1H-pyrazolo[3,4-d]pyrimidin-1-yl}-2H-1,2'-bipyridin-2-one

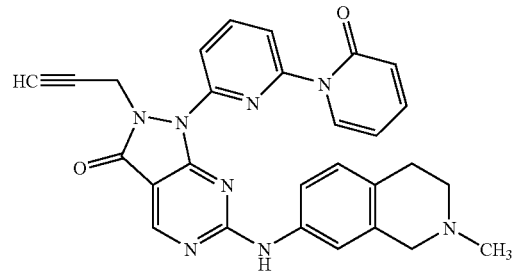

$^1$H-NMR (400 MHz, DMSO-d$_6$) δ: 10.44 (1H, brs), 8.91 (1H, s), 8.24 (1H, t, J=8.0 Hz), 7.92-7.85 (2H, m), 7.73 (1H, d, J=7.8 Hz), 7.68-7.64 (1H, m), 7.56-7.50 (1H, m), 7.44 (1H, dd, J=8.3, 2.4 Hz), 7.08 (1H, d, J=8.3 Hz), 6.52 (1H, d, J=8.8 Hz), 6.36 (1H, td, J=6.8, 1.0 Hz), 4.76 (2H, d, J=2.4 Hz), 3.55 (2H, s), 3.20 (1H, t, J=2.4 Hz), 2.80 (2H, t, J=5.6 Hz), 2.65 (2H, t, J=5.6 Hz), 2.40 (3H, s).

ESI-MS Found: m/z[M+H] 505.

INDUSTRIAL APPLICABILITY

The compounds of the invention have an excellent Wee1-kinase-inhibitory effect, and are therefore useful in the field of medicine, especially in the field of various cancer treatments.

The invention claimed is:

1. A compound of general formula (I-0), or its pharmaceutically-acceptable salt:

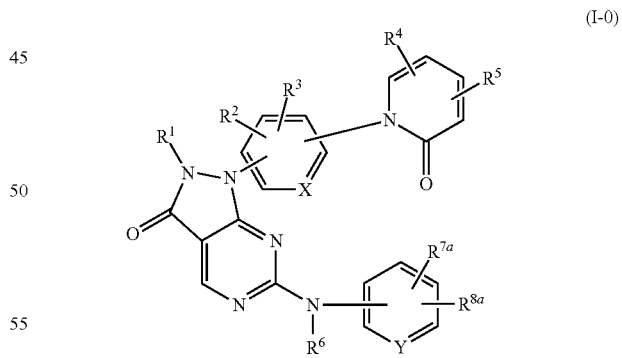

(I-0)

wherein R$^1$ means a C1-C6 alkyl group, a C2-C6 alkenyl group, a C2-C6 alkynyl group or a C3-C6 cycloalkyl group, any of which may be substituted with a halogen atom;

R$^2$, R$^3$, R$^4$ and R$^5$ each independently mean a hydrogen atom, a halogen atom, a C1-C6 alkyl group, a halo-C1-C6 alkyl group, a C1-C6 alkoxy group or a halo-C1-C6 alkoxy group;

R$^6$ means a hydrogen atom or a C1-C6 alkyl group;

$R^{7a}$ means a hydrogen atom, a halogen atom, a C1-C6 alkyl group, a halo-C1-C6 alkyl group, a C1-C6 alkoxy group, a hydroxy-C1-C6 alkyl group or a group of $-Q^2-N(R^{1c})R^{1d}$, or means a nitrogen-containing heterocyclic group optionally substituted with a substituent selected from the group consisting of a halogen atom, a C1-C6 alkyl group, a hydroxy-C1-C6 alkyl group, an oxo group and a group of $-Q^1-N(R^{1a})R^{1b}$;

$R^{8a}$ means a hydrogen atom, a halogen atom, a C1-C6 alkyl group, a halo-C1-C6 alkyl group, a C1-C6 alkoxy group or a hydroxy-C1-C6 alkyl group;

or when $R^{7a}$ and $R^{8a}$ exist on the ring atoms, adjacent to each other, of the group of the following formula (a):

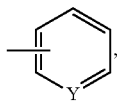
(a)

$R^{7a}$ and $R^{8a}$ may form, as taken together, a C2-C6 alkylene group, in which one or two methylene groups constituting the C2-C6 alkylene group may be each independently replaced by an oxygen atom or a group of $-N(R^{1e})-$, and the C2-C6 alkylene group may be substituted with a substituent selected from the group consisting of a halogen atom, a C1-C6 alkyl group and a halo-C1-C6 alkyl group; or $R^{7a}$ and $R^{8a}$ and the ring atoms to which they bond may be, as taken together, a spiro ring or a bicyclo ring to be formed of a 5-membered to 7-membered aliphatic ring and any other 3-membered to 7-membered aliphatic ring, in which one or two or more methylene groups constituting the spiro ring or the bicyclo ring may be each independently replaced by an oxygen atom, a sulfur atom, a sulfinyl group, a sulfonyl group, a carbonyl group or a group of $-N(R^{1f})-$, and the spiro ring or the bicyclo ring may be each independently substituted with a substituent selected from the group consisting of a halogen atom, a hydroxyl group, a C1-C6 alkyl group, a hydroxy-C1-C6 alkyl group or a group of $-Q^3-N(R^{1g})R^{1h}$;

$R^{1a}$ and $R^{1b}$ each independently mean a hydrogen atom, a C1-C6 alkyl group or a halo-C1-C6 alkyl group, or, as taken together, they may form a C2-C6 alkylene group, in which the C2-C6 alkylene group may be substituted with a substituent selected from the group consisting of a halogen atom, a C1-C6 alkyl group and a halo-C1-C6 alkyl group;

$R^{1c}$, $R^{1d}$ and $R^{1e}$ each independently mean a hydrogen atom, or mean a C1-C6 alkyl group optionally substituted with a substituent selected from the group consisting of a halogen atom, a hydroxyl group, an oxo group, a C3-C6 cycloalkyl group and a nitrogen-containing heterocyclic group;

$R^{1f}$ means a hydrogen atom, or means a C1-C6 alkyl group, a C3-C6 cycloalkyl group or a C2-C7 alkanoyl group, which may have a substituent selected from the group consisting of a halogen atom, a hydroxyl group, a cyano group, a C1-C6 alkoxy group, a C3-C6 cycloalkyl group and a C2-C7 alkanoyl group, or means a group of $-Q^4-Cy$ of $-Q^5-N(R^{1i})R^{1j}$;

Cy means an aryl group or a heterocyclic group, any of which may be substituted with a halogen atom or a C1-C6 alkyl group;

$R^{1g}$ and $R^{1h}$ each independently mean a hydrogen atom, or mean a C1-C6 alkyl group, a C2-C7 alkanoyl group or a C1-C6 alkylsulfonyl group, which may have a substituent selected from the group consisting of a halogen atom, a hydroxyl group, a cyano group, a C1-C6 alkoxy group, a C3-C6 cycloalkyl group, a C2-C7 alkanoyl group and a C1-C6 alkylsulfonyl group, or mean a group of $-Q^6-N(R^{1k})R^{1l}$;

$R^{1i}$, $R^{1j}$, $R^{1k}$ and $R^{1l}$ each independently mean a hydrogen atom, or mean a C1-C6 alkyl group, a C2-C7 alkanoyl group or a C1-C6 alkylsulfonyl group, which may have a substituent selected from the group consisting of a halogen atom, a hydroxyl group, a cyano group, a C1-C6 alkoxy group, a C3-C6 cycloalkyl group, a C2-C7 alkanoyl group and a C1-C6 alkylsulfonyl group;

$Q^1$ and $Q^2$ each independently mean a single bond or a C1-C3 alkylene group;

$Q^3$, $Q^4$, $Q^5$ and $Q^6$ each independently means a single bond or a C1-C6 alkylene group, in which one or two or more methylene groups constituting the C1-C6 alkylene group may be each independently replaced by a sulfinyl group, a sulfonyl group or a carbonyl group;

X means a methine group or a nitrogen atom; and

Y means a methine group.

2. The compound or its pharmaceutically-acceptable salt as claimed in claim 1, wherein the compound is represented by general formula (I):

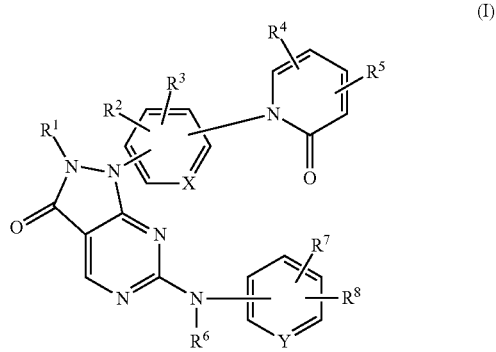
(I)

wherein $R^1$ means a C1-C6 alkyl group, a C2-C6 alkenyl group, a C2-C6 alkynyl group or a C3-C6 cycloalkyl group, any of which may be substituted with a halogen atom;

$R^2$, $R^3$, $R^4$ and $R^5$ each independently mean a hydrogen atom, a halogen atom, a C1-C6 alkyl group, a halo-C1-C6 alkyl group, a C1-C6 alkoxy group or a halo-C1-C6 alkoxy group;

$R^6$ means a hydrogen atom or a C1-C6 alkyl group;

$R^7$ means a hydrogen atom, a halogen atom, a C1-C6 alkyl group, a halo-C1-C6 alkyl group, a C1-C6 alkoxy group, a hydroxy-C1-C6 alkyl group or a group of $-Q^2-N(R^{1c})R^{1d}$, or means a nitrogen-containing heterocyclic group optionally substituted with a substituent selected from the group consisting of a halogen atom, a C1-C6 alkyl group, a hydroxy-C1-C6 alkyl group, an oxo group and a group of $-Q^1-N(R^{1a})R^{1b}$;

$R^8$ means a hydrogen atom, a halogen atom, a C1-C6 alkyl group, a halo-C1-C6 alkyl group, a C1-C6 alkoxy group or a hydroxy-C1-C6 alkyl group;

or when R⁷ and R⁸ exist on the ring atoms, adjacent to each other, of the group of the following formula (a):

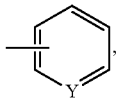
(a)

R⁷ and R⁸ may form, as taken together, a C2-C6 alkylene group, in which one or two methylene groups constituting the C2-C6 alkylene group may be each independently replaced by an oxygen atom or a group of —N(R¹ᵉ)—, and the C2-C6 alkylene group may be substituted with a substituent selected from the group consisting of a halogen atom, a C1-C6 alkyl group and a halo-C1-C6 alkyl group;

R¹ᵃ and R¹ᵇ each independently mean a hydrogen atom, a C1-C6 alkyl group or a halo-C1-C6 alkyl group, or, as taken together, they may form a C2-C6 alkylene group, in which the C2-C6 alkylene group may be substituted with a substituent selected from the group consisting of a halogen atom, a C1-C6 alkyl group and a halo-C1-C6 alkyl group;

R¹ᶜ, R¹ᵈ and R¹ᵉ each independently mean a hydrogen atom, or mean a C1-C6 alkyl group optionally substituted with a substituent selected from the group consisting of a halogen atom, a hydroxyl group, an oxo group, a C3-C6 cycloalkyl group and a nitrogen-containing heterocyclic group;

Q¹ and Q² each independently mean a single bond or a C1-C3 alkylene group; and X means a methine group or a nitrogen atom; and Y means a methine group.

3. The compound or its pharmaceutically-acceptable salt as claimed in claim 1, wherein R⁷ᵃ and R⁸ᵃ exist on the ring atoms, adjacent to each other, of the group of the following formula (a):

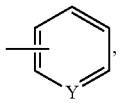
(a)

and R⁷ᵃ and R⁸ᵃ and the ring atoms to which they bond form, as taken together, a spiro ring or a bicyclo ring formed of a 5-membered to 7-membered aliphatic ring and any other 3-membered to 7-membered aliphatic ring, in which one or two or more methylene groups constituting the spiro ring or the bicyclo ring may be each independently replaced by an oxygen atom, a sulfur atom, a sulfinyl group, a sulfonyl group, a carbonyl group or a group of —N(R¹ᶠ)—, and the spiro ring or the bicyclo ring may be each independently substituted with a substituent selected from the group consisting of a halogen atom, a hydroxyl group, a C1-C6 alkyl group, a hydroxy-C1-C6 alkyl group or a group of -Q³-N(R¹ᵍ)R¹ʰ.

4. The compound or its pharmaceutically-acceptable salt as claimed in claim 2, wherein R¹ is a C2-C6 alkenyl group.

5. The compound or its pharmaceutically-acceptable salt as claimed in claim 2, wherein R⁷ is a group of -Q²-N(R¹ᶜ)R¹ᵈ, or is a nitrogen-containing heterocyclic group selected from the group consisting of an azetidinyl group, a pyrrolidinyl group, a piperidinyl group, a piperazinyl group, a dihydropyridyl group, a 2,7-diazaspiro[3.5]nonyl group, a 2,7-diazabicyclo[3.3.0]octyl group and a 3,6-diazabicyclo[3.3.0]octyl group, any of which may be substituted with a substituent selected from the group consisting of a halogen atom, a C1-C6 alkyl group, a hydroxy-C1-C6 alkyl group, an oxo group and a group of -Q¹-N(R¹ᵃ)R¹ᵇ, in which R¹ᵃ and R¹ᵇ are each independently a hydrogen atom or a C1-C6 alkyl group, or form, as taken together, a C2-C6 alkylene group, R¹ᶜ and R¹ᵈ are each independently a hydrogen atom, or a C1-C6 alkyl group optionally substituted with a substituent selected from the group consisting of a hydroxyl group, an oxo group, a C3-C6 cycloalkyl group and a pyridyl group.

6. The compound or its pharmaceutically-acceptable salt as claimed in claim 2, wherein the group of a formula (a-1):

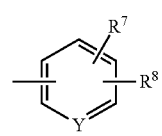
(a-1)

is a group of a formula (a-2):

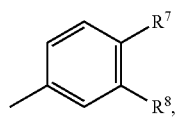
(a-2)

in which R⁷ and R⁸ form, as taken together, a C2-C6 alkylene group, one or two methylene groups constituting the C2-C6 alkylene group each are replaced by a group of —N(R¹ᵉ)—, and R¹ᵉ is a C1-C6 alkyl group.

7. The compound or its pharmaceutically-acceptable salt as claimed in claim 3, wherein the group of a formula (a-0):

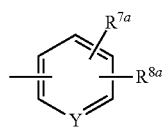
(a-0)

is a group selected from formula (a-14):

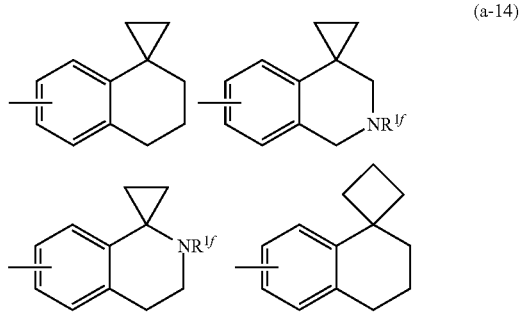
(a-14)

-continued

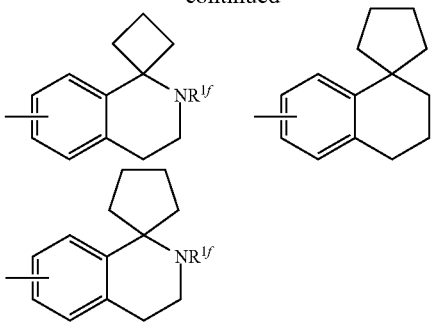

wherein one or two or more methylene groups constituting the aliphatic ring of the group may be each independently substituted with a halogen atom, a hydroxyl group, a C1-C6 alkyl group, a hydroxy-C1-C6 alkyl group or a group of $-Q^3-N(R^{1g})R^{1h}$.

8. The compound or its pharmaceutically-acceptable salt as claimed in claim 2, wherein the compound is represented by general formula (I-1):

(I-1)

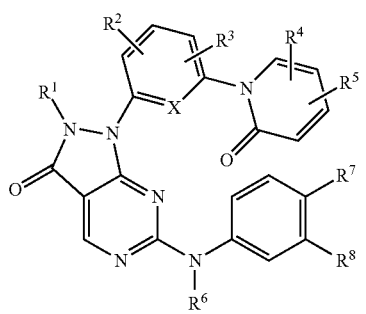

wherein $R^1$ means a C1-C6 alkyl group, a C2-C6 alkenyl group, a C2-C6 alkynyl group or a C3-C6 cycloalkyl group, any of which may be substituted with a halogen atom;
$R^2$, $R^3$, $R^4$ and $R^5$ each independently mean a hydrogen atom, a halogen atom, a C1-C6 alkyl group, a halo-C1-C6 alkyl group, a C1-C6 alkoxy group or a halo-C1-C6 alkoxy group;
$R^6$ means a hydrogen atom or a C1-C6 alkyl group;
$R^7$ means a hydrogen atom, a halogen atom, a C1-C6 alkyl group, a halo-C1-C6 alkyl group, a C1-C6 alkoxy group, a hydroxy-C1-C6 alkyl group or a group of $-Q^2-N(R^{1c})R^{1d}$, or means a nitrogen-containing heterocyclic group optionally substituted with a substituent selected from the group consisting of a halogen atom, a C1-C6 alkyl group, a hydroxy-C1-C6 alkyl group, an oxo group and a group of $-Q^1-N(R^{1a})R^{1b}$;
$R^8$ means a hydrogen atom, a halogen atom, a C1-C6 alkyl group, a halo-C1-C6 alkyl group, a C1-C6 alkoxy group or a hydroxy-C1-C6 alkyl group;
or $R^7$ and $R^8$ form, as taken together, a C2-C6 alkylene group, in which one or two methylene groups constituting the C2-C6 alkylene group each independently are replaced by an oxygen atom or a group of $-N(R^{1e})-$, and the C2-C6 alkylene group may be substituted with a substituent selected from the group consisting of a halogen atom, a C1-C6 alkyl group and a halo-C1-C6 alkyl group;

$R^{1a}$ and $R^{1b}$ each independently mean a hydrogen atom, a C1-C6 alkyl group or a halo-C1-C6 alkyl group, or, as taken together, they may form a C2-C6 alkylene group, in which the C2-C6 alkylene group may be substituted with a substituent selected from the group consisting of a halogen atom, a C1-C6 alkyl group and a halo-C1-C6 alkyl group;
$R^{1c}$, $R^{1d}$ and $R^{1e}$ each independently mean a hydrogen atom, or mean a C1-C6 alkyl group optionally substituted with a substituent selected from the group consisting of a halogen atom, a hydroxyl group, an oxo group, a C3-C6 cycloalkyl group and a nitrogen-containing heterocyclic group;
$Q^1$ and $Q^2$ each independently mean a single bond or a C1-C3 alkylene group; and
X means a methine group or a nitrogen atom.

9. The compound or its pharmaceutically-acceptable salt as claimed in claim 2, wherein the compound is represented by general formula (I-2):

(I-2)

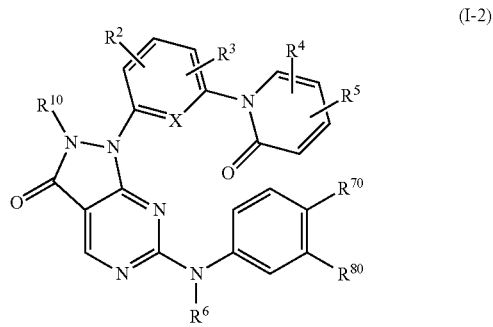

wherein $R^{10}$ means a C2-C6 alkenyl group;
$R^2$, $R^3$, $R^4$ and $R^5$ each independently mean a hydrogen atom, a halogen atom, a C1-C6 alkyl group, a halo-C1-C6 alkyl group, a C1-C6 alkoxy group or a halo-C1-C6 alkoxy group;
$R^6$ means a hydrogen atom or a C1-C6 alkyl group;
$R^{70}$ means a group of $-Q^2-N(R^{10c})R^{10d}$, or means a nitrogen-containing heterocyclic group selected from the group consisting of an azetidin-1-yl group, a pyrrolidin-1-yl group, a 4-piperidinyl group, a 1-piperazinyl group, a 1,2-dihydropyridin-1-yl group, a 2,7-diazaspiro[3.5]non-7-yl group, a 2,7-diazabicyclo[3.3.0]oct-2-yl group and a 3,6-diazabicyclo[3.3.0]oct-3-yl group, any of which may be substituted with a substituent selected from the group consisting of a halogen atom, a C1-C6 alkyl group, a hydroxy-C1-C6 alkyl group, an oxo group and a group of $-Q^1-N(R^{10a})R^{10b}$;
$R^{80}$ means a hydrogen atom, a C1-C6 alkyl group, a C1-C6 alkoxy group or a hydroxy-C1-C6 alkyl group;
or $R^{70}$ and $R^{80}$ may form, as taken together, a C2-C6 alkylene group, and one or two methylene groups constituting the C2-C6 alkylene group are each independently replaced by a group of $-N(R^{10e})-$;
$R^{10a}$ and $R^{10b}$ each independently mean a hydrogen atom or a C1-C6 alkyl group, or, as taken together, they form a C2-C6 alkylene group;
$R^{10c}$ and $R^{10d}$ each independently mean a C1-C6 alkyl group optionally substituted with a substituent selected from the group consisting of a hydroxyl group, an oxo group, a C3-C6 cycloalkyl group and a pyridyl group;

$R^{10e}$ means a C1-C6 alkyl group;

$Q^1$ and $Q^2$ each independently mean a single bond or a C1-C3 alkylene group; and X means a methine group or a nitrogen atom.

10. The compound or its pharmaceutically-acceptable salt as claimed in claim 1, wherein the compound is selected from the following:

(1) 6'-(2-allyl-6-{[4-(4-methylpiperazin-1-yl)phenyl]amino}-3-oxo-2,3-dihydro-1H-pyrazolo[3,4-d]pyrimidin-1-yl)-2H-1,2'-bipyridin-2-one;

(2) 6'-[2-allyl-6-({4-[(3R)-3-(dimethylamino)pyrrolidin-1-yl]phenyl}amino)-3-oxo-2,3-dihydro-1H-pyrazolo[3,4-d]pyrimidin-1-yl]-2H-1,2'-bipyridin-2-one;

(3) 6'-[2-allyl-6-({4-[(3S)-3-(dimethylamino)pyrrolidin-1-yl]phenyl}amino)-3-oxo-2,3-dihydro-1H-pyrazolo[3,4-d]pyrimidin-1-yl]-2H-1,2'-bipyridin-2-one;

(4) 2-allyl-1-[3-fluoro-5-(2-oxopyridin-1(2H)-yl)phenyl]-6-{[4-(4-methylpiperazin-1-yl)phenyl]amino}-1,2-dihydro-3H-pyrazolo[3,4-d]pyrimidin-3-one, (5) 6'-(2-allyl-6-{[4-(4-methylpiperazin-1-yl)phenyl]amino}-3-oxo-2,3-dihydro-1H-pyrazolo[3,4-d]pyrimidin-1-yl)-5-fluoro-2H-1,2'-bipyridin-2-one, (6) 6'-[2-allyl-6-({4-[(tert-butylamino)methyl]phenyl}amino)-3-oxo-2,3-dihydro-1H-pyrazolo[3,4-d]pyrimidin-1-yl]-2H-1,2'-bipyridin-2-one, (7) 2-allyl-6-{[4-(4-methylpiperazin-1-yl)phenyl]amino}-1-[3-(2-oxopyridin-1(2H)-yl)phenyl]-1,2-dihydro-3H-pyrazolo[3,4-d]pyrimidin-3-one, (8) 2-allyl-6-{[4-(1-methylpiperidin-4-yl)phenyl]amino}-1-[3-(2-oxopyridin-1(2H)-yl)phenyl]-1,2-dihydro-3H-pyrazolo[3,4-d]pyrimidin-3-one, (9) 6'-(2-allyl-6-{[4-(1-methylpiperidin-4-yl)phenyl]amino}-3-oxo-2,3-dihydro-1H-pyrazolo[3,4-d]pyrimidin-1-yl)-2H-1,2'-bipyridin-2-one,

(10) 6'-(2-allyl-6-{[3-(hydroxymethyl)-4-(4-methylpiperazin-1-yl)phenyl]amino}-3-oxo-2,3-dihydro-1H-pyrazolo[3,4-d]pyrimidin-1-yl)-2H-1,2'-bipyridin-2-one,

(11) 6'-(2-allyl-6-{[3-methyl-4-(4-methylpiperazin-1-yl)phenyl]amino}-3-oxo-2,3-dihydro-1H-pyrazolo[3,4-d]pyrimidin-1-yl)-2H-1,2'-bipyridin-2-one,

(12) 6'-(2-allyl-6-{[4-(4-methylpiperazin-1-yl)phenyl]amino}-3-oxo-2,3-dihydro-1H-pyrazolo[3,4-d]pyrimidin-1-yl)-3-methyl-2H-1,2'-bipyridin-2-one,

(13) 6'-(2-allyl-6-{[4-(4-methylpiperazin-1-yl)phenyl]amino}-3-oxo-2,3-dihydro-1H-pyrazolo[3,4-d]pyrimidin-1-yl)-4-methyl-2H-1,2'-bipyridin-2-one,

(14) 6'-(2-allyl-6-{[4-(4-methylpiperazin-1-yl)phenyl]amino}-3-oxo-2,3-dihydro-1H-pyrazolo[3,4-d]pyrimidin-1-yl)-5-methyl-2H-1,2'-bipyridin-2-one,

(15) 6'-(2-allyl-6-{[4-(4-methylpiperazin-1-yl)phenyl]amino}-3-oxo-2,3-dihydro-1H-pyrazolo[3,4-d]pyrimidin-1-yl)-3-methoxy-2H-1,2'-bipyridin-2-one,

(16) 6'-(2-allyl-6-{[4-(4-methylpiperazin-1-yl)phenyl]amino}-3-oxo-2,3-dihydro-1H-pyrazolo[3,4-d]pyrimidin-1-yl)-5-(trifluoromethyl-2H-1,2'-bipyridin-2-one,

(17) 6'-(2-allyl-6-{[4-(3,3-difluoroazetidin-1-yl)phenyl]amino}-3-oxo-2,3-dihydro-1H-pyrazolo[3,4-d]pyrimidin-1-yl)-2H-1,2'-bipyridin-2-one,

(18) N-(3-{[2-allyl-3-oxo-1-(2-oxo-2H-1,2'-bipyridin-6'-yl)-2,3-dihydro-1H-pyrazolo[3,4-d]pyrimidin-6-yl]amino}phenyl)cyclopropanecarboxamide,

(19) 6'-[2-allyl-6-({4-[3-(dimethylamino)propyl]phenyl}amino)-3-oxo-2,3-dihydro-1H-pyrazolo[3,4-d]pyrimidin-1-yl]-2H-1,2'-bipyridin-2-one,

(20) 6'-[2-allyl-6-({4-[3-(dimethylamino)azetidin-1-yl]phenyl}amino)-3-oxo-2,3-dihydro-1H-pyrazolo[3,4-d]pyrimidin-1-yl]-2H-1,2'-bipyridin-2-one,

(21) 6'-[2-allyl-6-({4-[(diethylamino)methyl]phenyl}amino)-3-oxo-2,3-dihydro-1H-pyrazolo[3,4-d]pyrimidin-1-yl]-2H-1,2'-bipyridin-2-one,

(22) 6'-(2-allyl-3-oxo-6-{[4-(2-oxopyrrolidin-1-yl)phenyl]amino}-2,3-dihydro-1H-pyrazolo[3,4-d]pyrimidin-1-yl)-2H-1,2'-bipyridin-2-one,

(23) 6'-(2-allyl-3-oxo-6-{[4-(2-oxopyridin-1(2H)-yl)phenyl]amino}-2,3-dihydro-1H-pyrazolo[3,4-d]pyrimidin-1-yl)-2H-1,2'-bipyridin-2-one,

(24) 6'-[2-allyl-6-({4-[(2S)-2-(hydroxymethyl)pyrrolidin-1-yl]phenyl}amino)-3-oxo-2,3-dihydro-1H-pyrazolo[3,4-d]pyrimidin-1-yl]-2H-1,2'-bipyridin-2-one,

(25) 6'-[2-allyl-6-({4-[(2R)-2-(hydroxymethyl)pyrrolidin-1-yl]phenyl}amino)-3-oxo-2,3-dihydro-1H-pyrazolo[3,4-d]pyrimidin-1-yl]-2H-1,2'-bipyridin-2-one,

(26) 6'-{2-allyl-3-oxo-6-[(2,2,3,3-tetrafluoro-2,3-dihydro-1,4-benzodioxin-6-yl)amino]-2,3-dihydro-1H-pyrazolo[3,4-d]pyrimidin-1-yl}-2H-1,2'-bipyridin-2-one,

(27) 6'-(2-allyl-6-{[3-(1-methylpiperizin-4-yl)phenyl]amino}-3-oxo-2,3-dihydro-1H-pyrazolo[3,4-d]pyrimidin-1-yl)-2H-1,2'-bipyridin-2-one,

(28) 6'-[2-allyl-3-oxo-6-({4-[(2S)-2-(pyrrolidin-1-ylmethyl)pyrrolidin-1-yl]phenyl}amino)-2,3-dihydro-1H-pyrazolo[3,4-d]pyrimidin-1-yl]-2H-1,2'-bipyridin-2-one,

(29) 6'-(2-allyl-6-{[3-(hydroxymethyl)-4-methoxyphenyl]amino}-3-oxo-2,3-dihydro-1H-pyrazolo[3,4-d]pyrimidin-1-yl)-2H-1,2'-bipyridin-2-one,

(30) 6'-{2-allyl-6-[(2-methyl-1,2,3,4-tetrahydroisoquinolin-7-yl)amino]-3-oxo-2,3-dihydro-1H-pyrazolo[3,4-d]pyrimidin-1-yl}-2H-1,2'-bipyridin-2-one,

(31) 6'-[2-allyl-6-({4-[methyl(pyridin-2-ylmethyl)amino]phenyl}amino)-3-oxo-2,3-dihydro-1H-pyrazolo[3,4-d]pyrimidin-1-yl]-2H-1,2'-bipyridin-2-one,

(32) 6'-(2-allyl-6-{[4-(2-methyl-2,7-diazaspiro[3.5]non-7-yl)phenyl]amino}-3-oxo-2,3-dihydro-1H-pyrazolo[3,4-d]pyrimidin-1-yl)-2H-1,2'-bipyridin-2-one,

(33) 6'-(2-allyl-6-{[4-(5-methylhexahydropyrrolo[3,4-b]pyrrol-1(2H)-yl)phenyl]amino}-3-oxo-2,3-dihydro-1H-pyrazolo[3,4-d]pyrimidin-1-yl)-2H-1,2'-bipyridin-2-one,

(34) 6'-(2-allyl-6-{[4-(1-methylhexahydropyrrolo[3,4-b]pyrrol-5(1H)-yl)phenyl]amino}-3-oxo-2,3-dihydro-1H-pyrazolo[3,4-d]pyrimidin-1-yl)-2H-1,2'-bipyridin-2-one,

(35) 6'-[2-allyl-6-({4-[3-(tert-butylamino)pyrrolidin-1-yl]phenyl}amino)-3-oxo-2,3-dihydro-1H-pyrazolo[3,4-d]pyrimidin-1-yl]-2H-1,2'-bipyridin-2-one,

(36) 6'-{2-isopropyl-6-[(2-methyl-1,2,3,4-tetrahydroisoquinolin-7-yl)amino]-3-oxo-2,3-dihydro-1H-pyrazolo[3,4-d]pyrimidin-1-yl}-2H-1,2'-bipyridin-2-one,

(37) 6'-{2-methyl-6-[(2-methyl-1,2,3,4-tetrahydroisoquinolin-6-yl)amino]-3-oxo-2,3-dihydro-1H-pyrazolo[3,4-d]pyrimidin-1-yl}-2H-1,2'-bipyridin-2-one,

(38) 6'-{2-methyl-6-[(2'-methyl-2',3'-dihydro-1'H-spiro[cyclopropane-1,4'-isoquinolin]-7'-yl)amino]-3-oxo-2,3-dihydro-1H-pyrazolo[3,4-d]pyrimidin-1-yl}-2H-1,2'-bipyridin-2-one,

(39) 6'-{2-isopropyl-6-[(2'-methyl-2',3'-dihydro-1'H-spiro[cyclopropane-1,4'-isoquinolin]-7'-yl)amino]-3-oxo-2,3-dihydro-1H-pyrazolo[3,4-d]pyrimidin-1-yl}-2H-1,2'-bipyridin-2-one,

(40) 6'-{2-isopropyl-3-oxo-6-[(2,4,4-trimethyl-1,2,3,4-tetrahydroisoquinolin-7-yl)amino]-2,3-dihydro-1H-pyrazolo[3,4-d]pyrimidin-1-yl}-2H-1,2'-bipyridin-2-one,

(41) 6'-{2-ethyl-6-[(2'-methyl-2',3'-dihydro-1'H-spiro[cyclopropane-1,4'-isoquinolin]-7'-yl)amino]-3-oxo-2,3-dihydro-1H-pyrazolo[3,4-d]pyrimidin-1-yl}-2H-1,2'-bipyridin-2-one, or

(42) 6'-{6-[(2-methyl-1,2,3,4-tetrahydroisoquinolin-7-yl)amino]-3-oxo-2-(2-propynyl)-2,3-dihydro-1H-pyrazolo[3,4-d]pyrimidin-1-yl}-2H-1,2'-bipyridin-2-one.

11. A pharmaceutical composition comprising a therapeutically-effective amount of the compound of claim 1 or its pharmaceutically-acceptable salt, and a pharmaceutically-acceptable carrier or diluent.

12. A method for the treatment of a WEE1 kinase-associated cancer selected from breast cancer, lung cancer, pancreatic cancer, colon cancer, ovarian cancer, acute leukemia, chronic lymphatic leukemia, chronic myelocytic leukemia, or Hodgkin's lymphoma, which comprises administering to a subject in need thereof a therapeutically-effective amount of the compound or its pharmaceutically-acceptable salt of claim 1.

13. The method of claim 12, which further comprises administering to a subject in need thereof a therapeutically-effective amount of radiation therapy.

* * * * *